(12) United States Patent
Xia

(10) Patent No.: US 9,196,860 B2
(45) Date of Patent: Nov. 24, 2015

(54) COMPOUNDS FOR TRIPLET-TRIPLET ANNIHILATION UPCONVERSION

(71) Applicant: Chuanjun Xia, Ewing, NJ (US)

(72) Inventor: Chuanjun Xia, Ewing, NJ (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 150 days.

(21) Appl. No.: 13/693,122

(22) Filed: Dec. 4, 2012

(65) Prior Publication Data

US 2014/0151646 A1  Jun. 5, 2014

(51) Int. Cl.
*H01L 35/24* (2006.01)
*H01L 51/52* (2006.01)

(52) U.S. Cl.
CPC ...................................... *H01L 51/52* (2013.01)

(58) Field of Classification Search
CPC ............ H01L 51/0545; H01L 51/0541; H01L 51/0036; H01L 51/5012; B82Y 10/00
USPC ............................................ 257/40, E51.001
See application file for complete search history.

(56) References Cited

U.S. PATENT DOCUMENTS

| | | | |
|---|---|---|---|
| 4,769,292 A | 9/1988 | Tang et al. |
| 5,061,569 A | 10/1991 | VanSlyke et al. |
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,921,915 B2 | 7/2005 | Takiguchi et al. |
| 7,090,928 B2 | 8/2006 | Thompson et al. |

(Continued)

FOREIGN PATENT DOCUMENTS

| EP | 650955 | 5/1995 |
|---|---|---|
| EP | 1725079 | 11/2006 |

(Continued)

OTHER PUBLICATIONS

Adachi et al., "High-efficiency red electrophosphorescence devices", Applied Physics Letters, vol. 78, No. 11, Mar. 12, 2001.

(Continued)

*Primary Examiner* — Anthony Ho
(74) *Attorney, Agent, or Firm* — Morris & Kamlay LLP

(57) ABSTRACT

Novel compounds, and in particular, a dendritic system for improved triple-triplet annihilation upconversion (TTA-UC) are provided. The core of the dendrimer compound includes a metal complex, and on the peripheral, multiple acceptor moieties are covalently linked to the core through a spacer. Consequently, a high efficiency TTA-UC system in both solution and solid state is provided, with particularly high efficiency in the solid state. Additionally, organic light emitting devices (OLEDs) comprising a layer including these novel compounds are provided.

30 Claims, 3 Drawing Sheets

(56) References Cited

U.S. PATENT DOCUMENTS

| | | |
|---|---|---|
| 7,154,114 B2 | 12/2006 | Brooks et al. |
| 7,230,107 B1 | 6/2007 | Herron et al. |
| 7,232,618 B2 | 6/2007 | Yamada et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 7,655,323 B2 | 2/2010 | Walters et al. |
| 7,968,146 B2 | 6/2011 | Wagner et al. |
| 2001/0015432 A1 | 8/2001 | Igarashi |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0115476 A1 | 6/2004 | Oshiyama et al. |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0123751 A1 | 6/2005 | Tsutsui et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2006/0008670 A1 | 1/2006 | Lin et al. |
| 2006/0121308 A1 | 6/2006 | Katoh et al. |
| 2006/0127696 A1 | 6/2006 | Stossel et al. |
| 2006/0182992 A1 | 8/2006 | Nii et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0087321 A1 | 4/2007 | Pribenszky et al. |
| 2007/0103060 A1 | 5/2007 | Itoh et al. |
| 2007/0111026 A1 | 5/2007 | Deaton et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0261076 A1 | 10/2008 | Kwong et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2009/0302743 A1 | 12/2009 | Kato et al. |
| 2009/0309488 A1 | 12/2009 | Kato et al. |
| 2010/0012931 A1 | 1/2010 | Kato et al. |
| 2010/0084966 A1 | 4/2010 | Otsu et al. |
| 2010/0090591 A1 | 4/2010 | Alleyne et al. |
| 2010/0108994 A1 | 5/2010 | Schäfer et al. |
| 2010/0148663 A1 | 6/2010 | Tsai et al. |
| 2010/0187984 A1 | 7/2010 | Lin et al. |
| 2010/0244004 A1 | 9/2010 | Xia et al. |
| 2010/0295032 A1 | 11/2010 | Kwong et al. |
| 2011/0057559 A1 | 3/2011 | Xia et al. |
| 2011/0089407 A1 | 4/2011 | Schmidhalter et al. |
| 2011/0163302 A1 | 7/2011 | Lin et al. |
| 2011/0204333 A1 | 8/2011 | Xia et al. |
| 2011/0227049 A1 | 9/2011 | Xia et al. |
| 2011/0304263 A1 | 12/2011 | Xia et al. |

FOREIGN PATENT DOCUMENTS

| | | |
|---|---|---|
| EP | 1841834 | 10/2007 |
| EP | 2034538 | 3/2009 |
| EP | 2350216 | 8/2011 |
| JP | 2007123392 | 5/2007 |
| JP | 2007254297 | 10/2007 |
| JP | 2008074939 | 4/2008 |
| WO | 0202714 | 1/2002 |
| WO | 0215645 | 2/2002 |
| WO | 03040257 | 5/2003 |
| WO | 2004/093207 | 10/2004 |
| WO | 2004/107822 | 12/2004 |
| WO | 2005/014551 | 2/2005 |
| WO | 2005/019373 | 3/2005 |
| WO | 2005/030900 | 4/2005 |
| WO | 2005/089025 | 9/2005 |
| WO | 2005/123873 | 12/2005 |
| WO | 2005123873 A1 | 12/2005 |
| WO | 2006/009024 | 1/2006 |
| WO | 2006009024 A1 | 1/2006 |
| WO | 2006/056418 | 6/2006 |
| WO | 2006/072002 | 7/2006 |
| WO | 2006/082742 | 8/2006 |
| WO | 2006082742 A1 | 8/2006 |
| WO | 2006/098120 | 9/2006 |
| WO | 2006/100298 | 9/2006 |
| WO | 2006/103874 | 10/2006 |
| WO | 2006/114966 | 11/2006 |
| WO | 2006/132173 | 12/2006 |
| WO | 2007/002683 | 1/2007 |
| WO | 2007/004380 | 1/2007 |
| WO | 2007004380 A1 | 1/2007 |
| WO | 2007/063754 | 6/2007 |
| WO | 2007/063796 | 6/2007 |
| WO | 2008/056746 | 5/2008 |
| WO | 2008057394 | 5/2008 |
| WO | 2008/101842 | 8/2008 |
| WO | 2008/132085 | 11/2008 |
| WO | 2009/000673 | 12/2008 |
| WO | 2009/003898 | 1/2009 |
| WO | 2009/008311 | 1/2009 |
| WO | 2009/018009 | 2/2009 |
| WO | 2009/021126 | 2/2009 |
| WO | 2009/050290 | 4/2009 |
| WO | 2009/063833 | 5/2009 |
| WO | 2009/066778 | 5/2009 |
| WO | 2009/066779 | 5/2009 |
| WO | 2009/086028 | 7/2009 |
| WO | 2009/100991 | 8/2009 |
| WO | 2010011390 | 1/2010 |
| WO | 2010/028151 | 3/2010 |
| WO | 2010028151 A1 | 3/2010 |
| WO | 2010/056066 | 5/2010 |
| WO | 2010/079051 | 7/2010 |
| WO | 2010/086089 | 8/2010 |
| WO | 2010086089 A1 | 8/2010 |
| WO | 2010/107244 | 9/2010 |
| WO | 2011/044988 | 4/2011 |
| WO | 2011/051404 | 5/2011 |
| WO | 2011051404 A1 | 5/2011 |
| WO | 2011/075644 | 6/2011 |
| WO | 2011/086863 | 7/2011 |

OTHER PUBLICATIONS

Adachi et al., "Nearly 100% internal phosphorescence efficiency in an organic light emitting device", Journal of Applied Physics, vol. 90, No. 10, Nov. 15, 2001.

(56) References Cited

OTHER PUBLICATIONS

Adachi et al., "Organic electroluminescent device having a hole conductor as an emitting layer", Applied Physics Letters, vol. 55, Oct. 9, 1989.

Aonuma et al., "Material design of hole transport materials capable of thick-filim formation in organic light emitting diodes", Applied Physics Letters, vol. 90, 2007.

Baldo et al., "Highly efficient phosphorescent emission from organic electroluminescent devices", Nature, vol. 395, pp. 151-154, 1998.

Baldo et al., "Very high-efficiency green organic light-emitting devices based on electrophosphorescence", Applied Physics Letters, vol. 75, No. 1, pp. 4-6, Jul. 5, 1999.

Chang et al., "Highly Efficient Blue-Emitting Iridium(III) Carbene Complexes and Phosphorescent OLEDs", Angew. Chem. Int. Ed. 47, pp. 4542-4545, 2008.

Gao et al., "Bright-blue electroluminescence from a silyl-substituted ter-(phenylene-vinylene) derivative", Applied Physics Letters, vol. 74, No. 6, Feb. 8, 1999.

Guo et al., "Highly efficient electrophosphorescent polymer light-emitting devices", Organic Electronics 1, pp. 15-20, 2000.

Hamada et al., "High Luminance in Organic Electroluminescent Devices with Bis(10-hydroxybenzo[h]quinolinato)beryllium as an Emitter", Chemistry Letters, pp. 905-906, 1993.

Holmes et al., "Blue organic electrophosphorescence using exothermic host-guest energy transfer", Applied Physics Letters, vol. 82, No. 15, Apr. 14, 2003.

Hu et al., "Novel high Tg hole-transport molecules based on indolo[3,2-b ]carbazoles for organic light-emitting devices", Synthetic Metals 111-112, pp. 421-424, 2000.

Huang et al., "Highly Efficient Red-Emission Polymer Phosphorescent Light-Emitting Diodes Based on Two Novel Tris(I-phenylisoquinolinato-C2,N)iridium(III) Derivatives", Advanced Materials, No. 19, 2007.

Huang et al., "Highly Phosphorescent Bis-Cyclometalated Iridium Complexes Containing Benzoimidazole-Based Ligands", Chemistry of Materials, vol. 16, 2004.

Hung et al., "Anode modification in organic light-emitting diodes by low-frequency plasma polymerization of CHF3", Applied Physics Letters, vol. 78, No. 5, Jan. 29, 2001.

Ikeda et al., "P-185: Low-Drive-Voltage OLEDs with a Buffer Layer Having Molybdenum Oxide", Society for Information Display Digest, pp. 923-926, 2006.

Kanno et al., "Highly efficient and stable red phosphorescent organic light-emitting device using bis[2-(2-benzothiazoyl)phenolato]zinc(II) as host material", Applied Physics Letters, vol. 90, 2007.

Kido et al., "1,2,4-Triazole Derivative as an Electron Transport Layer in Organic Electroluminescent Devices", Japanese Journal of Applied Physics, vol. 32, pp. L 917-L 920 Part 2, No. 7A, Jul. 1, 1993.

Kuwabara et al., "Thermally Stable Multilayered Organic Electroluminescent Devices Using Novel Starburst Molecules, 4,4' ,4"-Tri(N-carbazolyl)triphenylamine (TCTA) and 4,4' ,4"-Tris(3-methylphenylphenylamino) triphenylamine (m-MTDATA), as Hole-Transport Materials", Advanced Materials, 6, No. 9, 1994.

Kwong et al., "High operational stability of electrophosphorescent devices", Applied Physics Letters, vol. 81, No. 1, Jul. 1, 2002.

Lamansky et al., "Synthesis and Characterization of Phosphorescent Cyclometalated Iridium Complexes", Inorganic Chemistry, vol. 40, No. 7, 2001.

Lee et al., "Polymer phosphorescent light-emitting devices doped with tris(2-phenylpyridine) iridium as a triplet emitter", Applied Physics Letters, vol. 77, No. 15, Oct. 9, 2000.

Lkai et al., "Highly efficient phosphorescence from organic light-emitting devices with an exciton-block layer", Applied Physics Letters, vol. 79, No. 2, Jul. 9, 2001.

Lnada et al., "1,3,5-Tris[4-(diphenylamino)phenyl]benzene and its Methyl substituted Derivatives as a Novel Class of Amorphous Molecular Materials", Journal of Materials Chemistry, vol. 3, 1993.

Lo et al., "Blue Phosphorescence from Iridium(III) Complexes at Room Temperature", Chemistry of Materials, vol. 18, 2006.

Ma et al., "Triplet luminescent dinuclear-gold complex-based light-emitting diodes with low turn-on voltage", Applied Physics Letters, vol. 74, No. 10, Mar. 8, 1999.

Mi et al., "Thermally Stable Hole-Transporting Material for Organic Light-Emitting Diode: an Isoindole Derivative", Chemistry of Materials, vol. 15, 2003.

Nishida et al., "Preparation, Characterization, and Electroluminescence Characteristics of a-Diimine-type Platinum(II) Complexes with Perfluorinated Phenyl Groups as Ligands", Chemistry Letters, vol. 34, No. 4, 2005.

Niu et al., "Highly Efficient Electrophosphorescent Devices with Saturated Red Emission from a Neutral Osmium Complex", Chemistry of Materials, vol. 17, 2005.

Noda et al., "5,5'-Bis(dimesitylbory1)-2,2'-bithiophene and 5,5"-Bis(dimesitylboryI)-2,2':5',2"-terthiophene as a Novel Family of Electron-Transporting Amorphous Molecular Materials", Journal of the American Chemical Society, vol. 120, No. 37, 1998.

Okumoto et al., "Green fluorescent organic light-emitting device with external quantum efficiency of nearly 10%", Applied Physics Letters, vol. 89, 2006.

Ostergard et al., "Langmuir-Blodgett light-emitting diodes of poly(3-hexylthiophene): electro-optical characteristics related to structure", Synthetic Metals 88, pp. 171-177, 1997.

Palilis et al., "High efficiency molecular organic light-emitting diodes based on silole derivatives and their exciplexes", Organic Electronics 4, pp. 113-121, 2003.

Ranjan et al., "Realizing Green Phosphorescent Light-Emitting Materials from Rhenium(I) Pyrazolato Diimine Complexes", Inorganic Chemistry, vol. 42, No. 4, 2003.

Sakamoto et al., "Synthesis, Characterization, and Electron-Transport Property of Perfluorinated Phenylene Dendrimers", Journal of the American Chemical Society, vol. 122, No. 8, 2000.

Salbeck et al., "Low molecular organic glasses for blue electroluminescence", Synthetic Metals 91, pp. 209-215, 1997.

Shirota et al., "Starburst molecules based on pi-electron systems as materials for organic electroluminescent devices", Journal of Luminescence 72-74, pp. 985-991, 1997.

Sotoyama et al., "Efficient organic light-emitting diodes with phosphorescent platinum complexes containing NCN-coordinating tridentate ligand", Applied Physics Letters, vol. 86, 2005.

Sun et al., "High-efficiency white organic light emitting devices with three separate phosphorescent emission layers", Applied Physics Letters, vol. 91, 2007.

Takizawa et al., "Phosphorescent Iridium Complexes Based on 2-Phenylimidazo[1 ,2-a]pyridine Ligands: Tuning of Emission Color toward the Blue Region and Application to Polymer Light-Emitting Devices", Inorganic Chemistry, vol. 46, No. 10, 2007.

Tang et al., "Organic electroluminescent diodes", Applied Physics Letters, No. 51, Sep. 21, 1987.

Tung et al., "Highly Efficient Red Phosphorescent Osmium(II) Complexes for OLED Applications", Organometallics, 23, pp. 3745-3748, 2004.

Tung et al., "Organic Light-Emitting Diodes based on Charge-Neutral Ru Phosphorescent Emitters", Advanced Materials, 17, No. 8, Apr. 18, 2005.

Van Slyke et al., "Organic electroluminescent devices with improved stability", Applied Physics Letters, 69 (15), Oct. 7, 1996.

Wang et al., "Highly efficient electroluminescent materials based on fluorinated organometallic iridium compounds", Applied Physics Letters, vol. 79, No. 4, Jul. 23, 2001.

Wong et al., "A novel class of phosphorescent gold(III) alkynyl-based organic light-emitting devices with tunable colour", Chemical Communications, Royal Society of Chemistry, p. 2906-2908, 2005.

Wong et al., "Multifunctional Iridium Complexes Based on Carbazole Modules as Highly Efficient Electrophosphers", Angewandte Chemie, Int. Ed., No. 45, 2006.

COMPOUNDS FOR TRIPLET-TRIPLET ANNIHILATION UPCONVERSION

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to devices involving light emission and light absorption such as light-emitting diodes (LEDs), organic light-emitting devices (OLEDs), and photovoltaic devices (PVs). More specifically, it relates to devices and materials that include materials capable of triple-triplet annihilation upconversion (TTA-UC), such as materials having a dendritic compound including a metal complex at the core, and on the peripheral, multiple acceptor moieties that are covalently linked to the core through a spacer.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)3, which has the following structure:

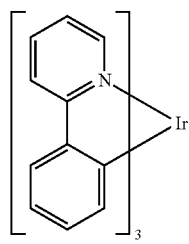

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processable" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

Devices and materials that make use of or provide triplet-triplet annihilation up-conversion (TTA-UC) to covert emission from a light source, e.g., an OLED, to an emission with shorter wavelength are provided.

In an aspect, compounds are provided which include a metal complex sensitizer core, an acceptor group, and a spacer group between the metal complex core and the acceptor group. The acceptor group has a first triplet energy lower than the first triplet energy of the metal complex sensitizer core.

In an aspect, the spacer group substantially surrounds the metal complex sensitizer core.

In an aspect, the compounds further comprise a second acceptor group. Additionally, the compounds may include a second spacer group.

In an aspect, the compounds further comprise a second spacer group. In an aspect, the second spacer group substantially surrounds the acceptor group.

In an aspect, the compounds further comprise a second acceptor group.

In an aspect, the second acceptor group substantially surrounds the second spacer group.

In an aspect, compounds for triplet-triplet annihilation upconversion are provided. The compounds have the following general structure:

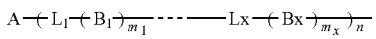

wherein A is a metal complex, $L_1$ to $L_x$ is a spacer group, $B_1$ to $B_x$ is an acceptor group B, $m_1$ is greater than 0, $m_x$ is equal to or greater than 0, n is greater than 0, and acceptor group B has a first triplet energy lower than a first triplet energy of the metal complex A.

In an aspect, $m_1$ is in the range of 1 to 20.
In an aspect, $m_x$ is in the range of 0 to 20.
In an aspect, n is in the range of 1 to 20.
In an aspect, the metal complex is selected from the group consisting of: an iridium complex, an osmium complex, a platinum complex, a palladium complex, a rhenium complex, a ruthenium complex, and a gold complex.

In an aspect, the acceptor group B is a fused aromatic group. In another aspect, the acceptor group B is a polycyclic aromatic compound such as a compound containing naphthalene, anthracene, tetracene, pyrene, chrysene, and perylene.

In an aspect, the ratio of the acceptor group B to the metal complex A is at least 4.

In an aspect, the spacer group L is selected from the group consisting of: alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, ester, and combinations thereof.

In an aspect, an organic light emitting device is provided. The organic light emitting device may include an emissive material having an emissive spectrum, and an upconversion layer disposed in the optical path of the organic light emitting device such that light emitted by the organic light emitting device is incident on the upconversion layer. The upconversion layer may include the compounds described herein. In an aspect, the device comprises an OLED.

In an aspect, the device further comprises a thin film encapsulation layer disposed over or under the OLED.

In an aspect, a device comprising a light emitting diode is provided. The device may include the compounds described herein. In an aspect, the light source is an inorganic LED. In an aspect, the light source is sun light.

In an aspect, a photovoltaic device is provided. An upconversion layer is disposed in the optical path of the incident light on the photovoltaic device. The upconversion layer may include the compounds described herein. In an aspect, a lighting panel comprising the compounds described herein is provided.

In an aspect, a consumer product comprising the compounds described herein is provided.

In an aspect, a compound is selected from the group consisting of:

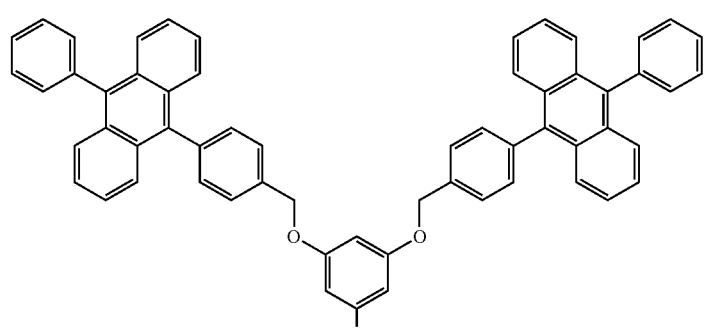

Compound 1

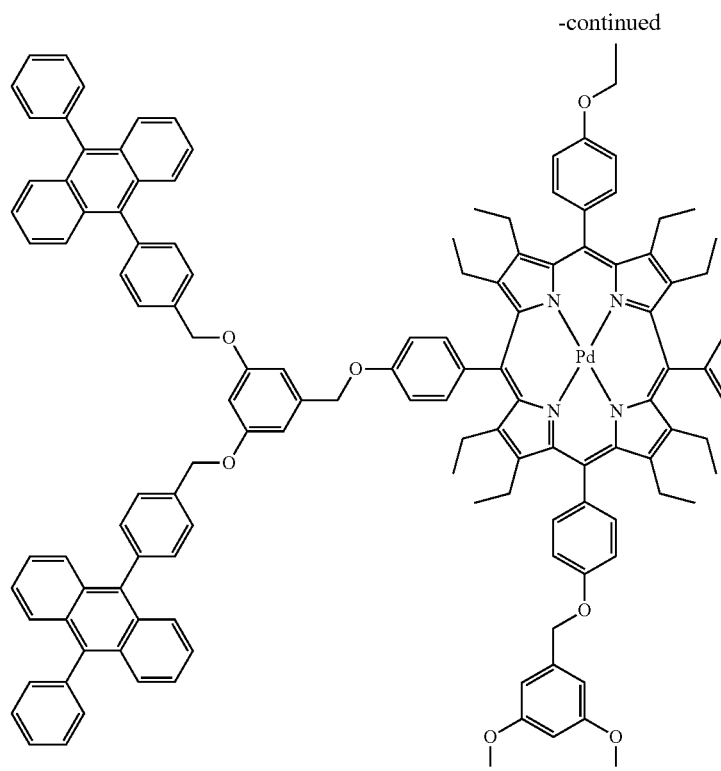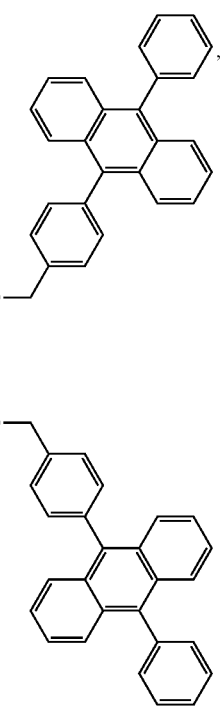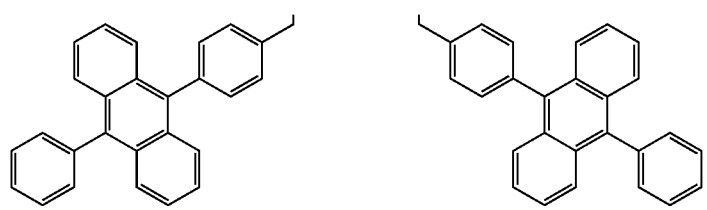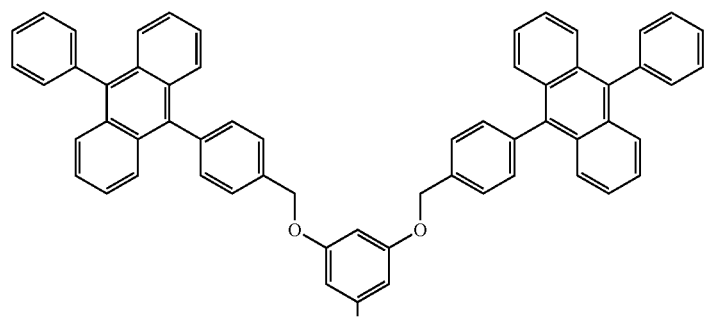
Compound 2

-continued
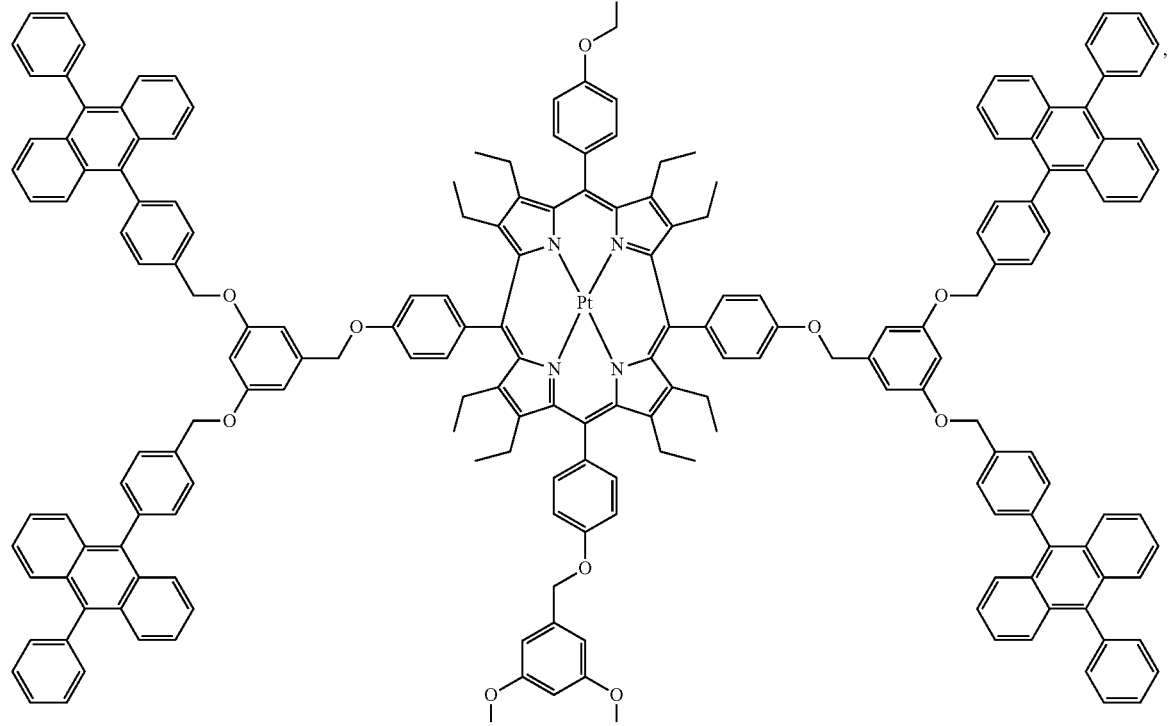
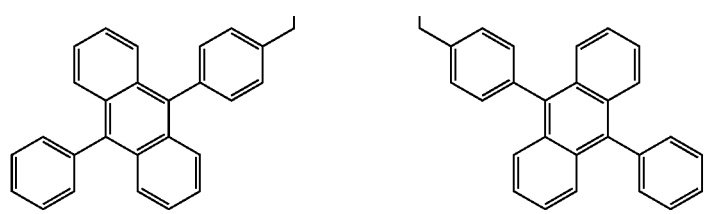
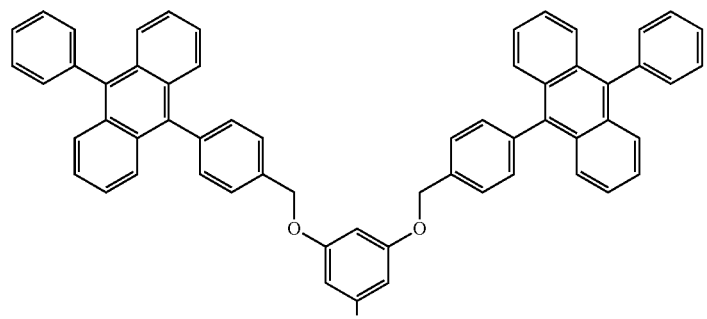
Compound 3

-continued
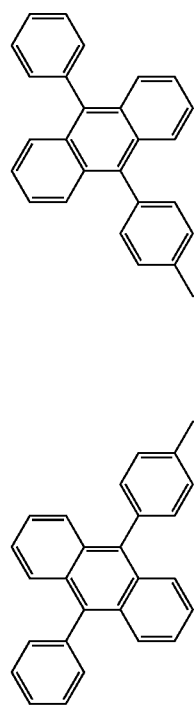
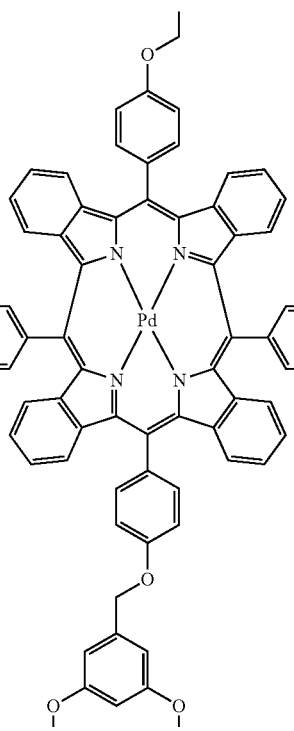
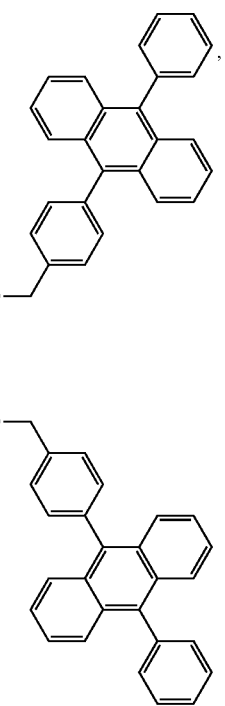
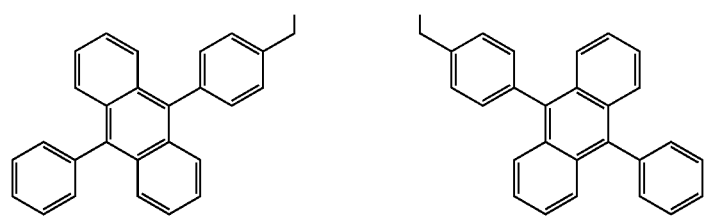

Compound 4
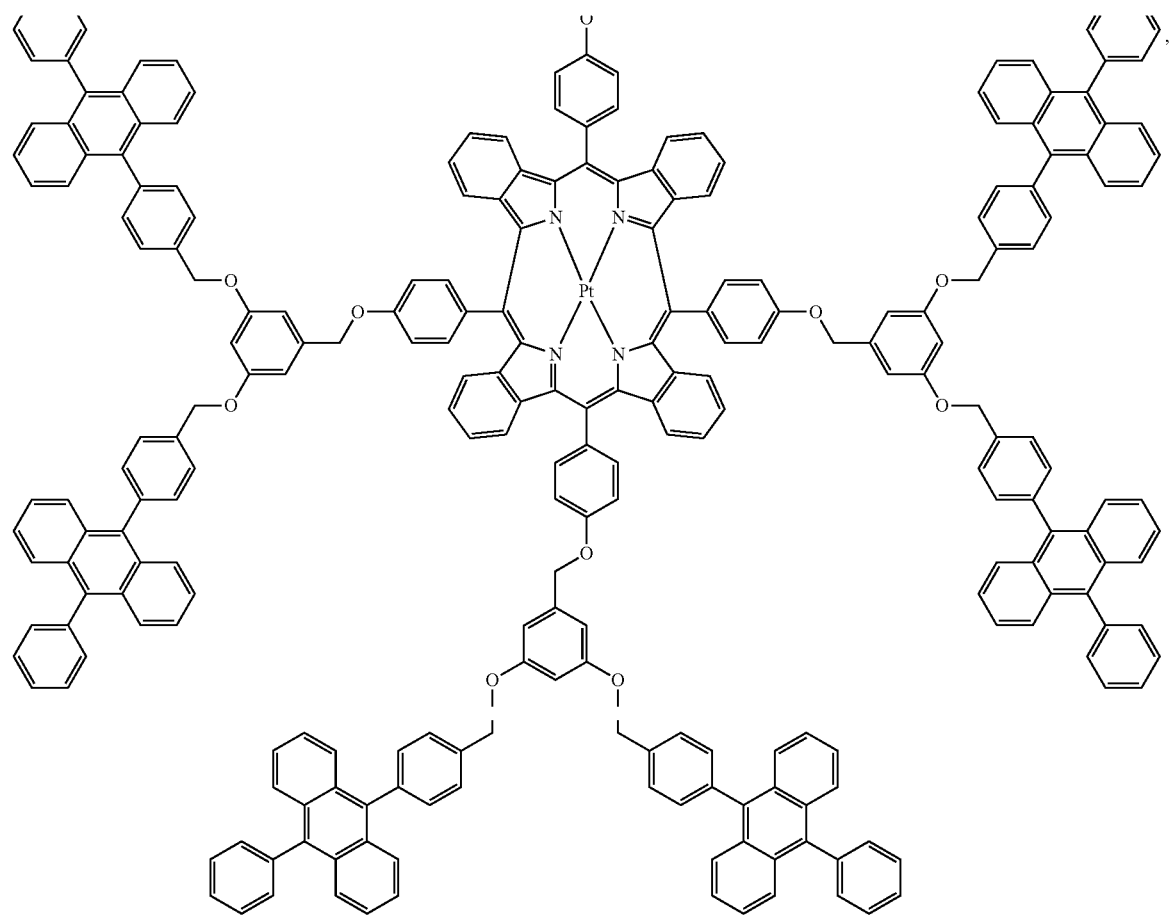
Compound 5
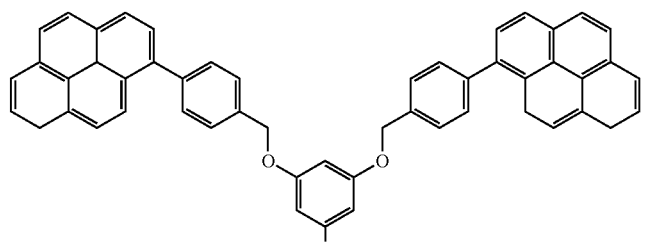

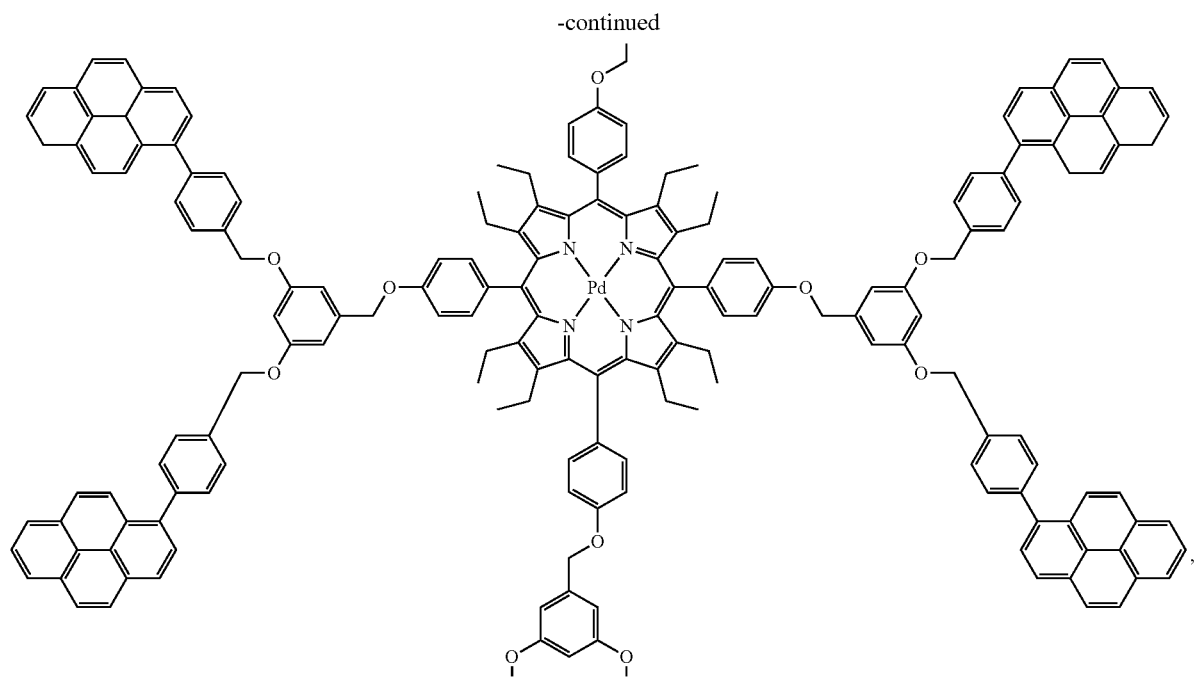
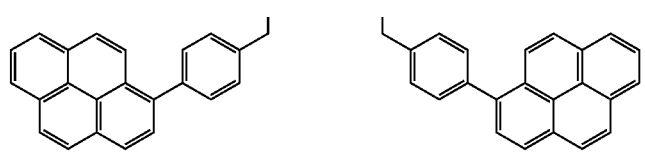
Compound 6
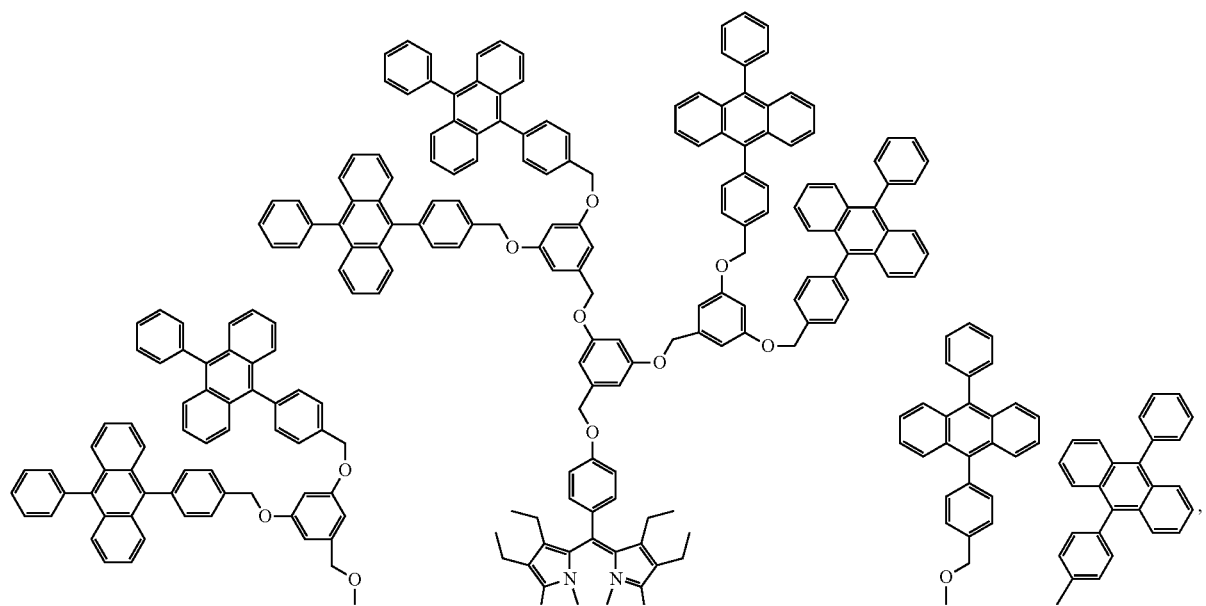

-continued
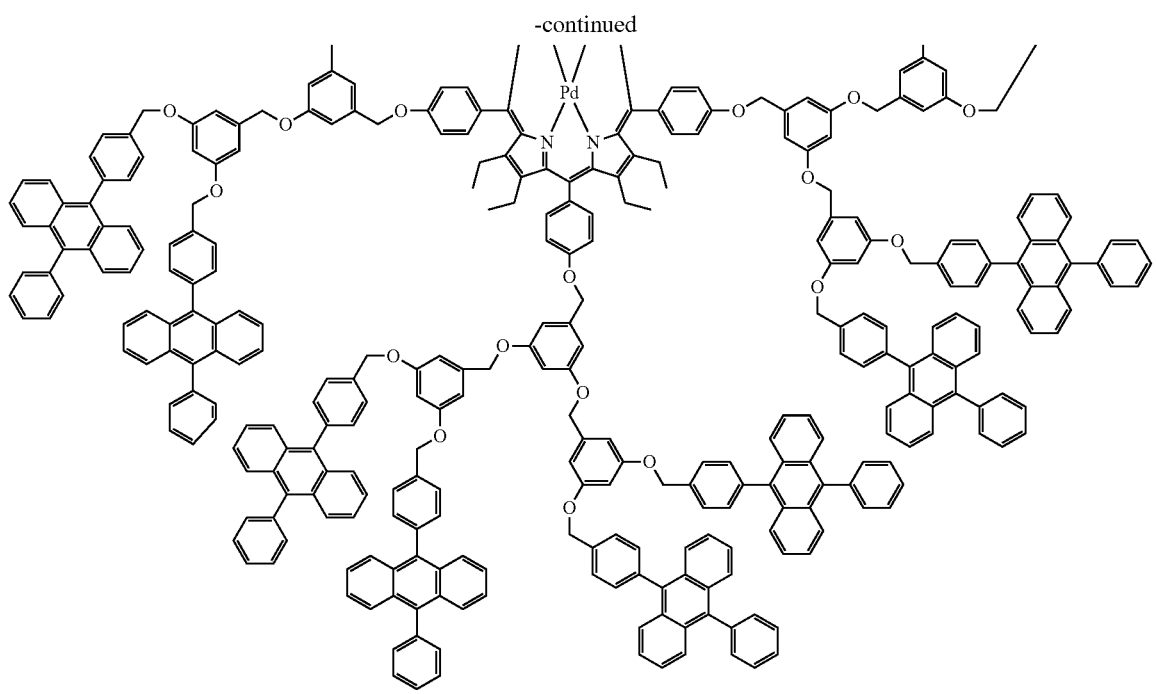
Compound 7
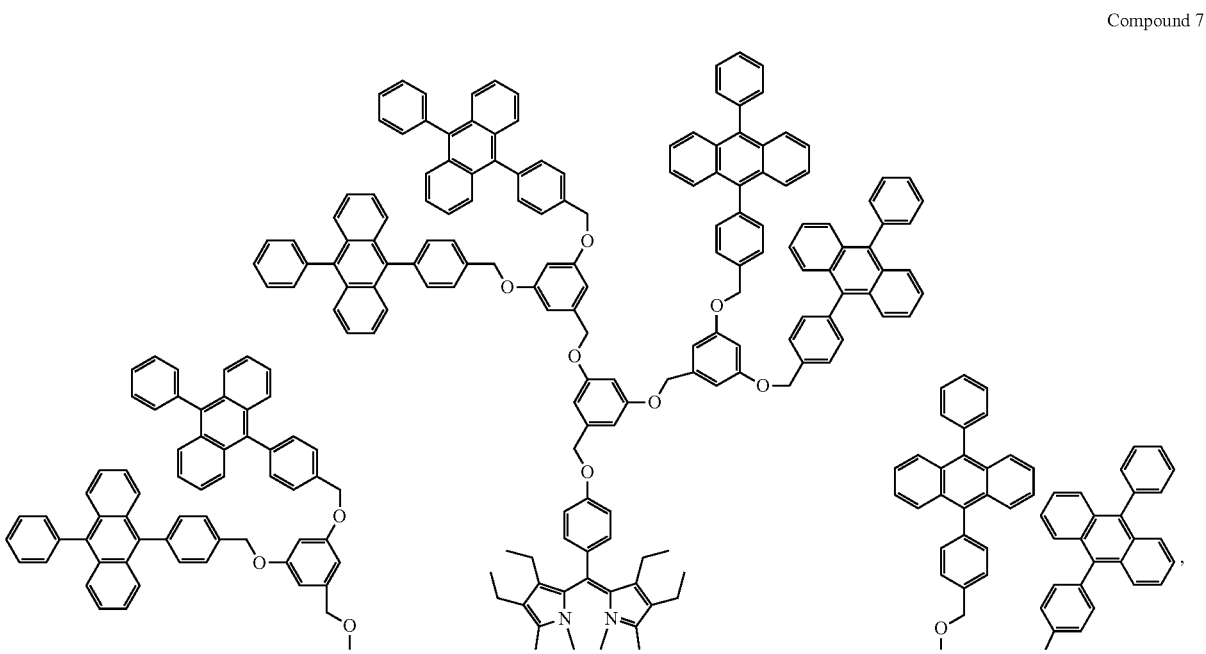

17
-continued
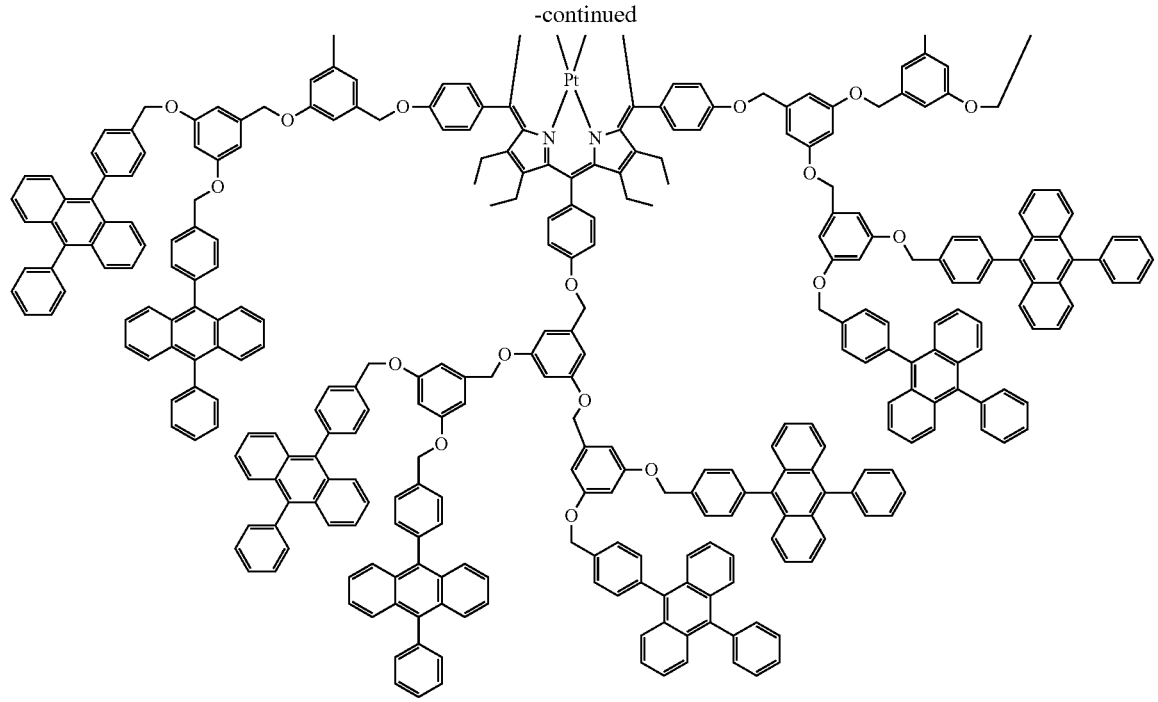
18
Compound 8
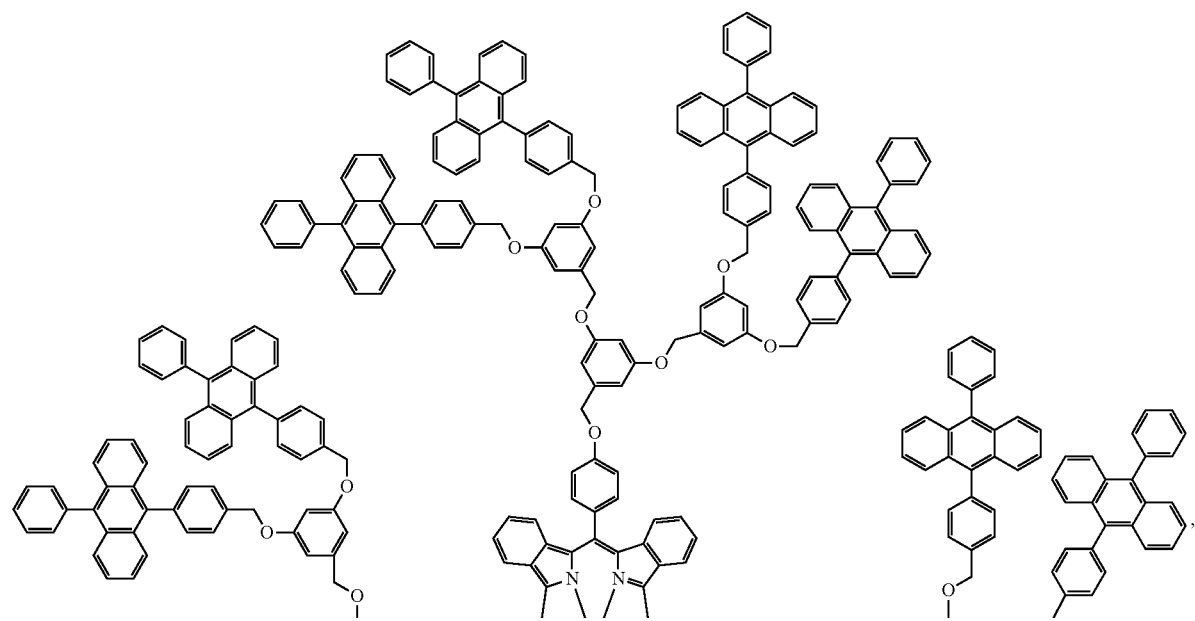

-continued
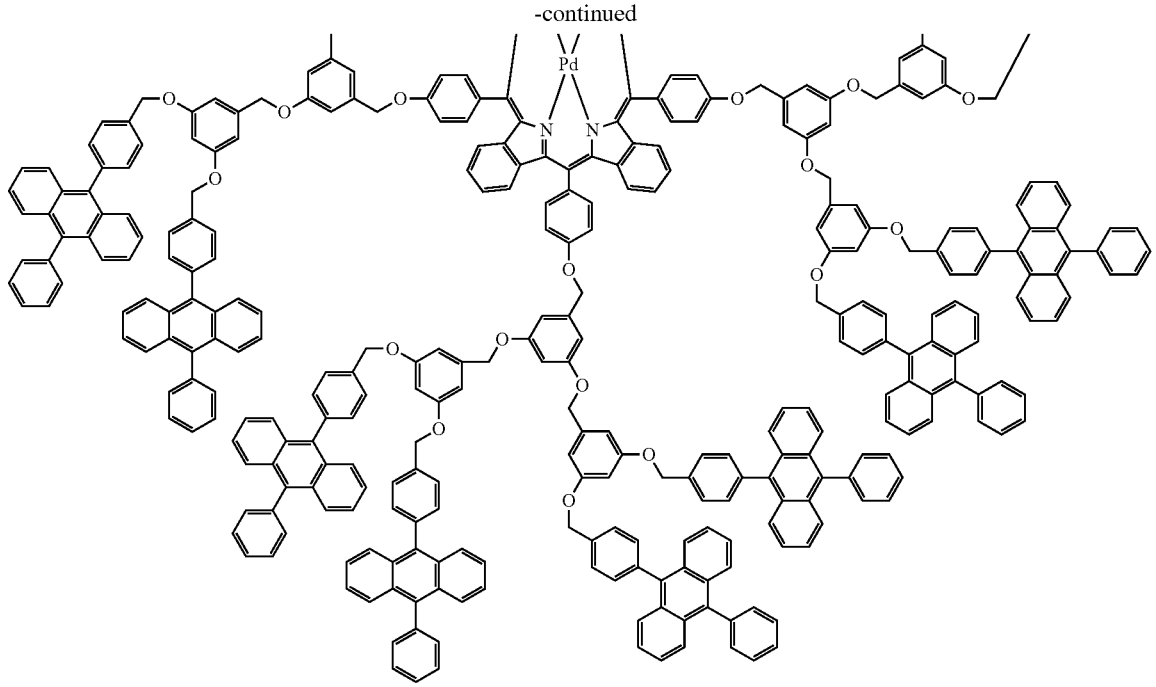
Compound 9
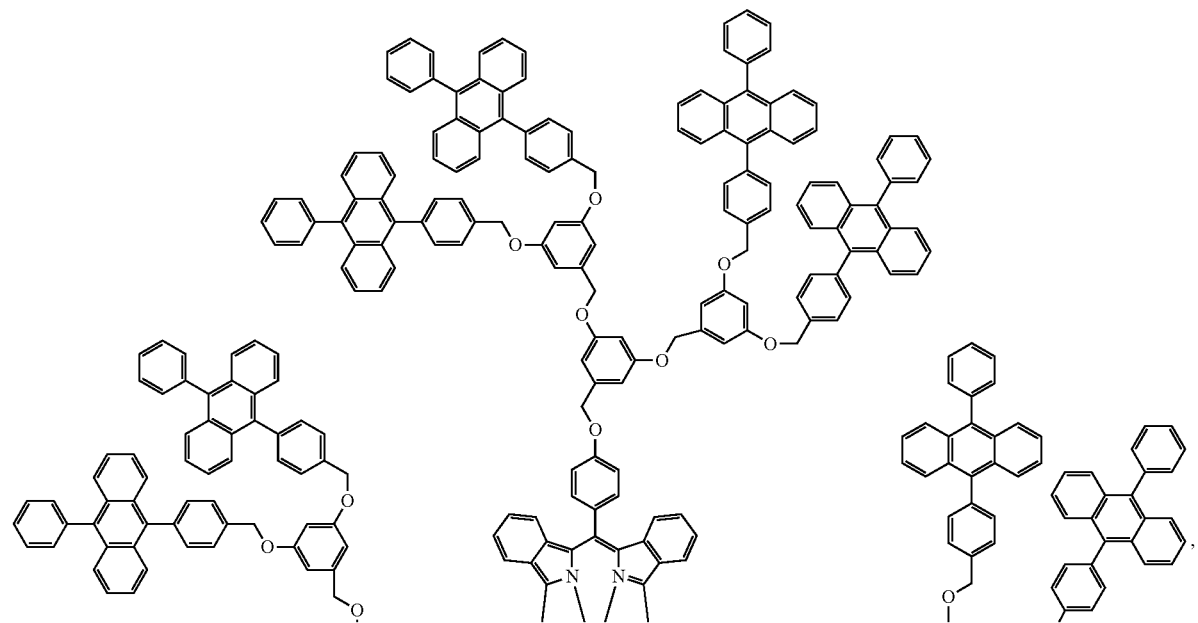

-continued
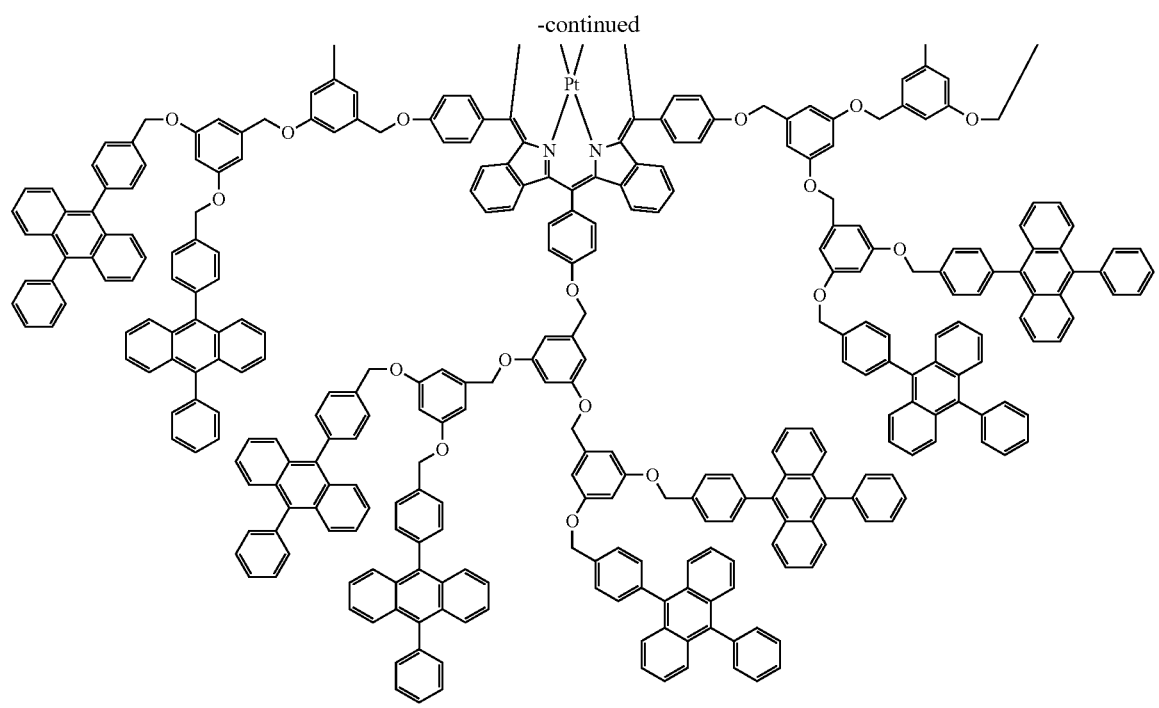
Compound 10
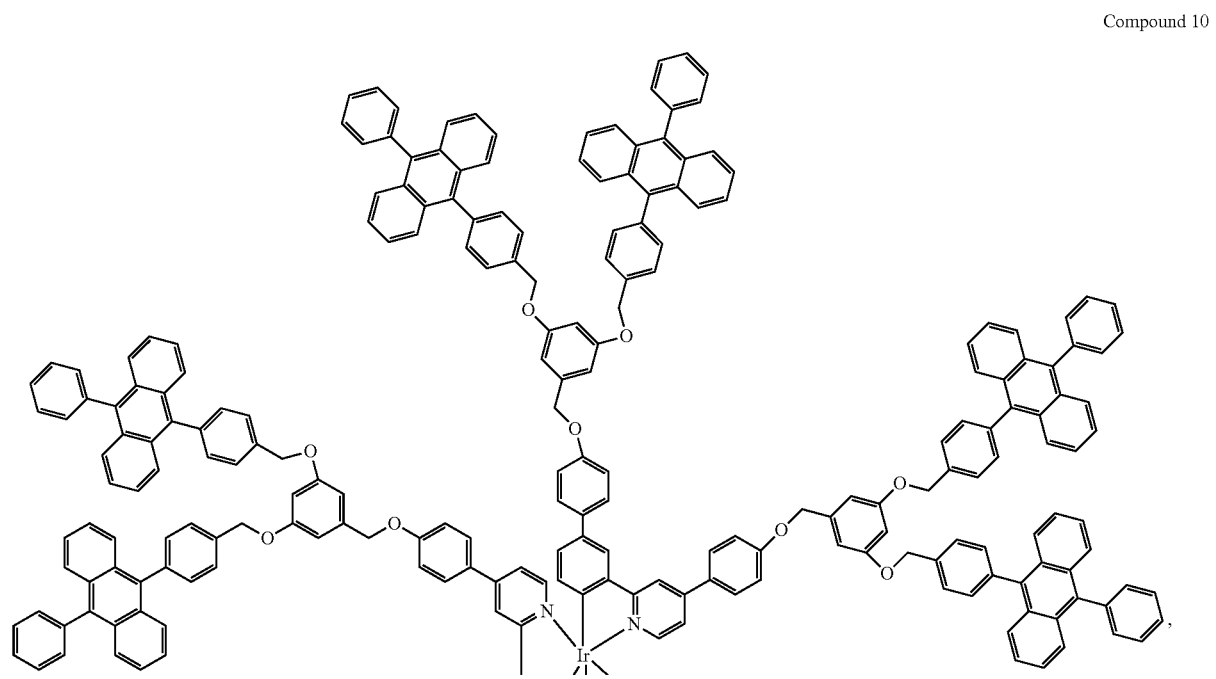

-continued
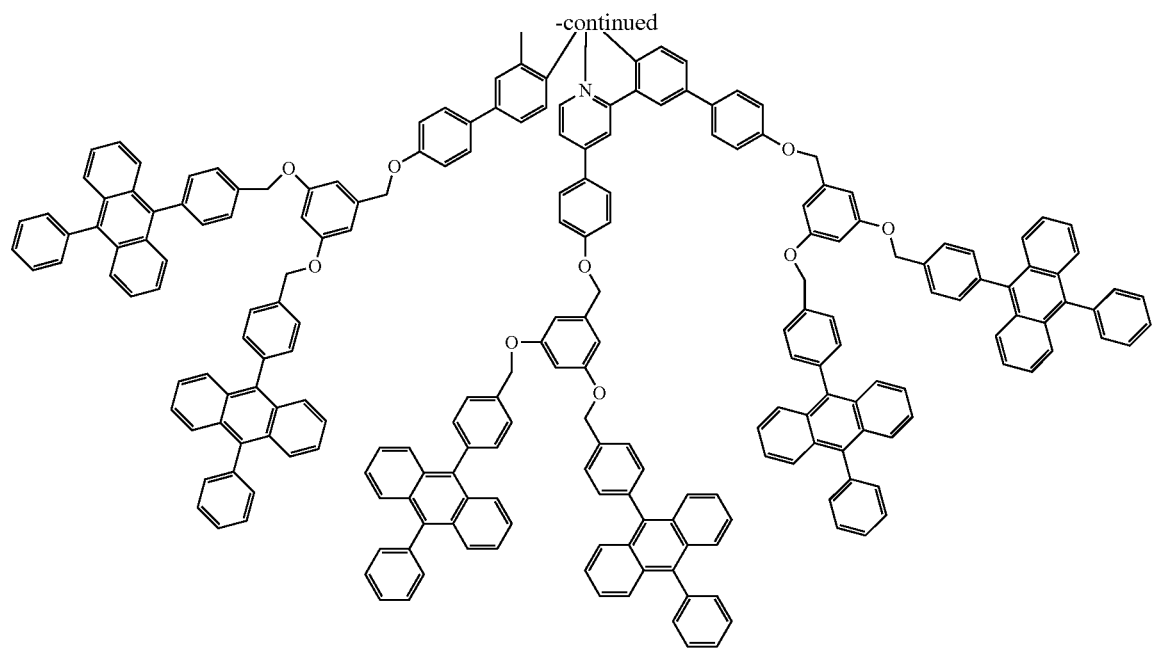
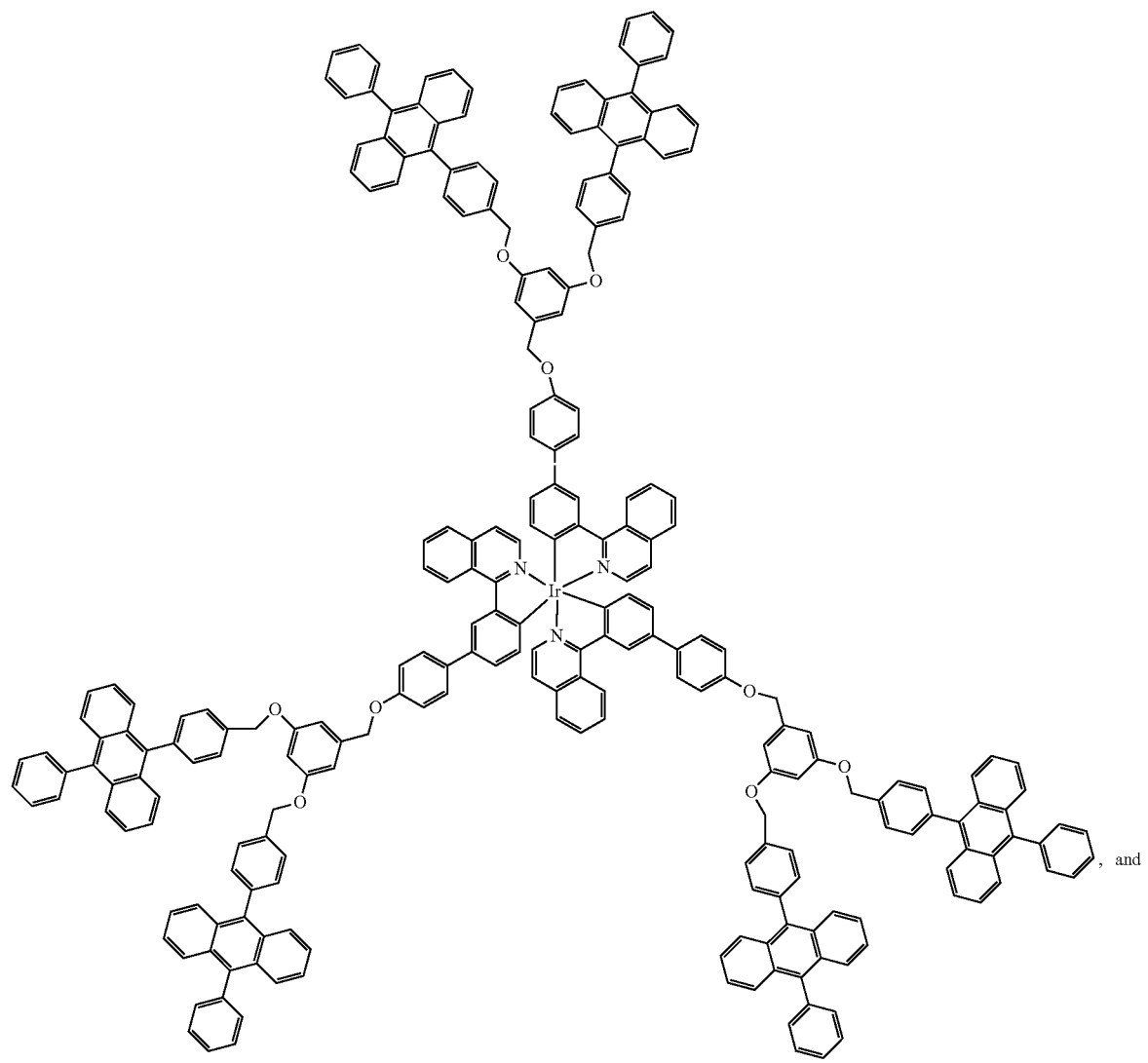
Compound 11
, and

-continued

Compound 12

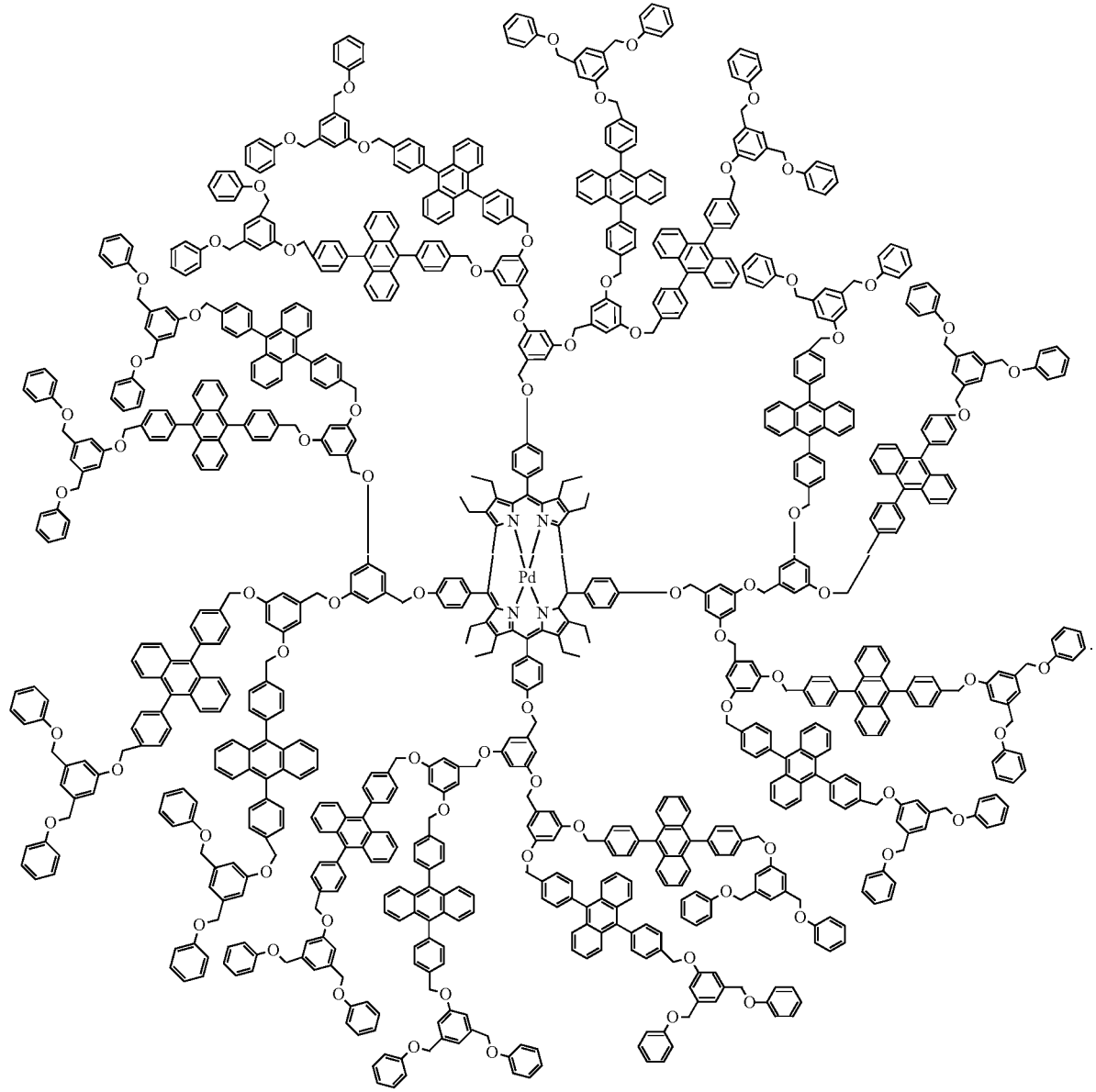

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
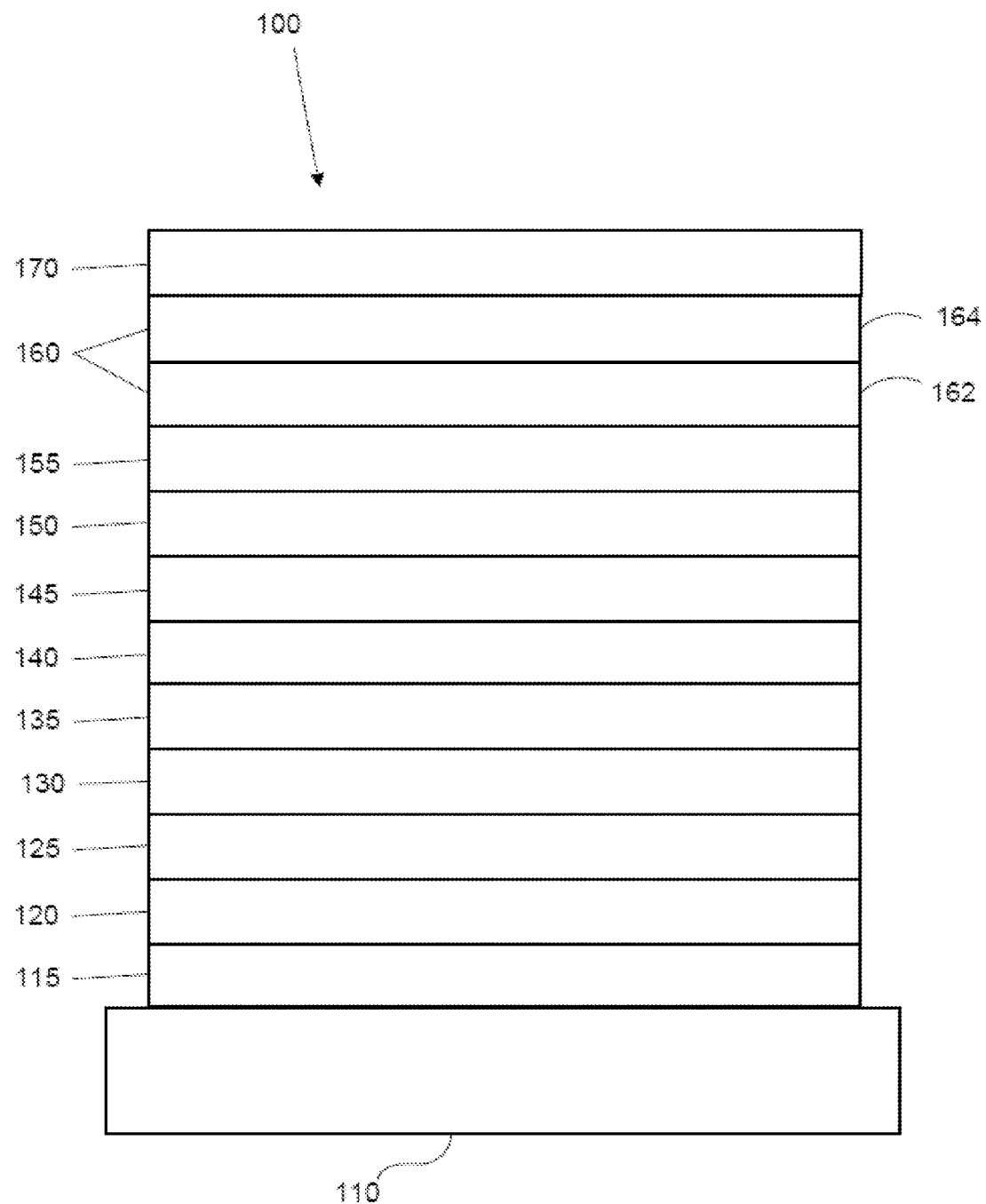
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
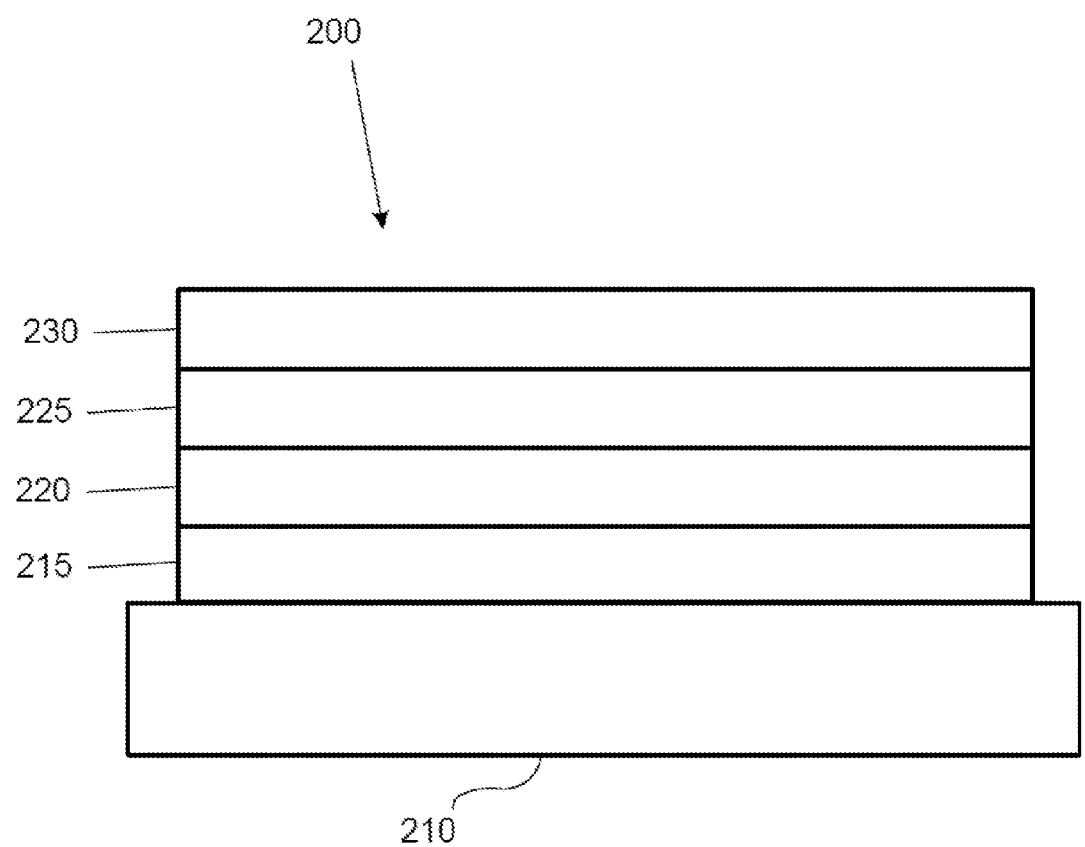
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

In general, photon up conversion based on triplet-triplet annihilation (TTA) is known as a promising wavelength-shifting technology. The sensitized TTA mechanism may allow for the use of low power non-coherent continuous-wave excitation sources. In a sensitized TTA process, short wavelength photons may be produced from the absorption of lower energy light by triplet sensitizers. The sensitizers may first absorb light and convert the singlet excited state to a triplet upon intersystem crossing, and then transfer the energy to the acceptor molecules through triplet-triplet energy transfer. Two triplets from the acceptor may collide and produce a higher energy excited singlet state and the corresponding ground-state species. The excited singlet state may undergo radiative decay, producing a photon that is significantly higher in energy than the exciting light. Additional details regarding the TTA-UC process can be found in US Publication No. 2011/0304263, the disclosure of which is incorporated by reference in its entirety.

A dendritic benzophenone-naphthylene system for TTA-UC has been described in the art. See, Giacomo Bergamini et al., Photochem. Photobiol. Sci., 2004, 3, 898-905. Upon excitation of a benzophenone core at 355 nm, triplet-triplet energy transfer occurred from benzophenone to naphthylene. It was reported that the intra-dendrimer triplet-triplet annihilation of naphthalene excited states lead to delayed naphthalene fluorescence. However, the upconversion was very low and the efficiency was not measured.

Generally, triplet-triplet annihilation up conversion (TTA-UC) has occurred in dilute solutions of sensitizer-emitter pairs. Recently there has been a realization of TTA-UC in solid polymer matrices. The triplet-triplet energy transfer (TTET) between the sensitizer and the emitter is dominated by the Dexter-type energy transfer. For example, if the sensitizer and the emitter are confined within a sphere of a given radius R, the energy transfer may occur at a particular rate. The energy transfer rate may be reduced if the radius R increases beyond a given limit. Therefore, providing translational mobility and maximizing the concentrations of the sensitizer and the emitter, wherein the average distance between the sensitizer and the emitter is within the R limit, may improve the energy transfer process. However, a high sensitizer concentration may lead to increased back energy transfer from the emitter to the sensitizer, resulting in a decrease in TTA-UC efficiency. Thus, to design improved high efficiency TTA-UC systems, it may be advantageous to provide a relatively low sensitizer concentration such that the absorption of the sensitizer from the emission by the emitter is low in order to minimize reabsorption. Additionally, the optical density of the sensitizer at the incident light may need to be sufficiently high to harvest incident light, and the mobility of emitter may need to be high to generate triplet-triplet annihilation.

Figure 3:
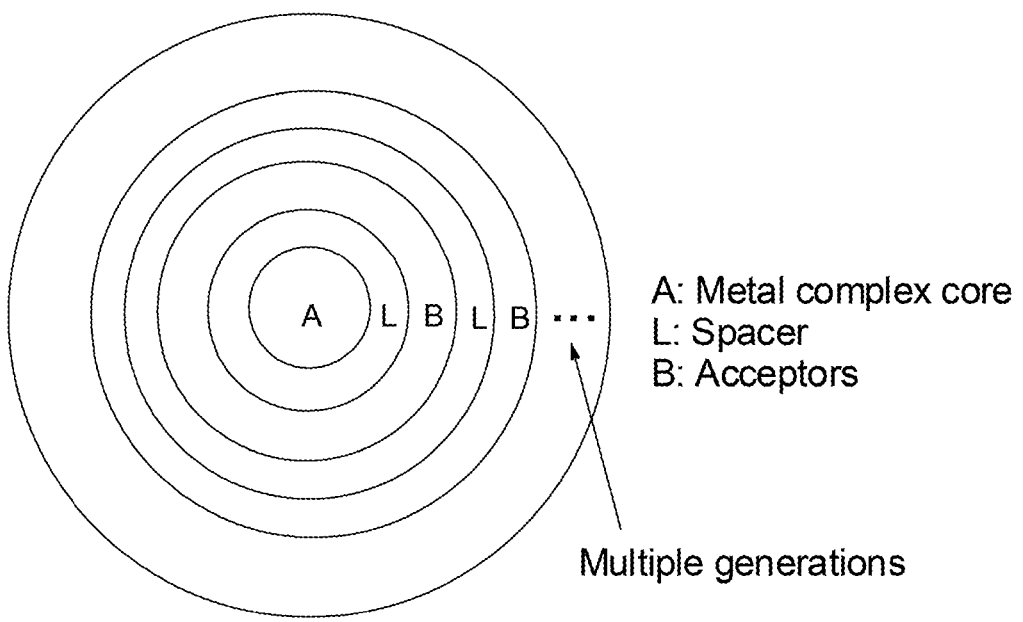
FIG. 3 shows a schematic drawing of a dendritic TTA-UC system.

FIG. 3 shows a schematic diagram of a dendritic system for TTA-UC according to an embodiment of the invention. Specifically, the core of the dendrimer may include a metal complex, wherein fast intersystem crossing may occur to generate triplet states. For example, any metal complex that can effectively undergo fast intersystem crossing may be used as the core. On the peripheral, multiple acceptor moieties are covalently linked to the core through a spacer. In an embodiment, the distance between the metal complex core and the acceptors may be adjusted by the length of the spacer to achieve improved triplet-triplet energy transfer.

In an embodiment, a compound is provided which includes a metal complex sensitizer core, a first acceptor group, and a spacer group between the metal complex core and the acceptor group. The acceptor group may have a triplet energy lower than a triplet energy of the metal complex sensitizer core. In an embodiment, the first spacer group may substantially surround the metal complex sensitizer core. In this regard, the spacer group may be disposed at least partially between the metal complex sensitizer core and the acceptor group. For example, the spacer group may be covalently bound to the metal complex sensitizer core and/or the acceptor group.

In some embodiments, the compound may include additional spacer and acceptor groups. For example, the compound may include a second spacer group, which also may substantially surround the acceptor group. In this regard, the compound may also include a second acceptor group that substantially surrounds the second spacer group.

As used herein, one group may be said to "substantially surround" another when it is isolated by the other group. For example, the metal complex sensitizer core and/or the acceptor group may be isolated by the spacer group, such that the spacer group prevents the metal complex sensitizer core and/or the acceptor group from contacting adjacent molecules.

Additionally, compounds for triplet-triplet annihilation upconversion are provided. The compounds have the following general structure:

$$A\!-\!(L_1\!-\!(B_1)_{\overline{m_1}}\cdots\!-\!L_x\!-\!(B_x)_{\overline{m_x}})_{\overline{n}}$$

wherein A is a metal complex, $L_1$ to $Lx$ is a spacer group, $B_1$ to $Bx$ is an acceptor group B, $m_1$ is greater than 0, $m_x$ is equal to or greater than 0, n is greater than 0, and acceptor group B has a triplet energy lower than a triplet energy of the metal complex.

Specifically, the metal complex may be any metal complex that can effectively undergo fast intersystem crossing, such as a neutral or ionic iridium complex, an osmium complex, a platinum complex, a palladium complex, a rhenium complex, a ruthenium complex, and a gold complex. Further, n may be in the range of 1 to 20. In particular, examples of the metal complex may include portions of the compounds shown in Table 1 below.

TABLE 1

| Example metal complexes | | |
|---|---|---|
| Heavy metal porphyrins (e.g., Pt or Pd) | 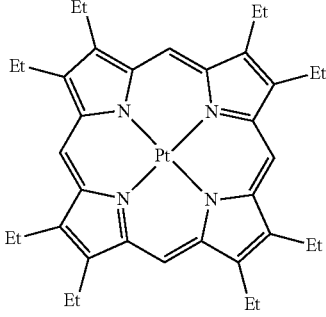 | Nature 395, 151 (1998) |
| | 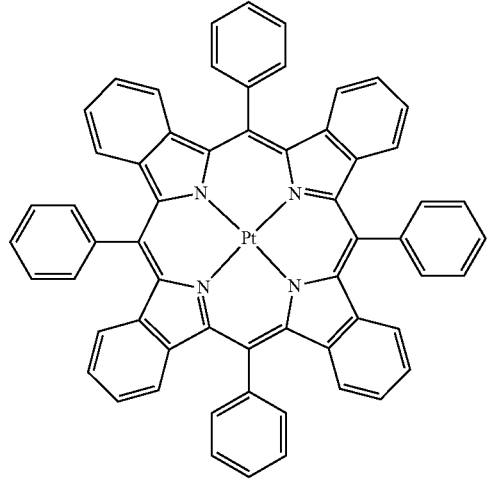 | *Inorg. Chem.* 2009, 48, 2541-2548 |
| | 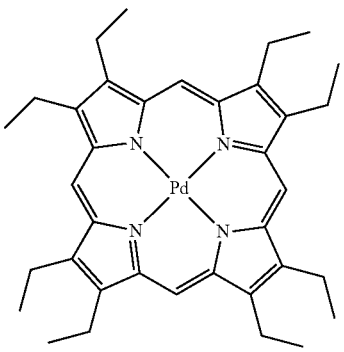 | *J. Am. Chem. Soc.* 2007, 129, 12652-12653 |

TABLE 1-continued
Example metal complexes
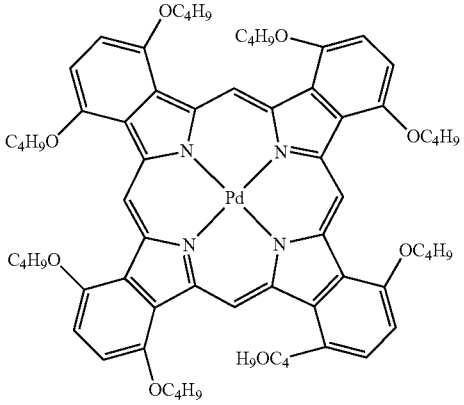
J. Phys. Chem. A 2008, 112, 3550-3556
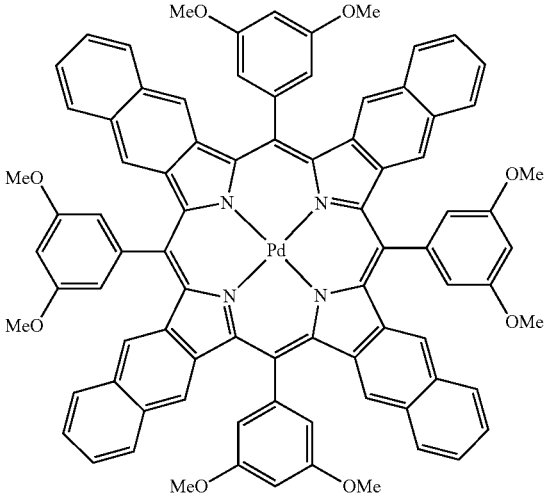
Angew. Chem. Int. Ed. 2007, 46, 7693-7696
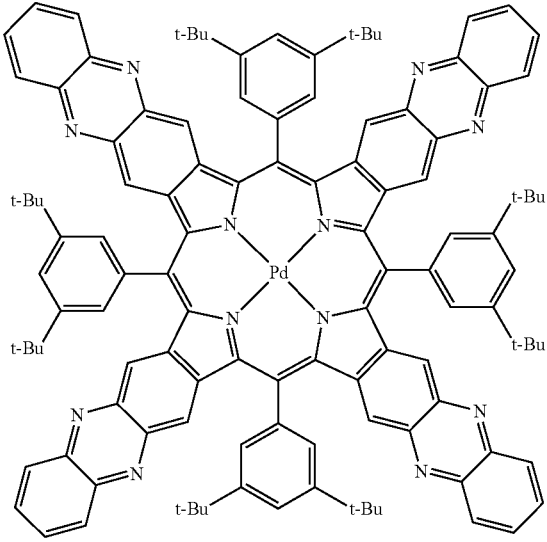
J. Phys. Chem. Lett. 2010, 1, 1795-1799

TABLE 1-continued
Example metal complexes
| | | |
|---|---|---|
| Platinum(II) organometallic complexes | 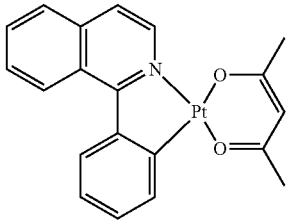 | WO2003040257 |
| | 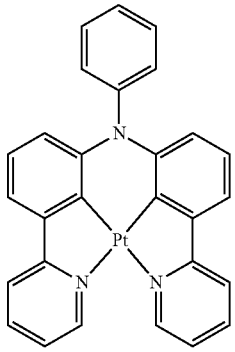 | US20070103060 |
| Pt(II) organometallic complexes, including polydentated ligands | 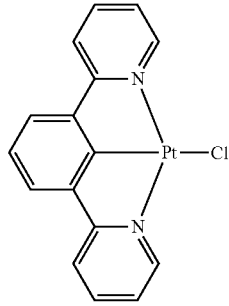 | Appl. Phys. Lett. 86, 153505 (2005) |
| | 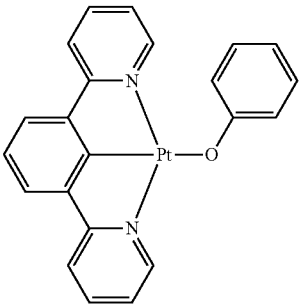 | Appl. Phys. Lett. 86, 153505 (2005) |
| | 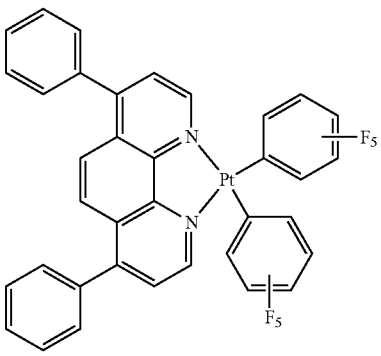 | Chem. Lett. 34, 592 (2005) |

TABLE 1-continued
Example metal complexes
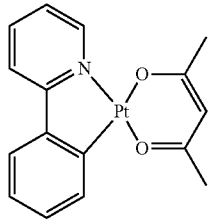
WO2002015645
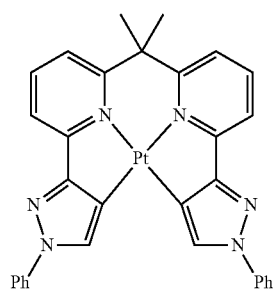
US20060263635
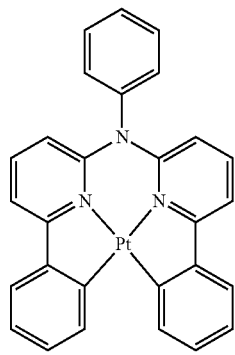
US20060182992
US20070103060
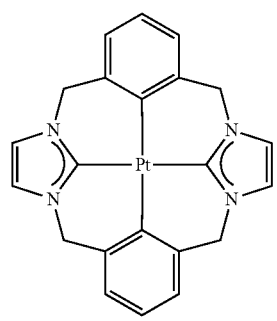
U.S. Pat. No. 7,655,323
Iridium(III) organometallic complexes
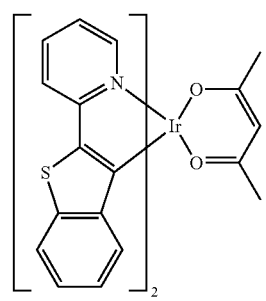
Appl. Phys. Lett. 78, 1622 (2001)

TABLE 1-continued
Example metal complexes
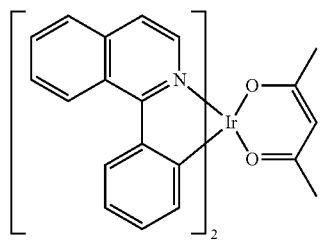 US2006835469
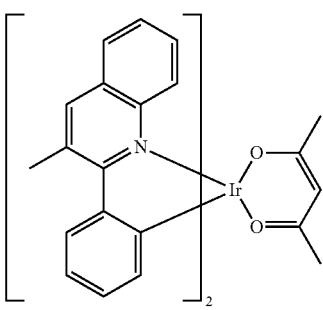 US2006835469
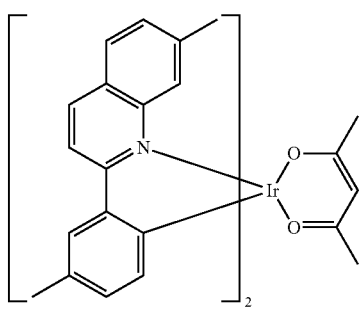 US20060202194
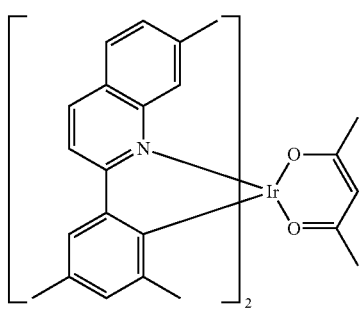 US20060202194
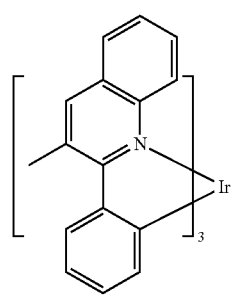 US20070087321

TABLE 1-continued
| Example metal complexes | |
|---|---|
| 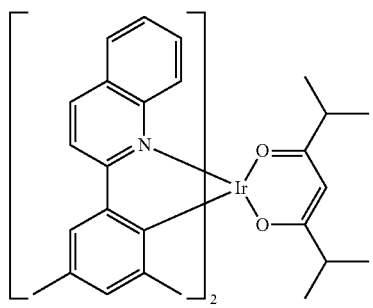 | US20080261076<br>US20100090591 |
| 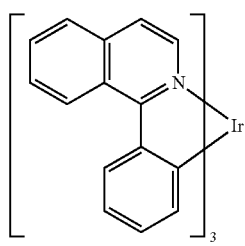 | US20070087321 |
| 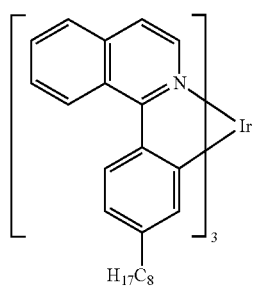 | Adv. Mater. 19, 739 (2007) |
| 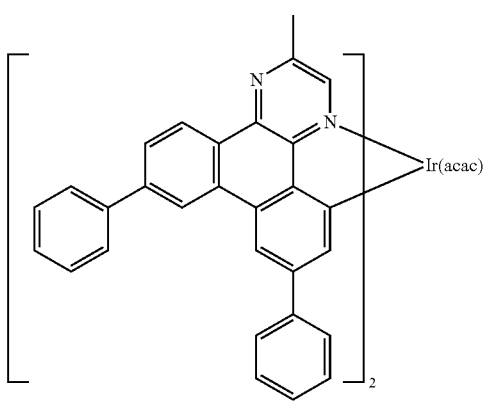 | WO2009100991 |
| 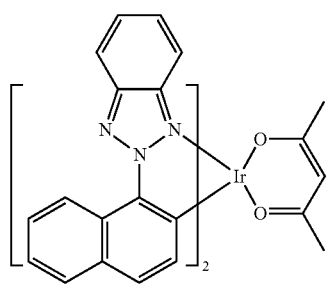 | WO2008101842 |

TABLE 1-continued
Example metal complexes
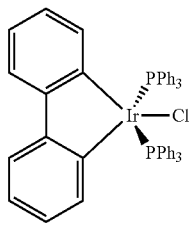
U.S. Pat. No. 7,232,618
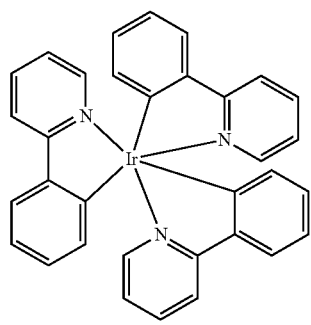
and its derivatives
Inorg. Chem. 40, 1704 (2001)
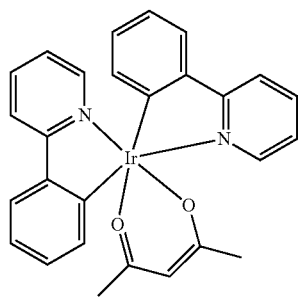
US20020034656
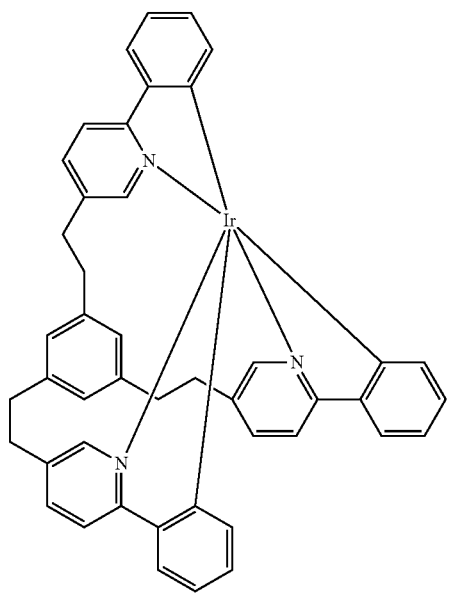
U.S. Pat. No. 7,332,232

TABLE 1-continued
Example metal complexes
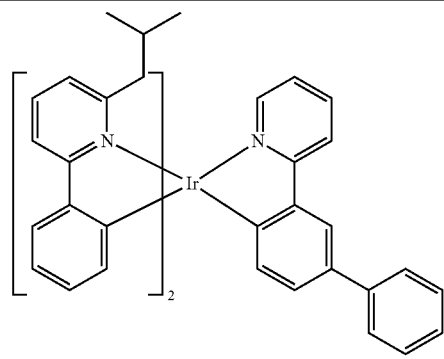
US20090108737
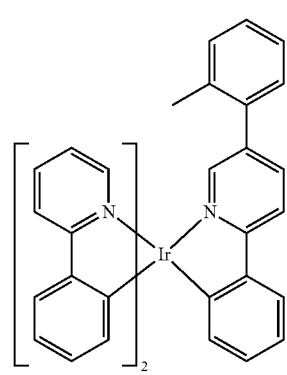
WO2010028151
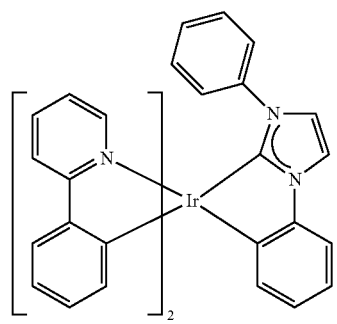
EP1841834B
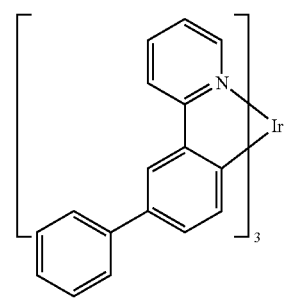
US20060127696
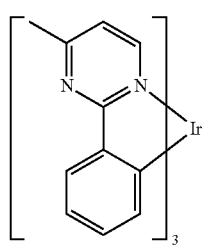
US20090039776

TABLE 1-continued
Example metal complexes
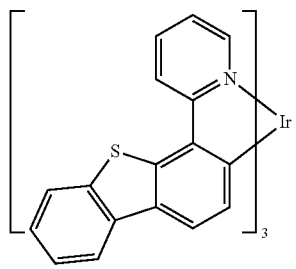
U.S. Pat. No. 6,921,915
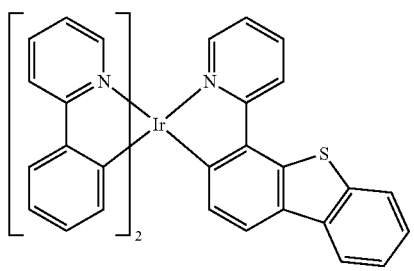
US20100244004
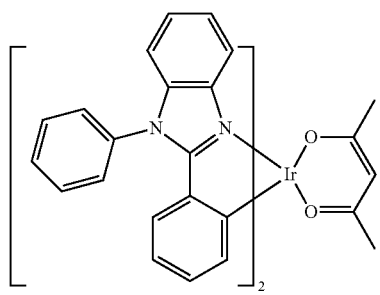
U.S. Pat. No. 6,687,266
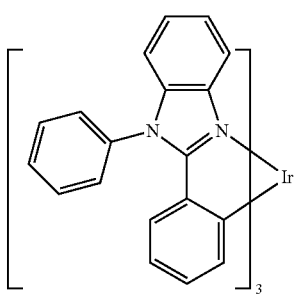
Chem. Mater. 16, 2480 (2004)
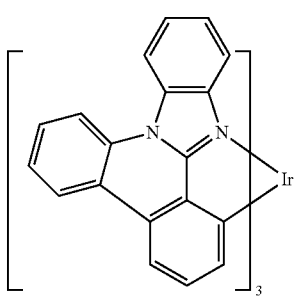
US20070190359

TABLE 1-continued
Example metal complexes
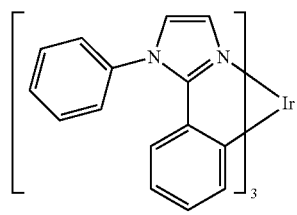 US 20060008670
JP2007123392
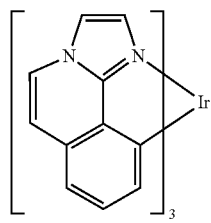 WO2010086089,
WO2011044988
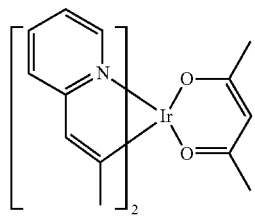 Adv. Mater. 16,
2003 (2004)
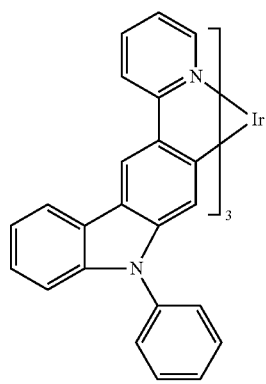 Angew. Chem. Int.
Ed. 2006, 45,
7800
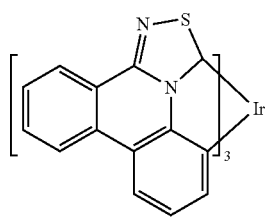 WO2009050290
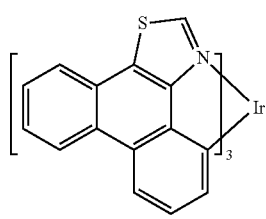 US20090165846

TABLE 1-continued
Example metal complexes
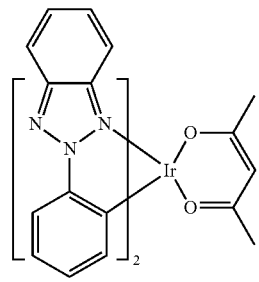 US20080015355
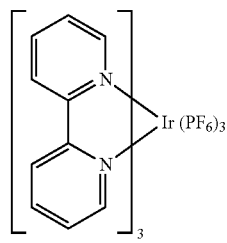 US20010015432
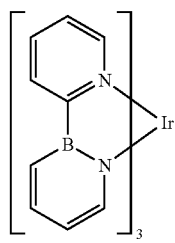 US20100295032
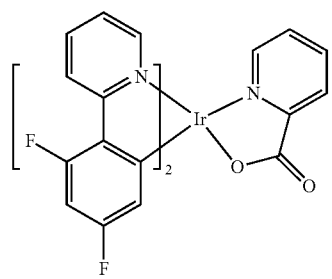 WO2002002714
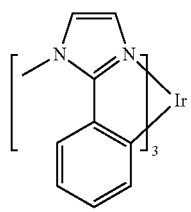 WO2006009024
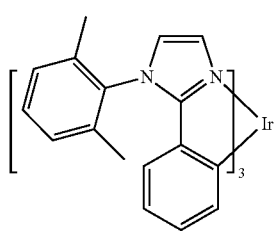 US20060251923
US20110057559
US20110204333

TABLE 1-continued
Example metal complexes
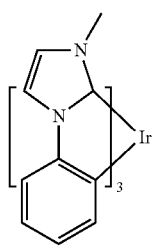
U.S. Pat. No. 7,393,599,
WO2006056418,
US20050260441,
WO2005019373
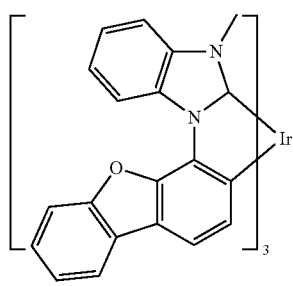
U.S. Pat. No. 7,534,505
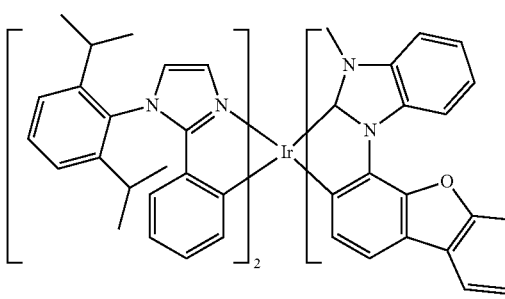
WO2011051404
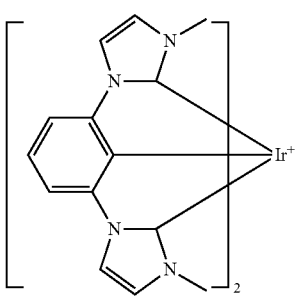
U.S. Pat. No. 7,445,855
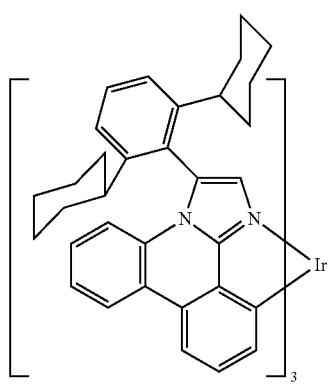
US20070190359,
US20080297033
US20100148663

TABLE 1-continued
Example metal complexes
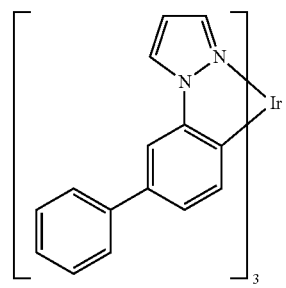
U.S. Pat. No. 7,338,722
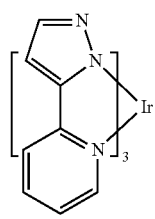
US20020134984
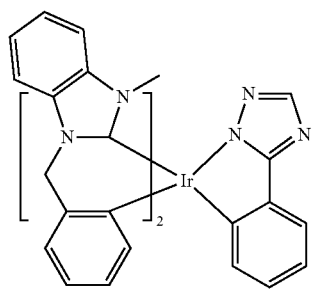
Angew. Chem. Int. Ed. 47, 1 (2008)
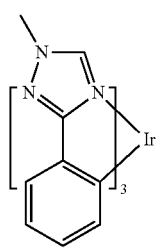
Chem. Mater. 18, 5119 (2006)
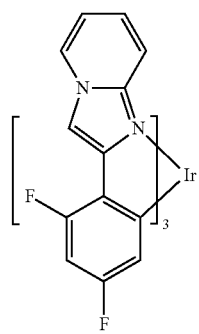
Inorg. Chem. 46, 4308 (2007)

TABLE 1-continued
Example metal complexes
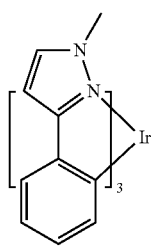 WO2005123873
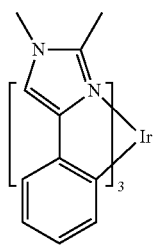 WO2005123873
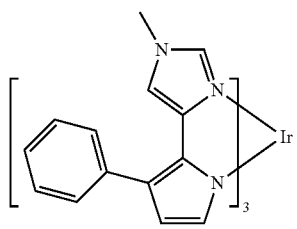 WO2007004380
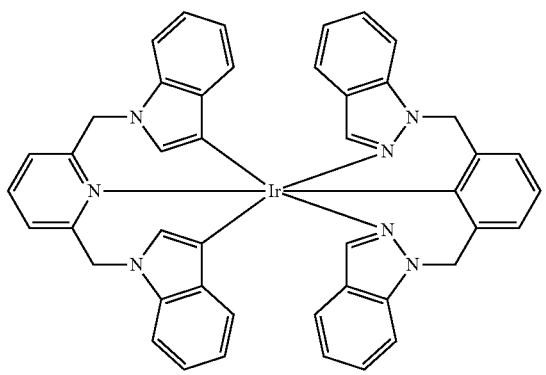 WO2006082742
Osmium(II) complexes 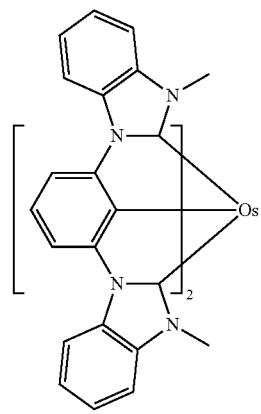 U.S. Pat. No. 7,279,704

TABLE 1-continued
Example metal complexes
| | | |
|---|---|---|
| | 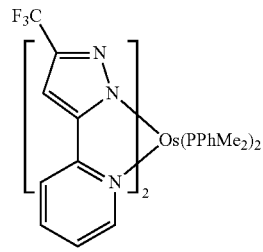 | Chem. Mater. 17, 3532 (2005) |
| | 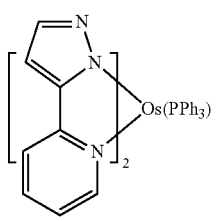 | Organometallics 23, 3745 (2004) |
| Ruthenium(II) complexes | 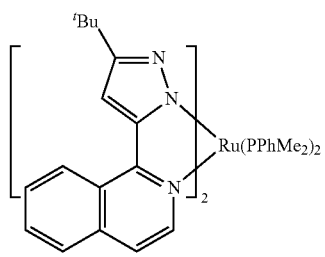 | Adv. Mater. 17, 1059 (2005) |
| Rhenium (I), (II), and (III) complexes | 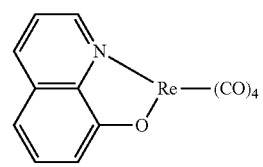 | US20050244673 |

TABLE 1-continued
Example metal complexes
| | | |
|---|---|---|
| Rhenium(III) complexes | 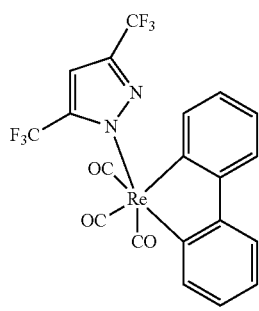 | Inorg. Chem. 42, 1248 (2003) |
| Gold complexes | 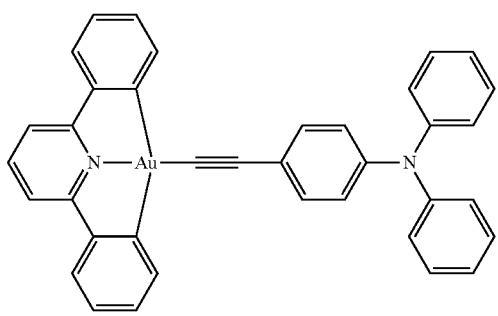 | Chem. Commun. 2906 (2005) |
| Organometallic complexes with two or more metal centers | 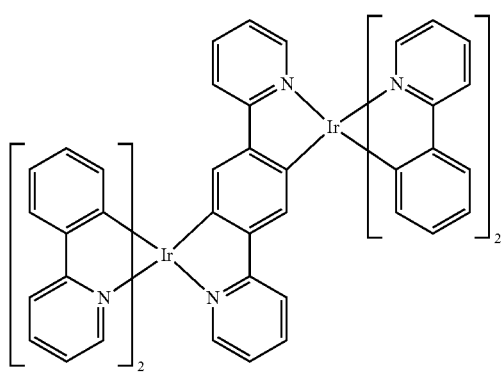 | US20030152802 |

The acceptor group B may be a fused aromatic group, for example, the acceptor group B may include polycyclic aromatic compounds such as compounds containing naphthalene, anthracene, tetracene, pyrene, chrysene, and perylene. Additionally, $m_1$ may be in the range of 1 to 20 and $m_x$ may be in the range of 0 to 20. The ratio of the acceptor group B to the metal complex A may be at least 4. Examples of the acceptor group may include:

TABLE 2

Example acceptor groups

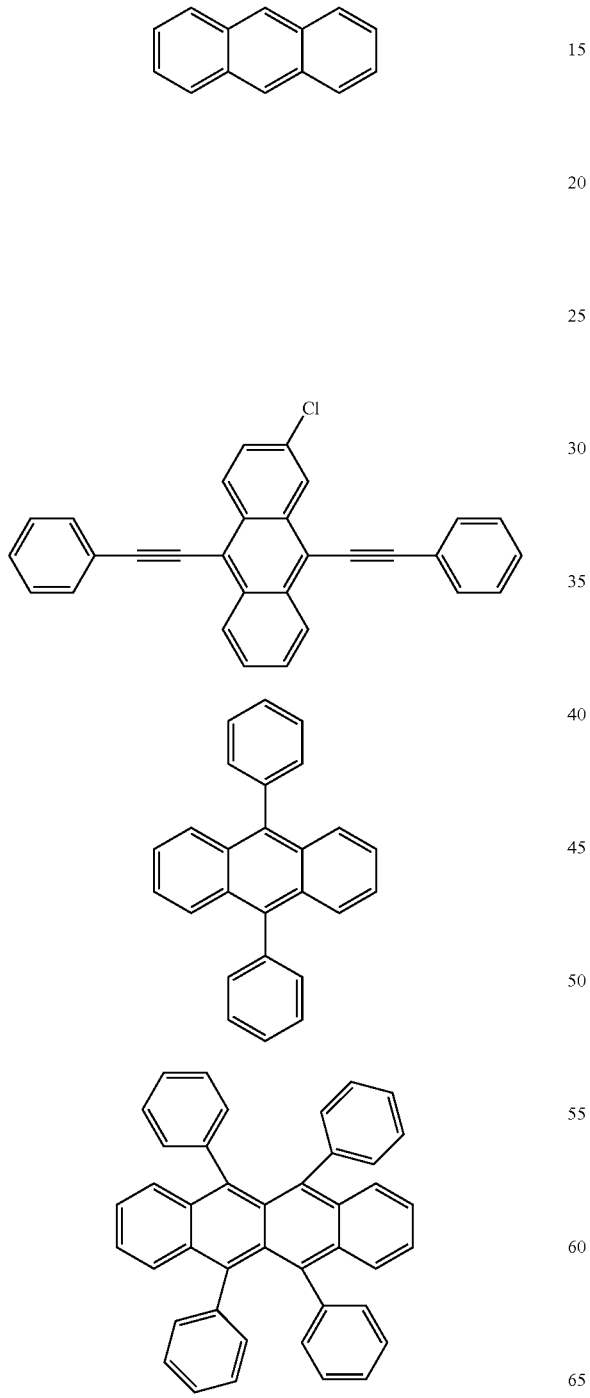

TABLE 2-continued

Example acceptor groups

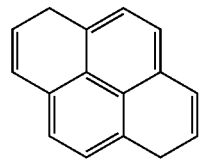 [SMILES: C1=Cc2ccc3c4c(ccc(c24)C1)C=CC3]

The spacer group may include an alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, ester, and combinations thereof. Additionally, the distance between the metal complex core and the acceptor group(s) may be based on the length of the spacer, and may result in improved triplet-triplet energy transfer.

In an embodiment, examples of the compounds described herein may include but are not limited to the following as shown in the following Table:

TABLE 3
Example Compounds
Compound 1
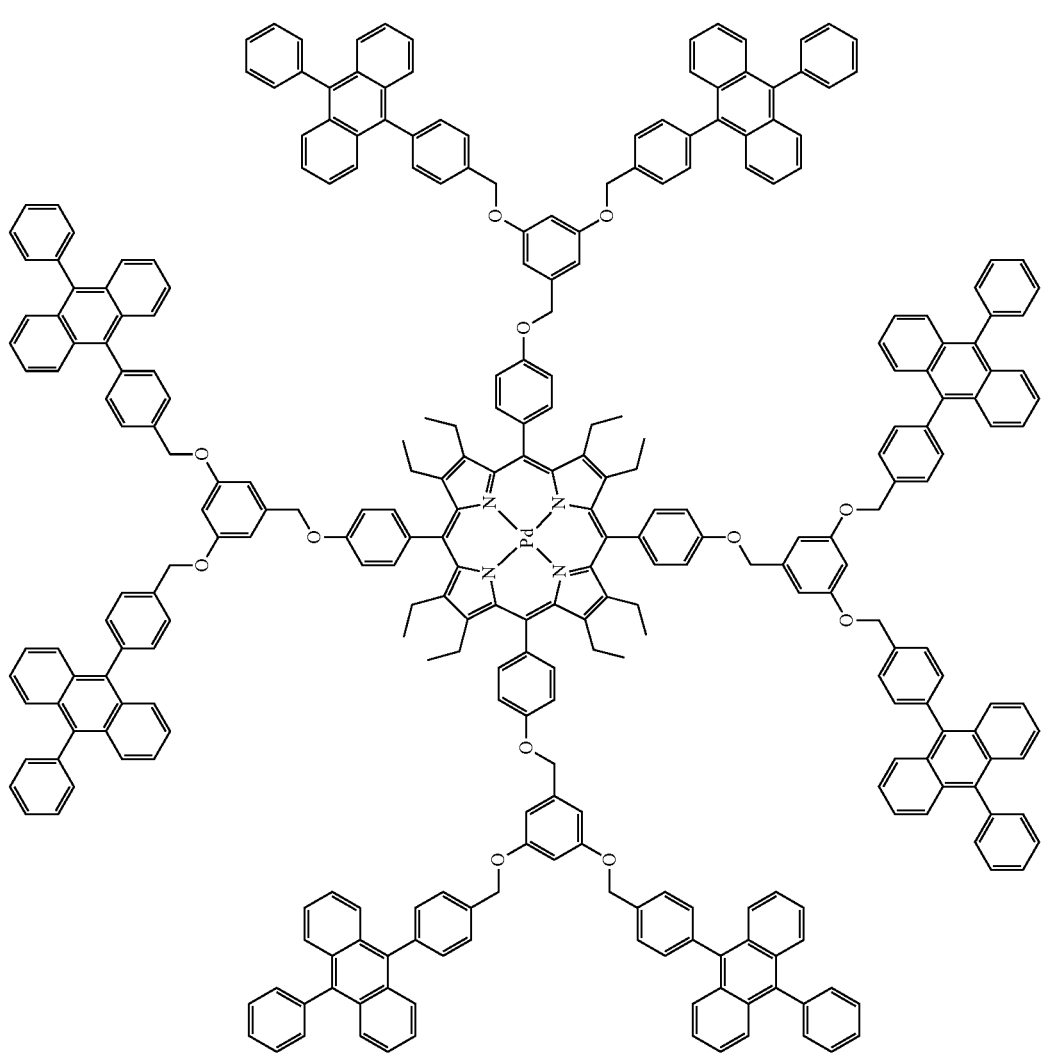

TABLE 3-continued
Example Compounds
Compound 2
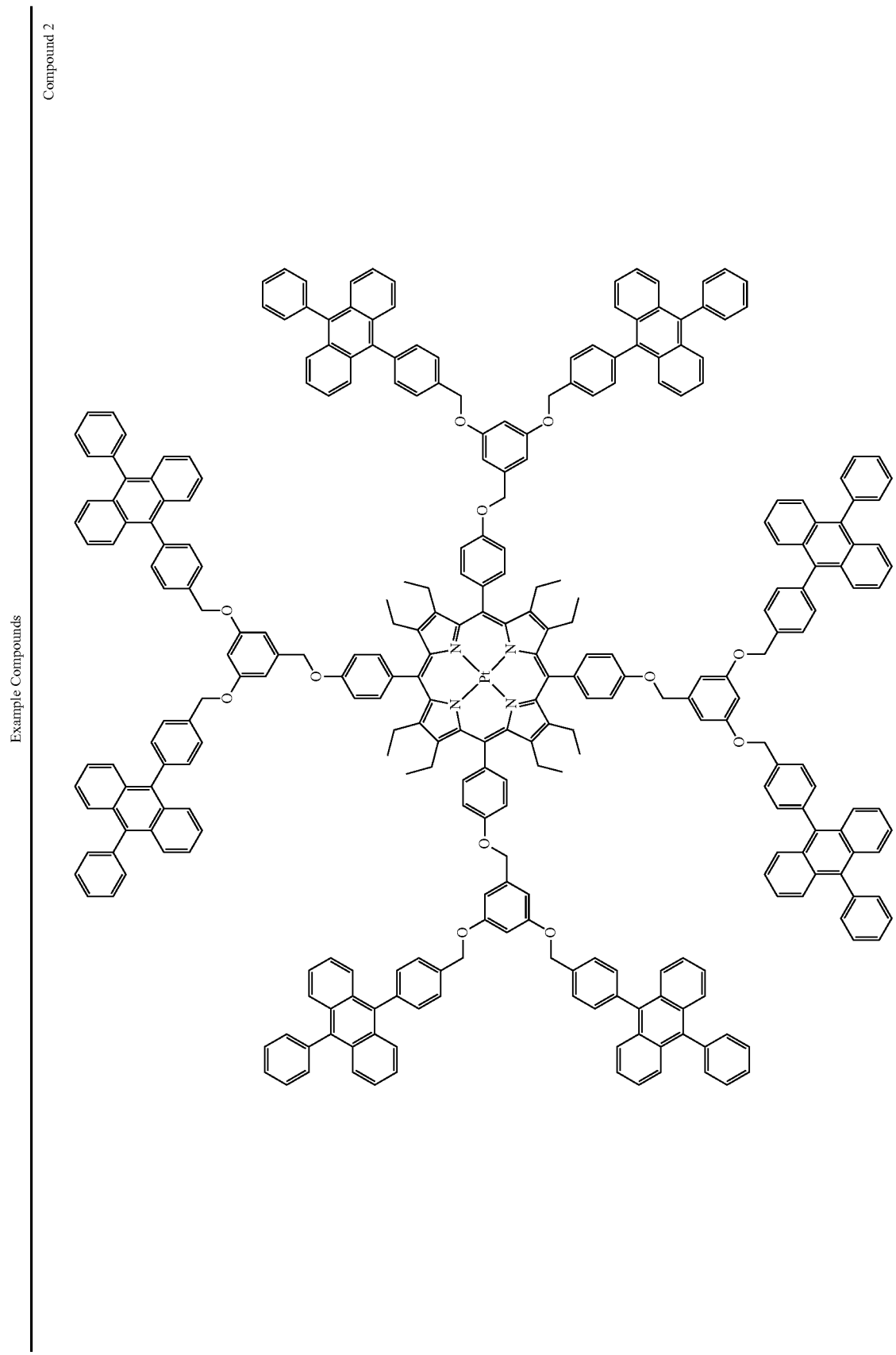

TABLE 3-continued
Example Compounds
Compound 3
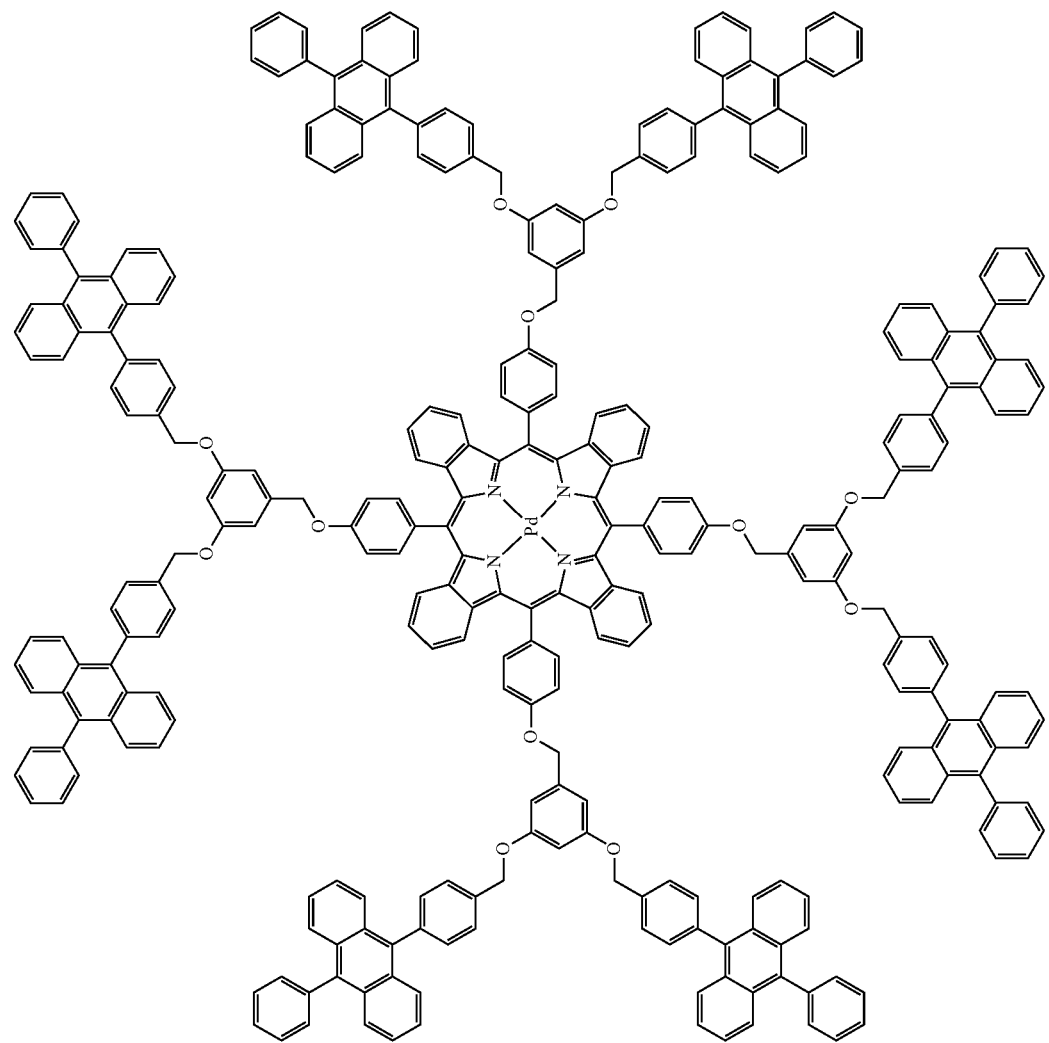

TABLE 3-continued
Example Compounds
Compound 4
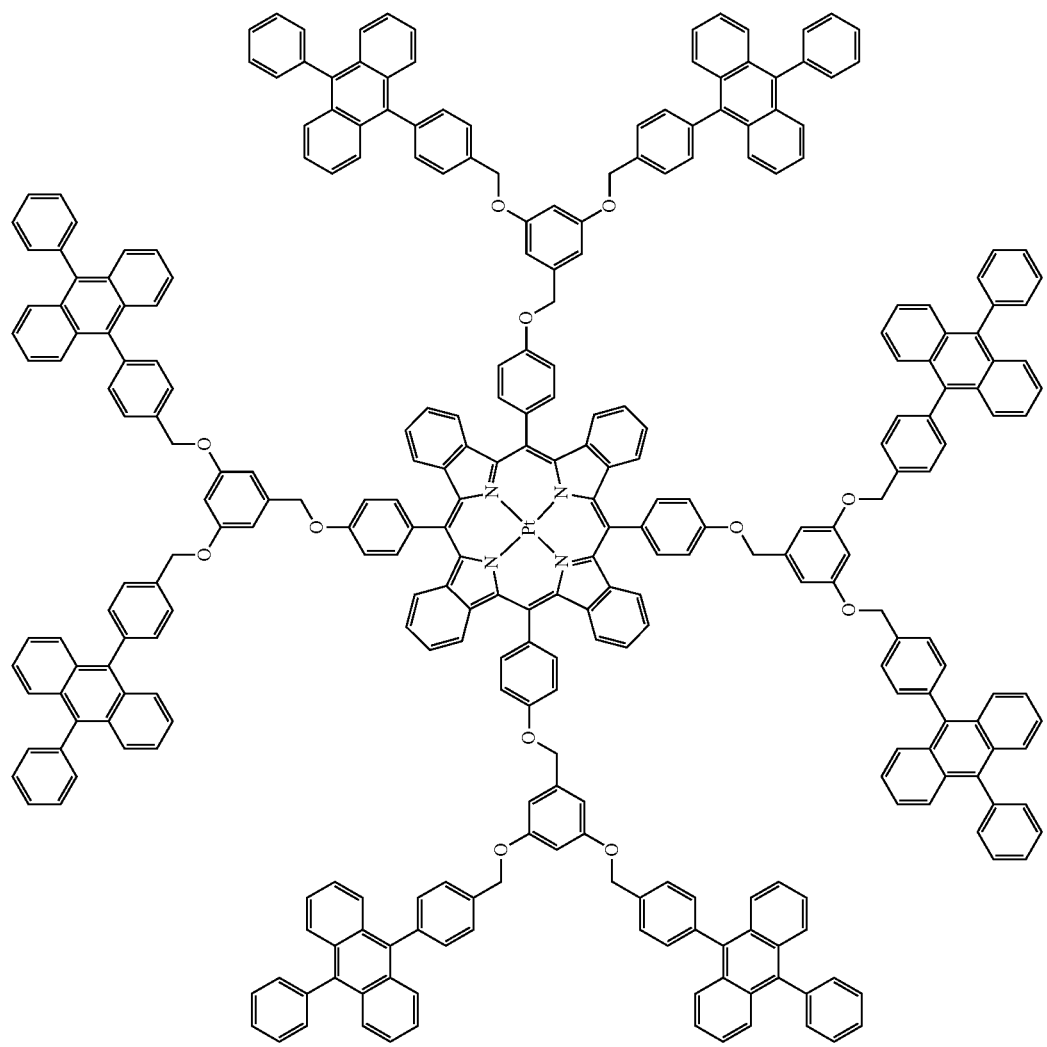

TABLE 3-continued
Example Compounds
Compound 5
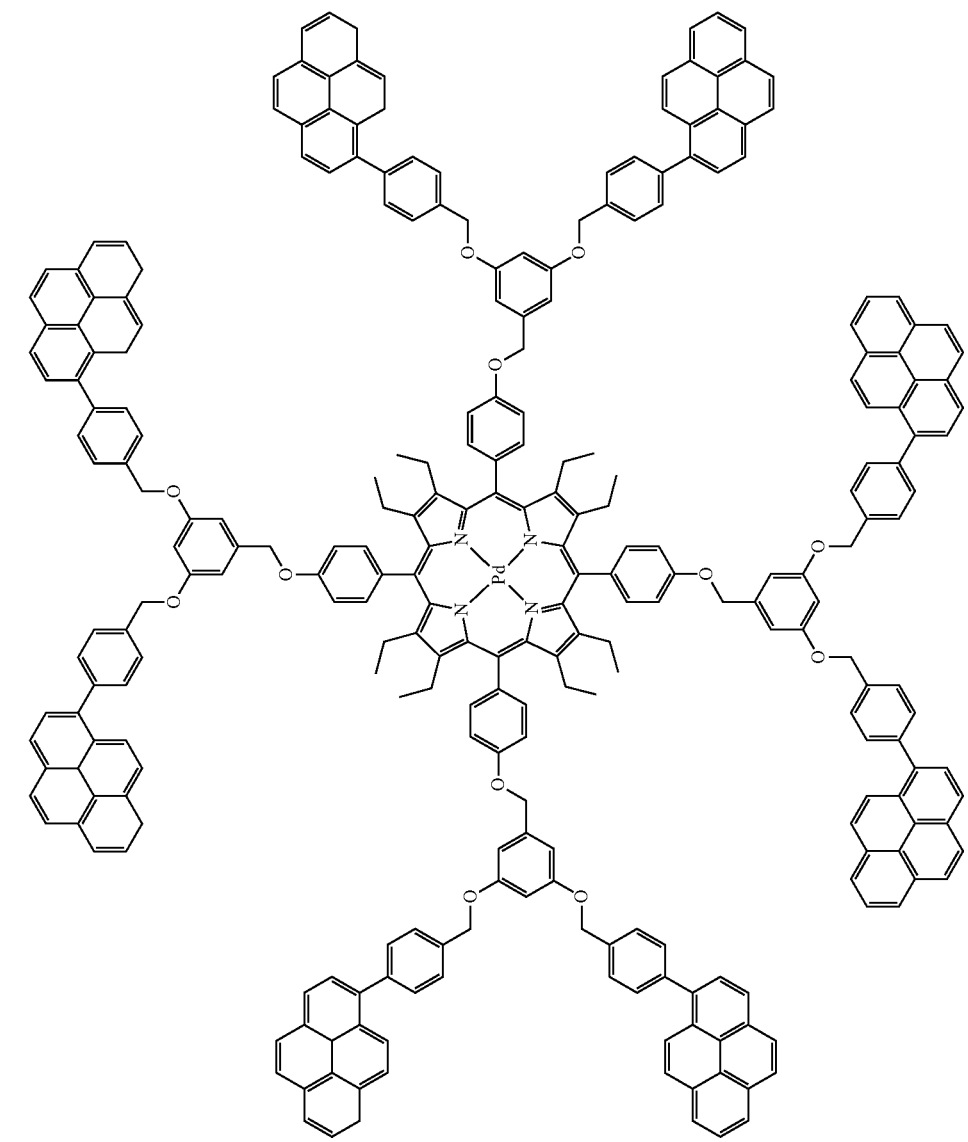

TABLE 3-continued
Example Compounds
Compound 6
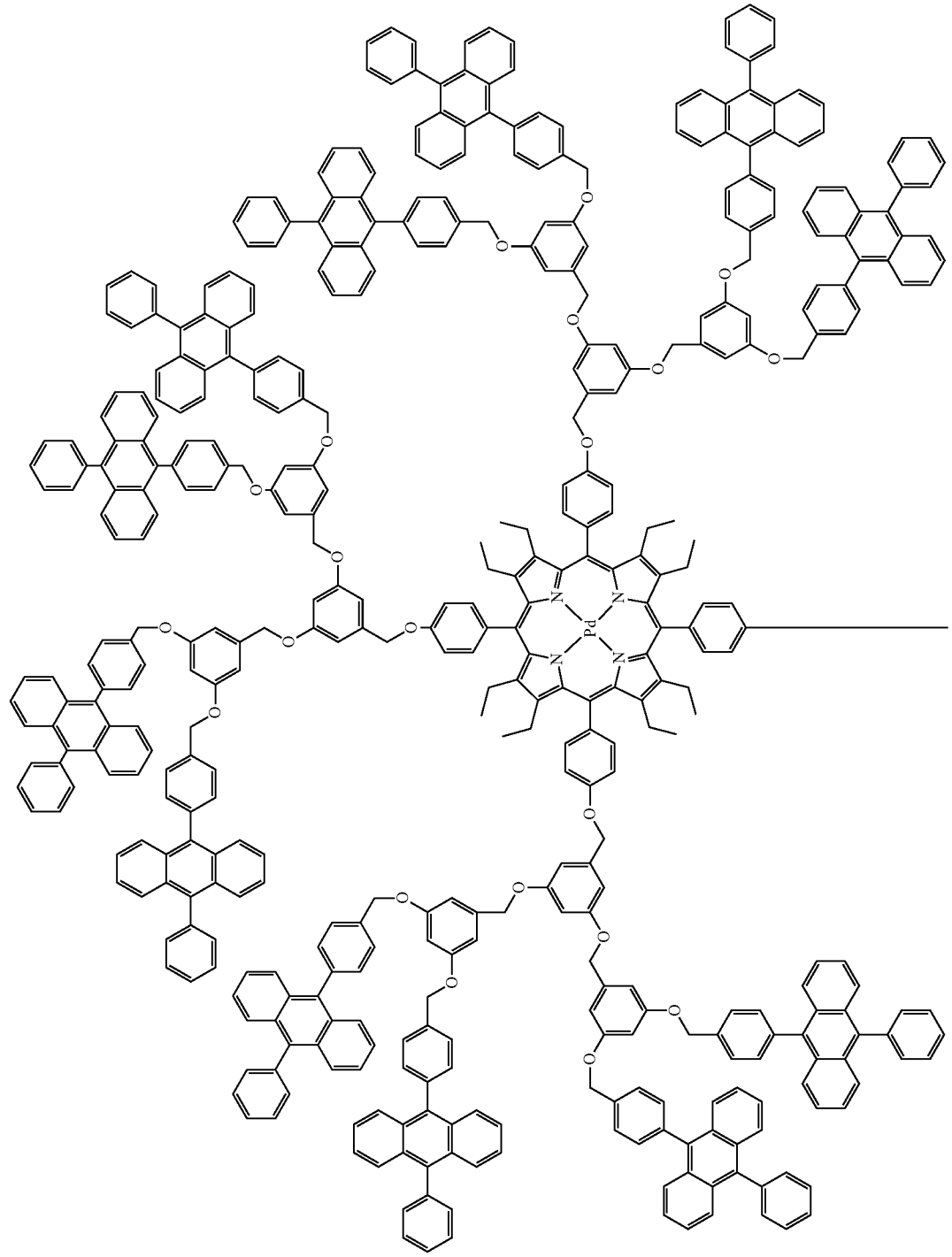

TABLE 3-continued
Example Compounds
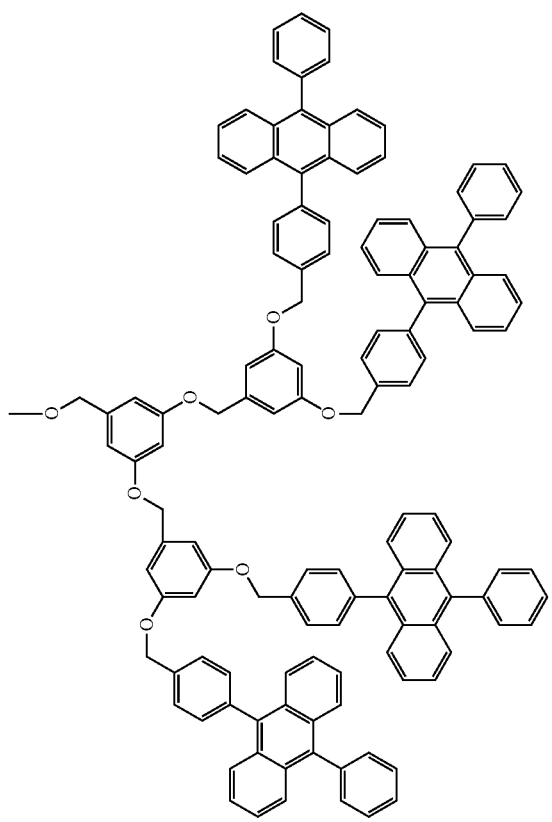

TABLE 3-continued
Example Compounds
Compound 7
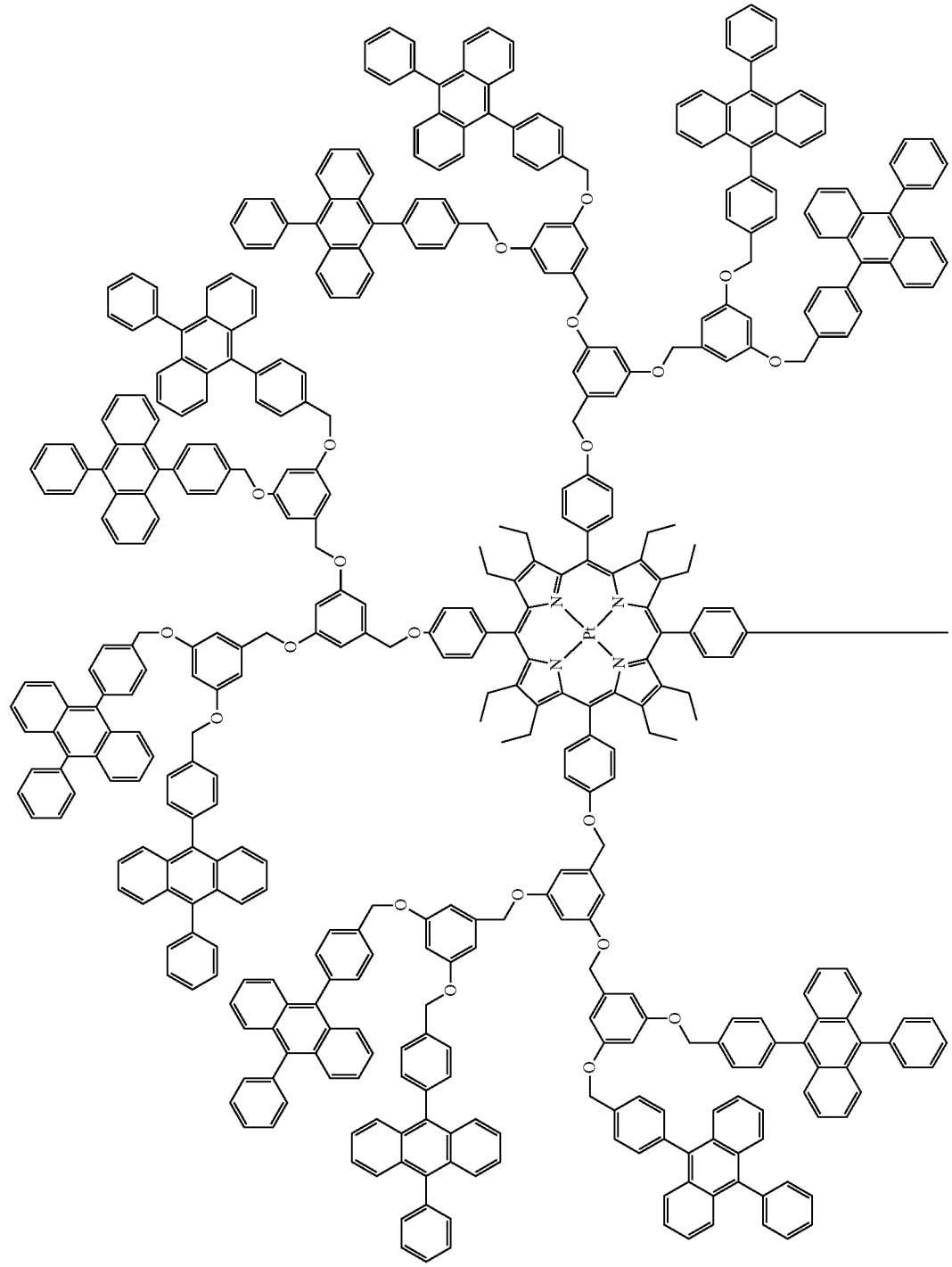

TABLE 3-continued
Example Compounds
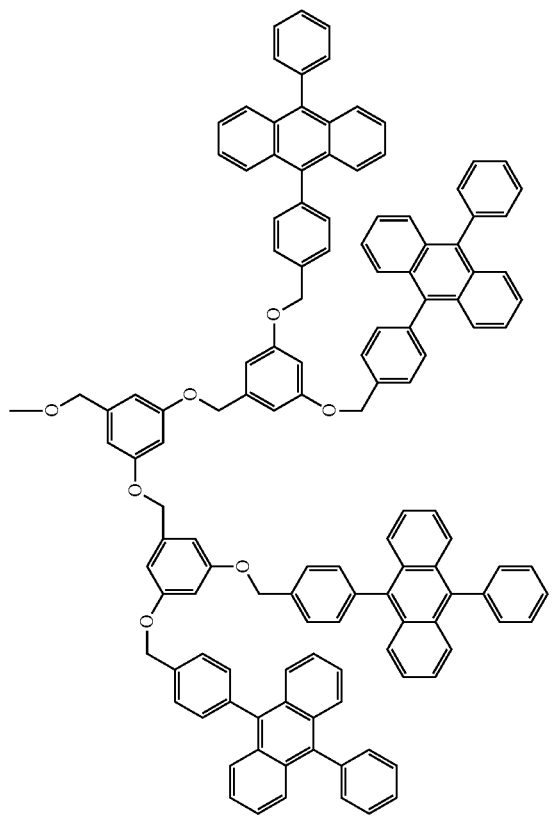

TABLE 3-continued
Example Compounds
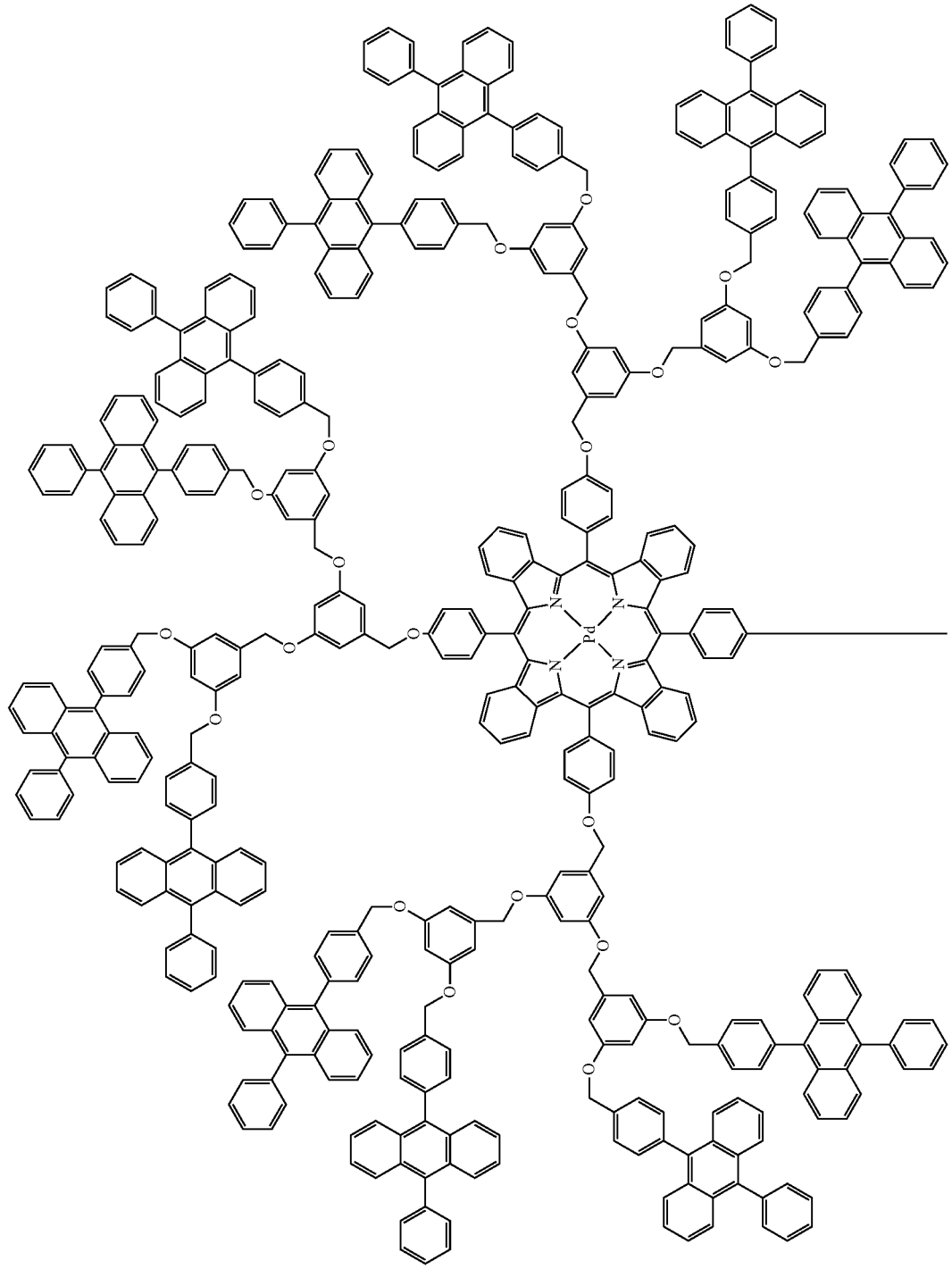
Compound 8

TABLE 3-continued
Example Compounds
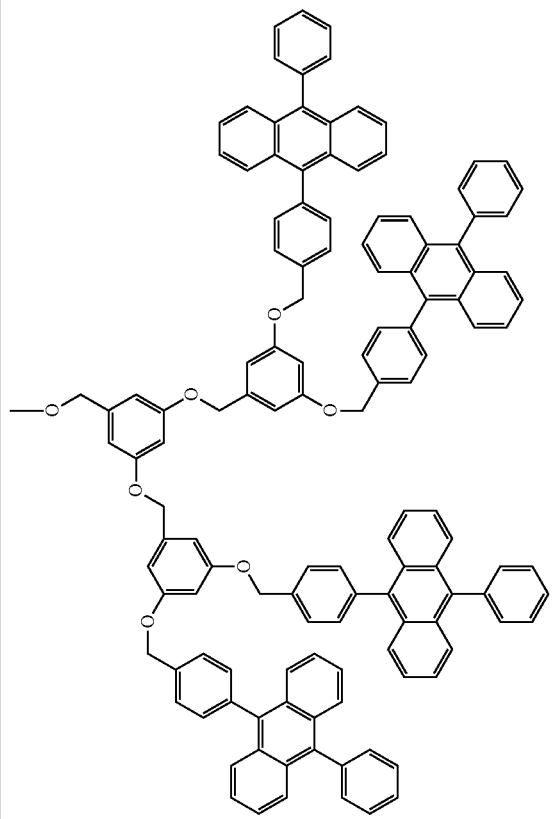

TABLE 3-continued
Example Compounds
Compound 9
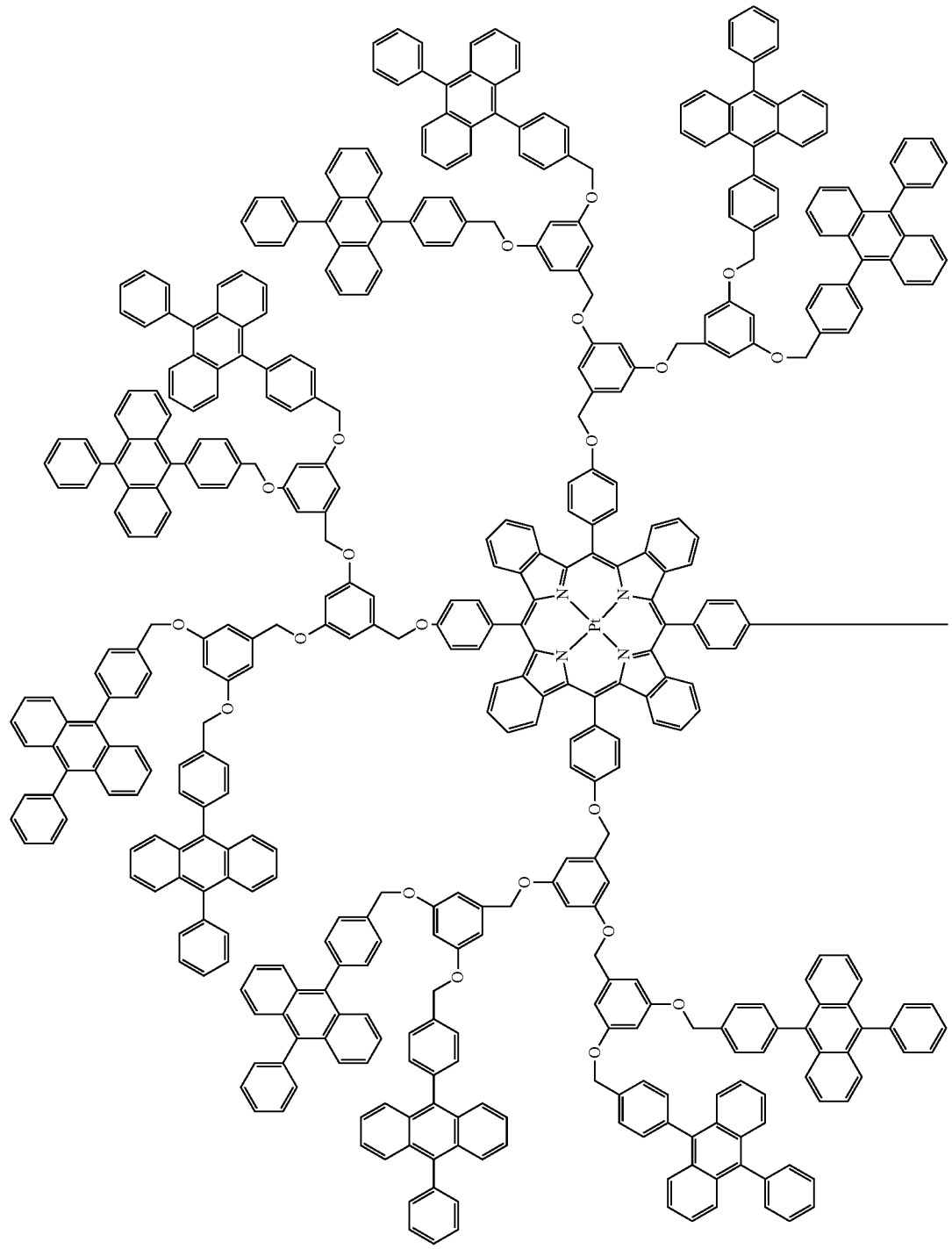

TABLE 3-continued
Example Compounds
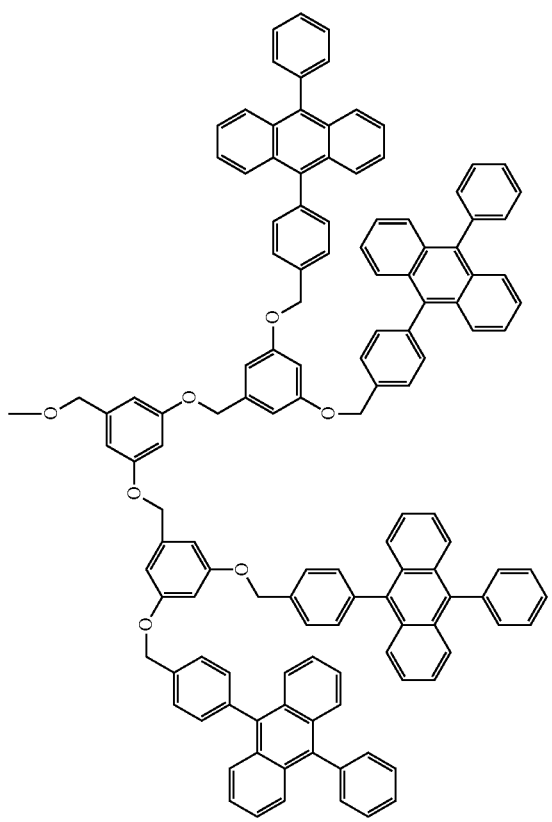

TABLE 3-continued
Example Compounds
Compound 10
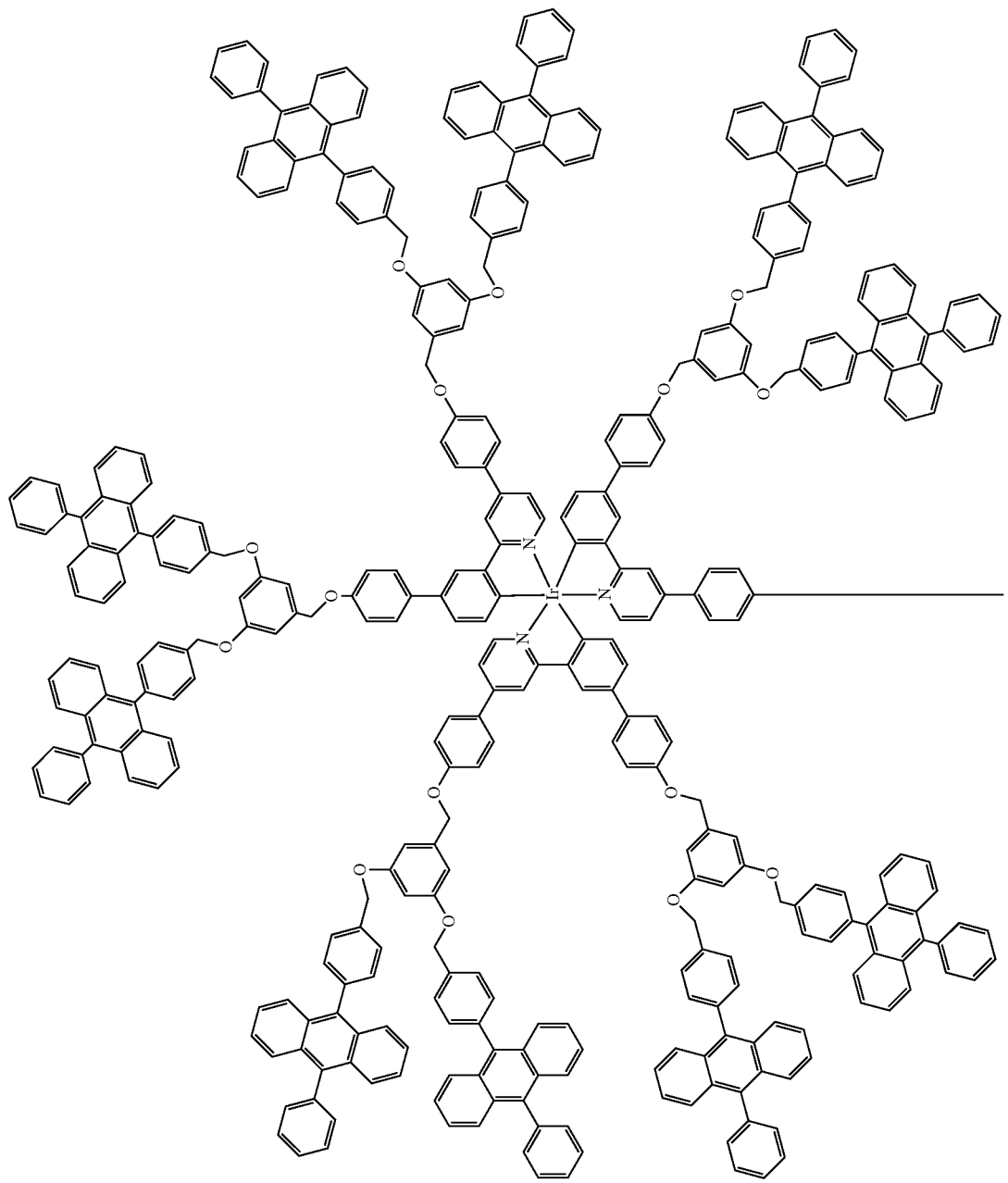

TABLE 3-continued
Example Compounds
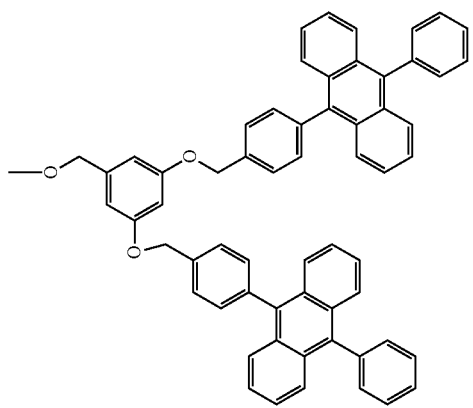

TABLE 3-continued
Example Compounds
Compound 11
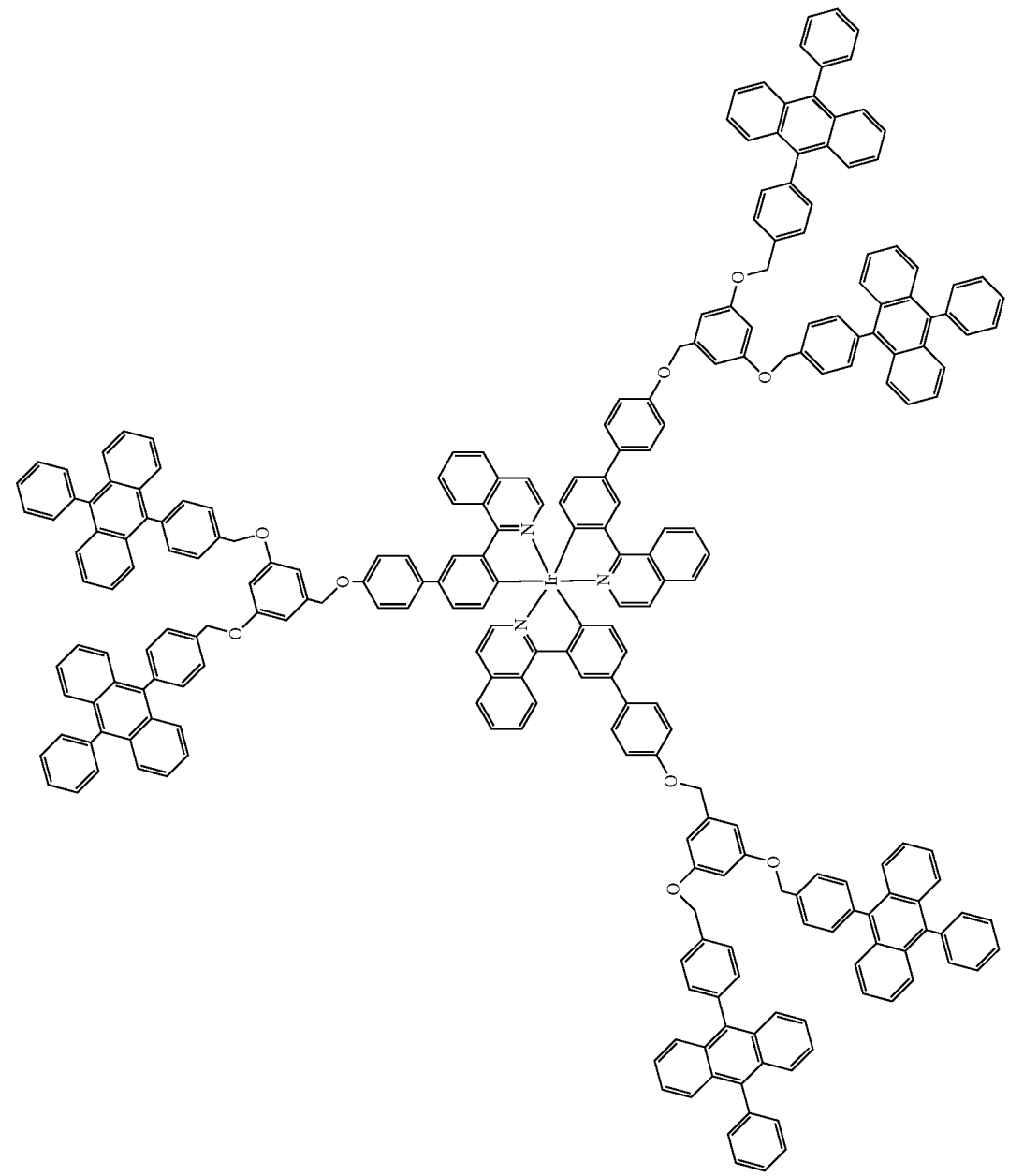

TABLE 3-continued
Example Compounds
Compound 12
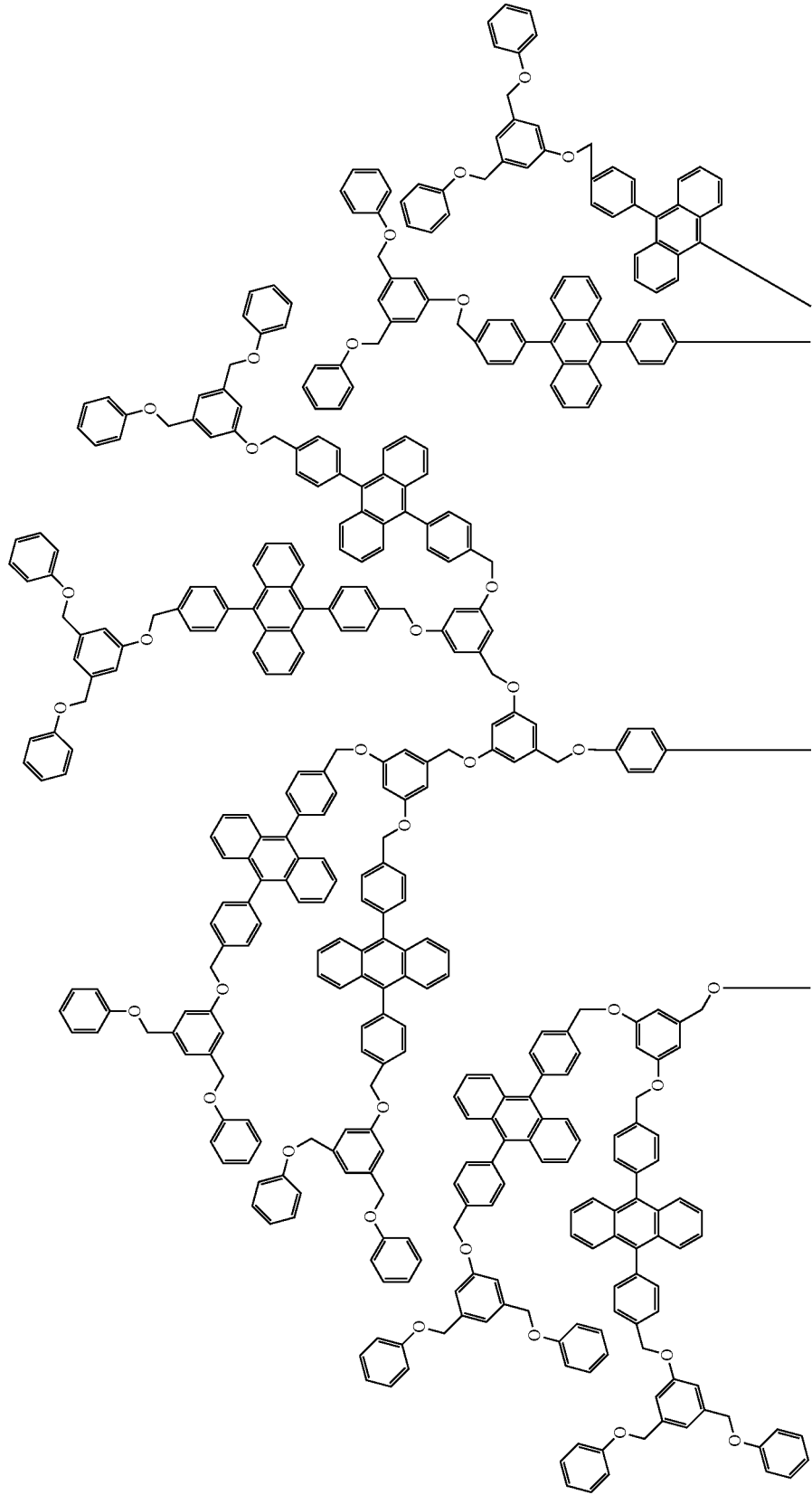

TABLE 3-continued
Example Compounds
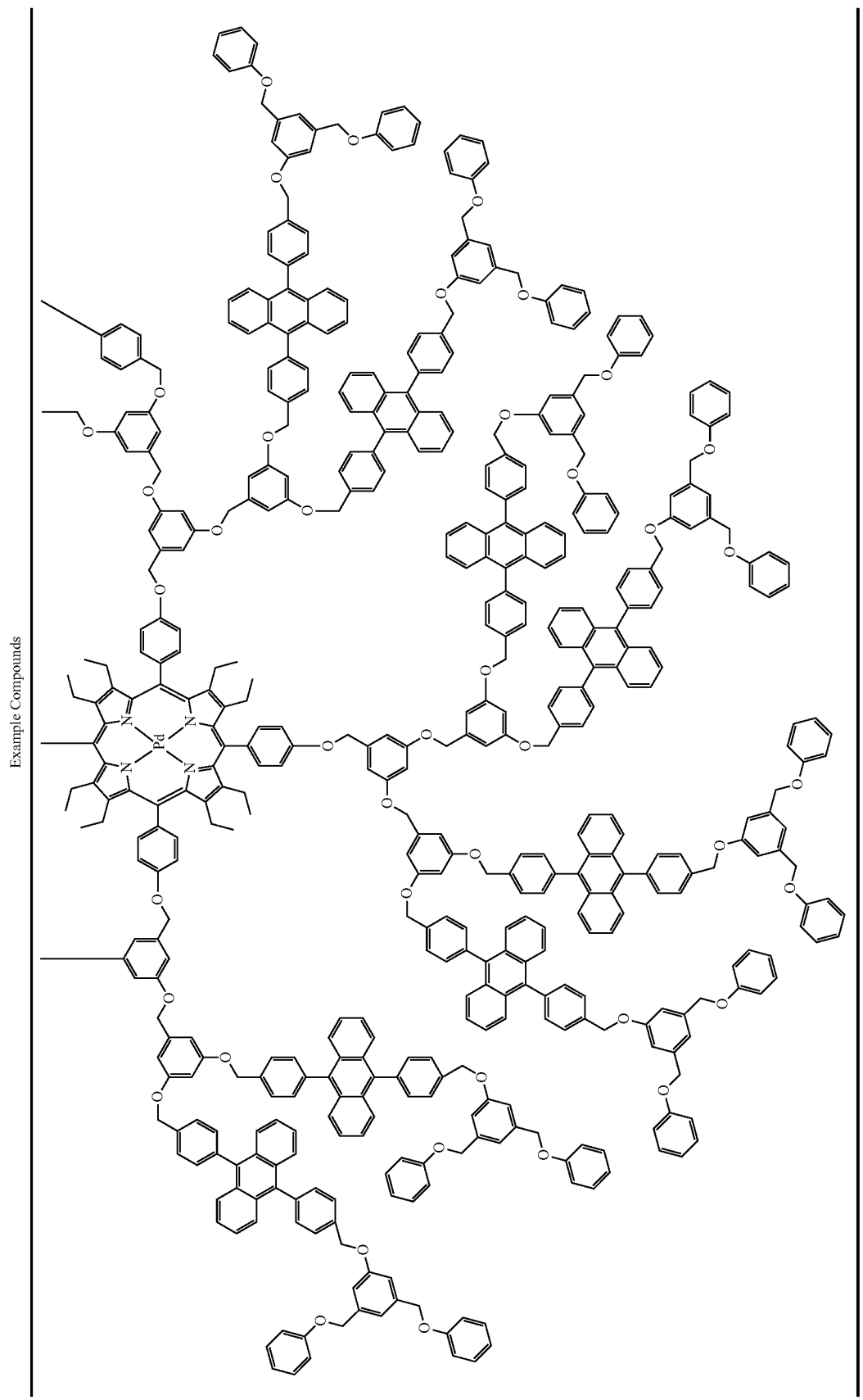

An organic light emitting device is also provided. The device may include an anode, a cathode, and an organic emissive layer disposed between the anode and the cathode. The organic emissive layer may include a host and a phosphorescent dopant.

The organic light emitting device may include an OLED, a thin film encapsulation layer disposed over or under the OLED, and an active matrix backplane.

Further, an organic light emitting device is provided, wherein the device includes an emissive material having an emissive spectrum. An up-conversion layer may be disposed adjacent to the organic light emitting device such that light emitted by the organic light emitting device is incident on the up-conversion layer. A compound, as described herein, may be included in the up-conversion layer.

Furthermore, a device including light-emitting diodes (LEDs) is provided, wherein the device includes the compounds described herein. The light source may be an inorganic LED. In an embodiment, the light source may be sun light.

In an embodiment, a photovoltaic device is provided. An upconversion layer may be disposed in the optical path of the incident light on the photovoltaic device. The upconversion layer may include the compounds described herein. In an embodiment, a lighting panel comprising the compounds described herein is provided.

A consumer product including a compound as described above is also provided.

In addition to the devices described above, the device may further include a touch sensitive surface. For example, the device may include a device type selected from the group consisting of: a full-color display, a flexible display in a consumer device, a mobile phone, a pad computer, a smart-phone, a portable computer, a monitor, a television, and a consumer device including a flexible display.

Combination with Other Materials

The materials described herein as useful for a particular layer in an organic light emitting device may be used in combination with a wide variety of other materials present in the device. For example, TTA-UC materials disclosed herein may be used in conjunction with a wide variety of hosts, transport layers, blocking layers, injection layers, electrodes and other layers that may be present. One of skill in the art can readily consult the literature to identify other materials that may be useful in combination.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

The invention claimed is:

1. A compound for triplet-triplet annihilation upconversion comprising:
    a metal complex sensitizer core;
    a first acceptor group; and
    a first spacer group between the metal complex core and the first acceptor group, wherein the first acceptor group has a first triplet energy lower than a first triplet energy of the metal complex sensitizer core;
    wherein the metal complex sensitizer core and the first acceptor group are jointly capable of performing triplet-triplet annihilation upconversion of light incident on the compound.

2. The compound of claim 1, wherein the first spacer group substantially surrounds the metal complex sensitizer core.

3. The compound of claim 1, further comprising a second spacer group, wherein the second spacer group substantially surrounds the first acceptor group.

4. The compound of claim 3, further comprising a second acceptor group.

5. The compound of claim 4, wherein the second acceptor group substantially surrounds the second spacer group.

6. The compound of claim 1, further comprising a second acceptor group.

7. The compound of claim 1, further comprising a second spacer group.

8. A device comprising a layer, the layer comprising a compound of claim 1.

9. The device of claim 8, wherein the device comprises an OLED.

10. The device of claim 9, further comprising a thin film encapsulation layer disposed over or under the OLED.

11. A consumer product comprising the compound of claim 1.

12. The compound of claim 1, wherein the first acceptor group is not bonded directly to the metal complex sensitizer core.

13. The compound of claim 12, wherein the first acceptor group is covalently linked to the metal complex sensitizer core through the first spacer group.

14. A compound for triplet-triplet annihilation upconversion, wherein the compound has the following general structure:

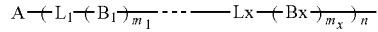

wherein A is a metal complex;
wherein $L_1$ to $L_x$ is a spacer group;
wherein $B_1$ to $B_x$ is an acceptor group B;
wherein $m_1$ is greater than 0;
wherein $m_x$ is equal to or greater than 0,
wherein n is greater than 0,
wherein the acceptor group B has a first triplet energy lower than a first triplet energy of the metal complex A; and
wherein the metal complex A and the acceptor group B are jointly capable of performing triplet-triplet annihilation upconversion of light incident on the compound.

15. The compound of claim 14, wherein ml is in the range of 1 to 20.

16. The compound of claim 14, wherein mx is in the range of 0 to 20.

17. The compound of claim 14, wherein n is in the range of 1 to 20.

18. The compound of claim 14, wherein the metal complex is selected from the group consisting of: an iridium complex, an osmium complex, a platinum complex, a palladium complex, a rhenium complex, a ruthenium complex, and a gold complex.

19. The compound of claim 14, wherein the acceptor group B is a fused aromatic group.

20. The compound of claim 14, wherein the acceptor group B is selected from the group consisting of: naphthalene, anthracene, tetracene, pyrene, chrysene, and perylene.

21. The compound of claim 14, wherein the ratio of the acceptor group B to the metal complex A is at least 4.

22. The compound of claim 14, wherein the spacer group L is selected from the group consisting of: alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, ester, and combinations thereof.

23. A device comprising a layer, the layer comprising a compound of claim 14.

24. The device of claim 23, wherein the device comprises a light emitting diode.

25. The device of claim 23, wherein the device comprises an OLED.

26. The device of claim 25, further comprising a thin film encapsulation layer disposed over or under the OLED.

27. A consumer product comprising the compound of claim 14.

28. A photovoltaic device comprising the compound of claim 14.

29. A device, comprising:
an organic light emitting device comprising an emissive material having an emissive spectrum; and
an up-conversion layer disposed adjacent to the organic light emitting device such that light emitted by the organic light emitting device is incident on the up-conversion layer, the up conversion layer comprising the compound of claim 14.

30. A compound selected from the group consisting of:

Compound 1

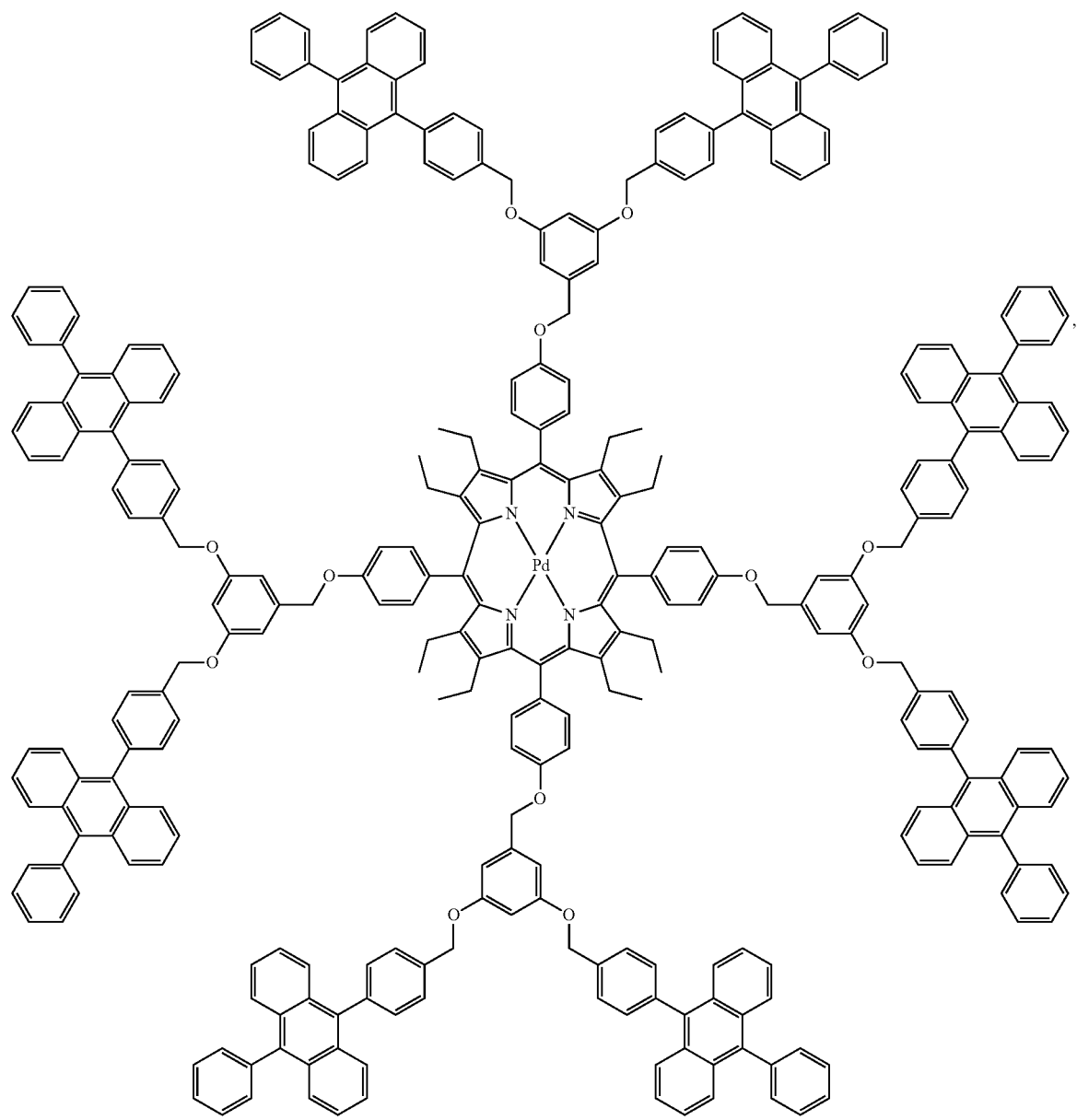

Compound 2
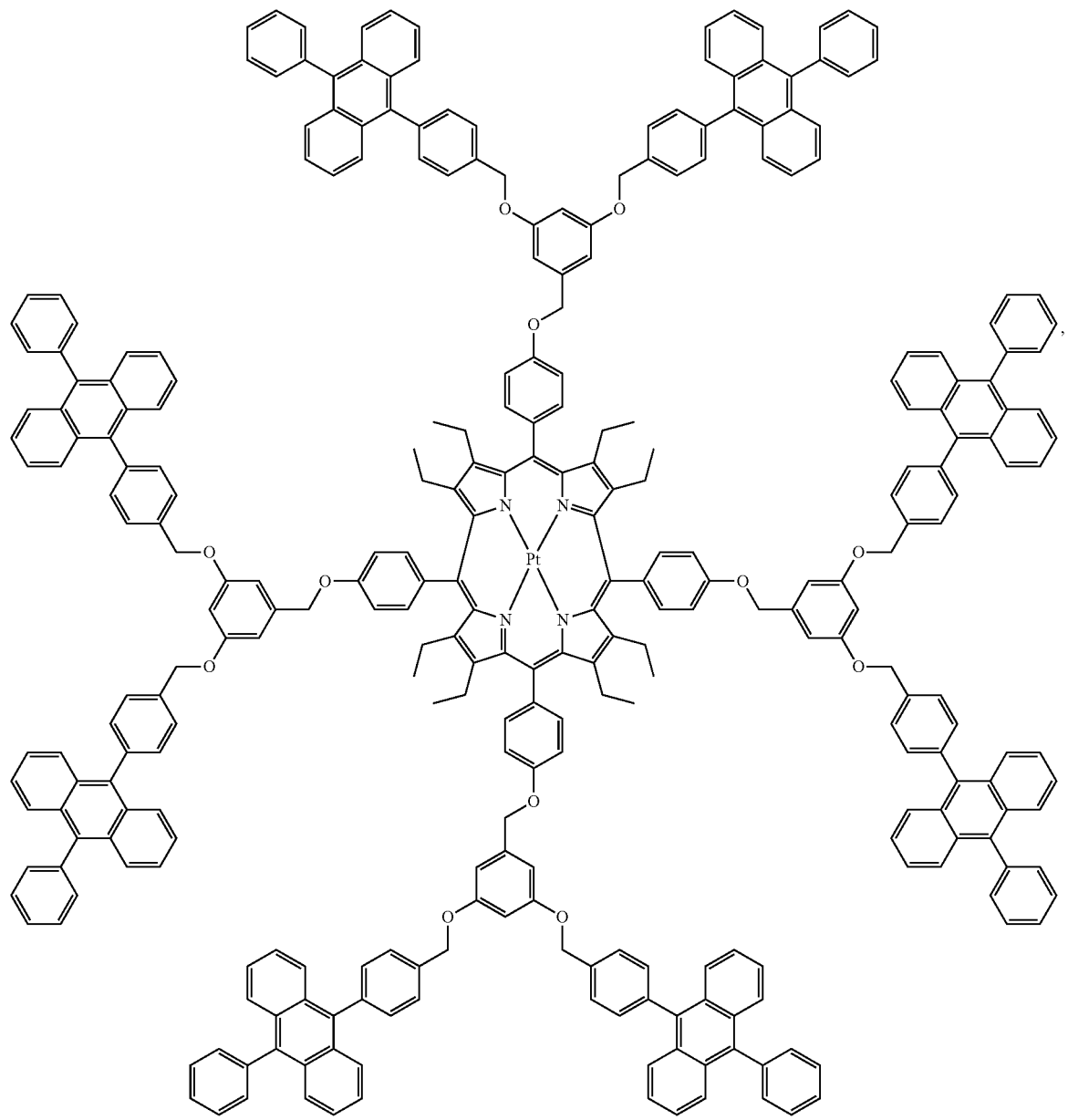

Compound 3
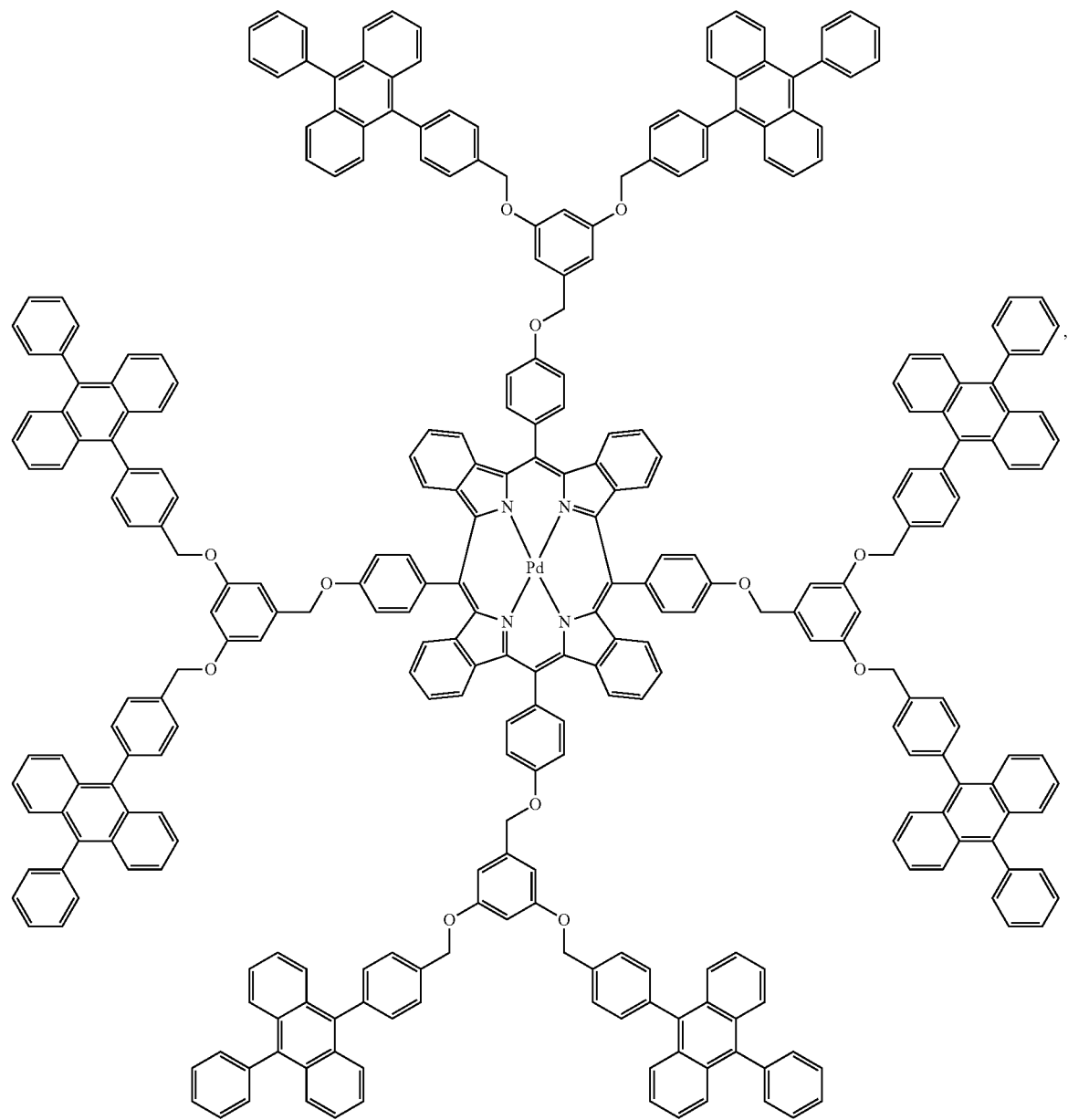

Compound 4
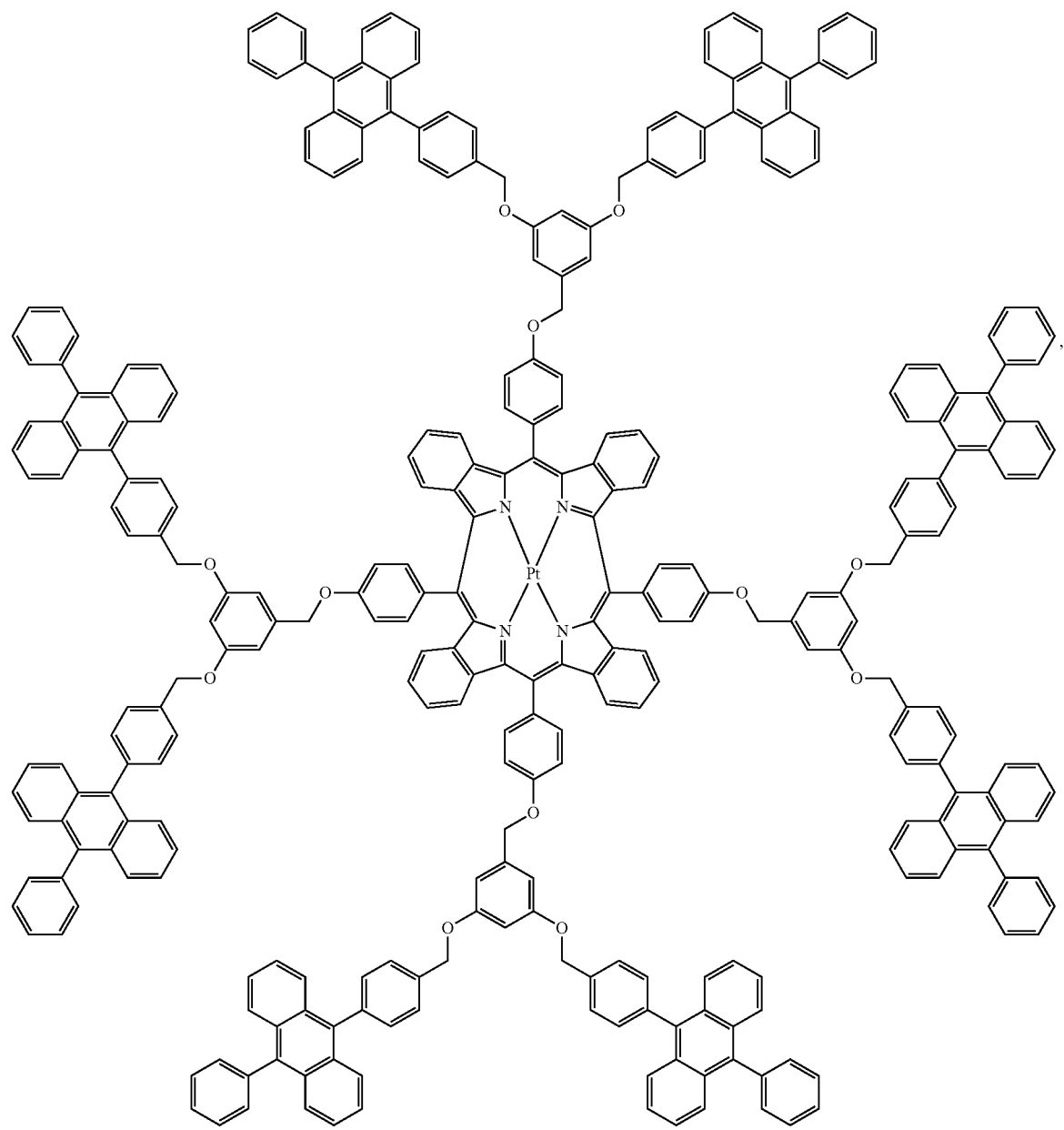

-continued
Compound 5
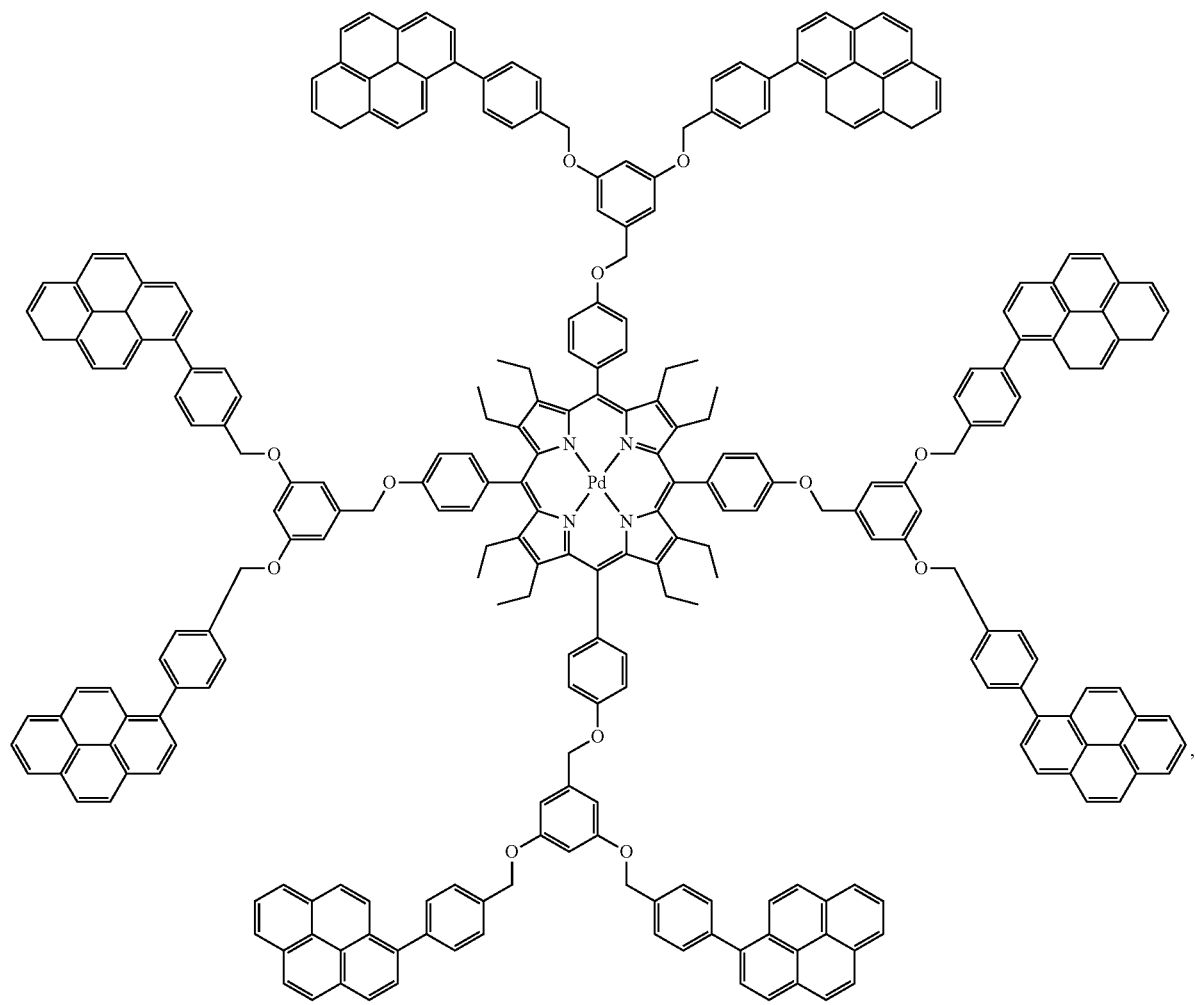

Compound 6
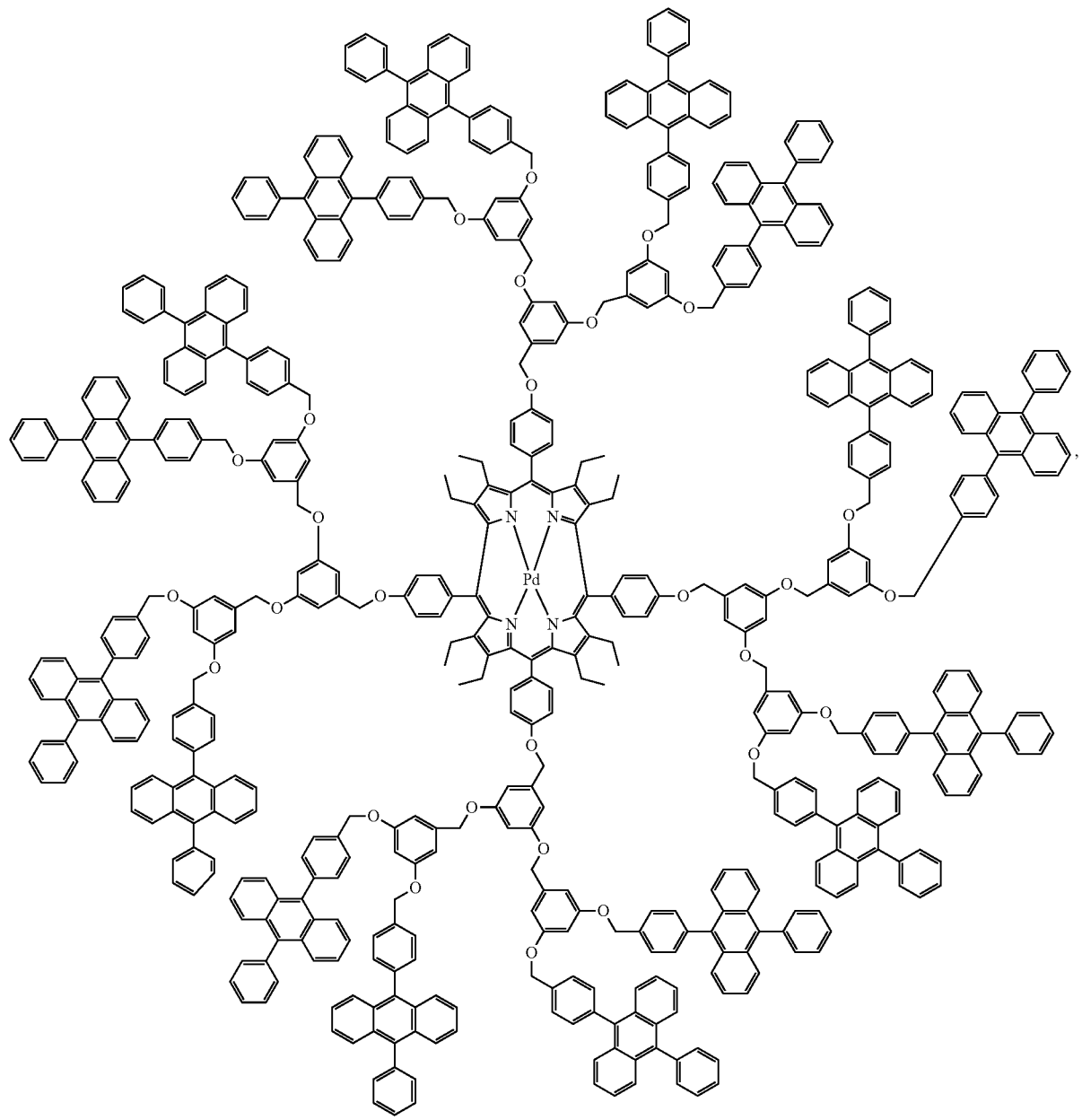

Compound 7
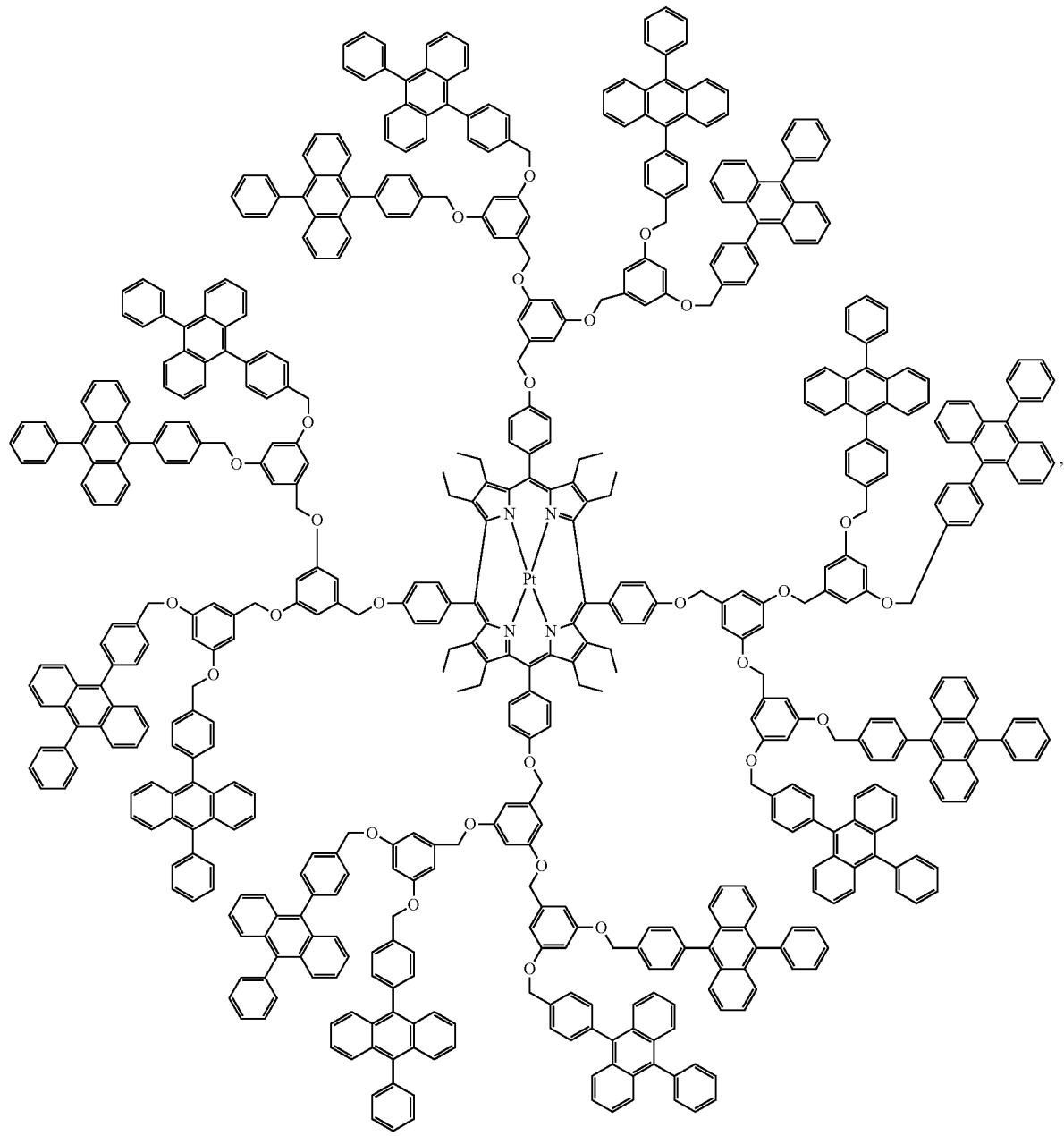

Compound 8
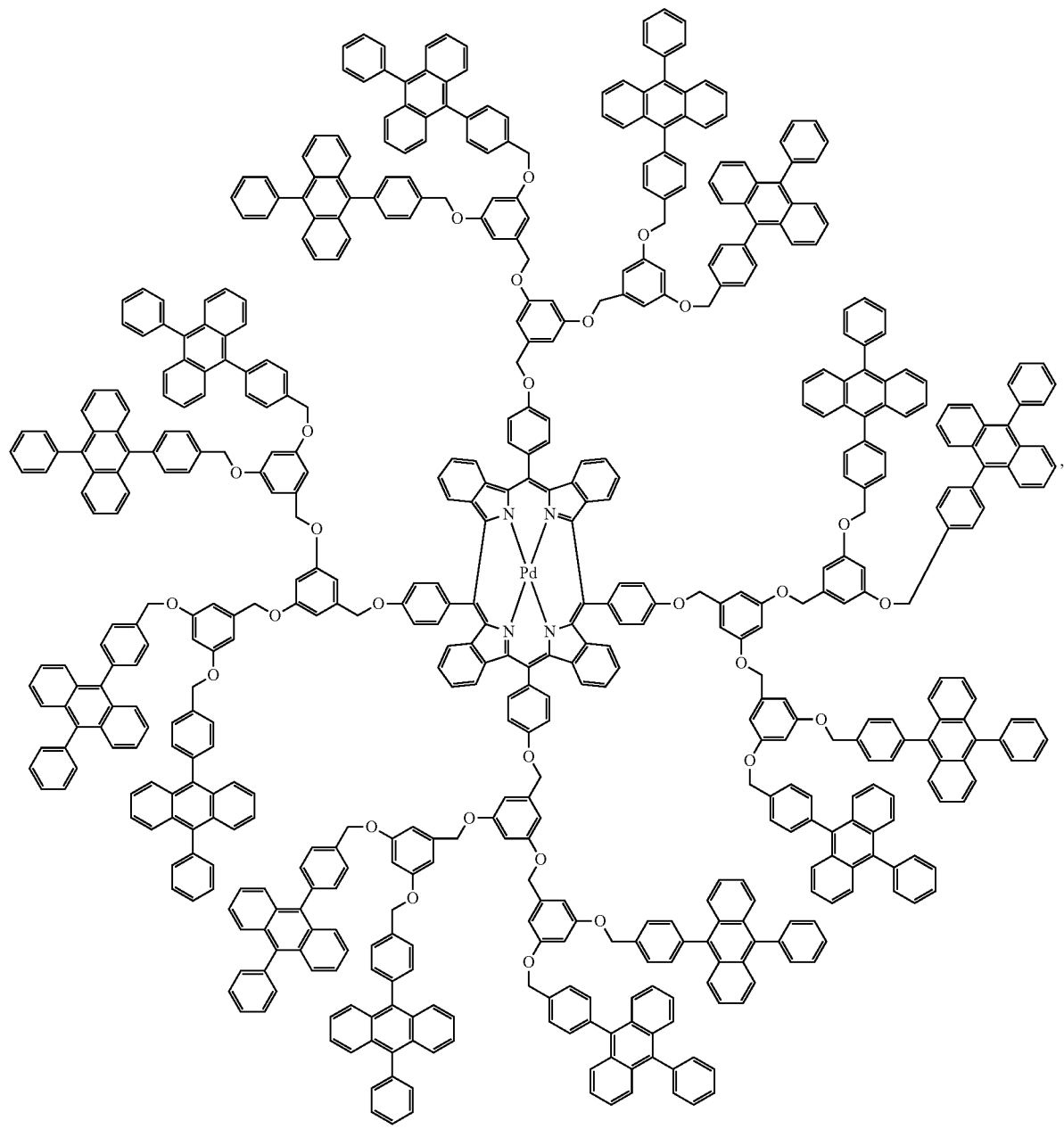

Compound 9
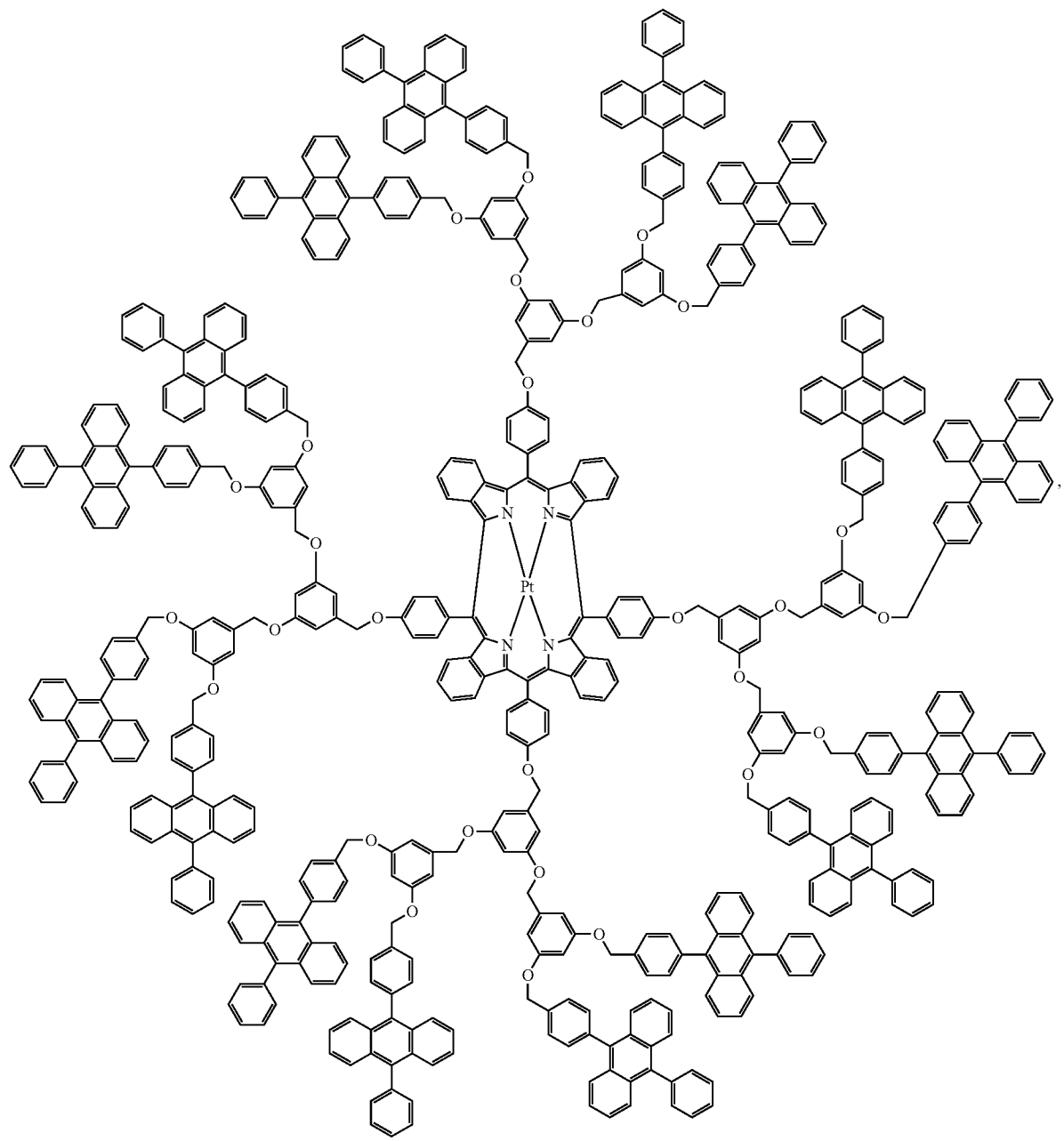

-continued
Compound 10
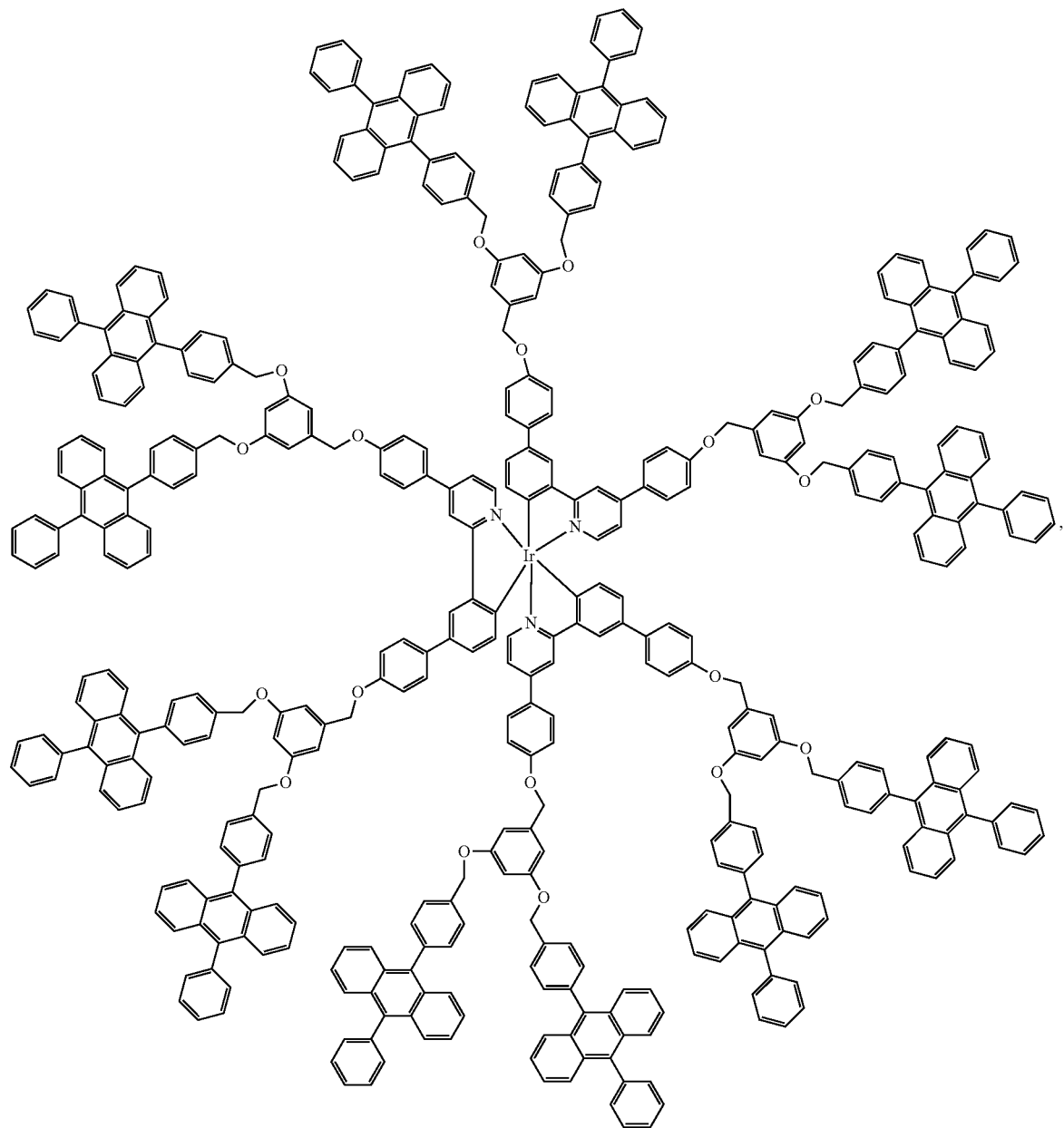

123    124
-continued
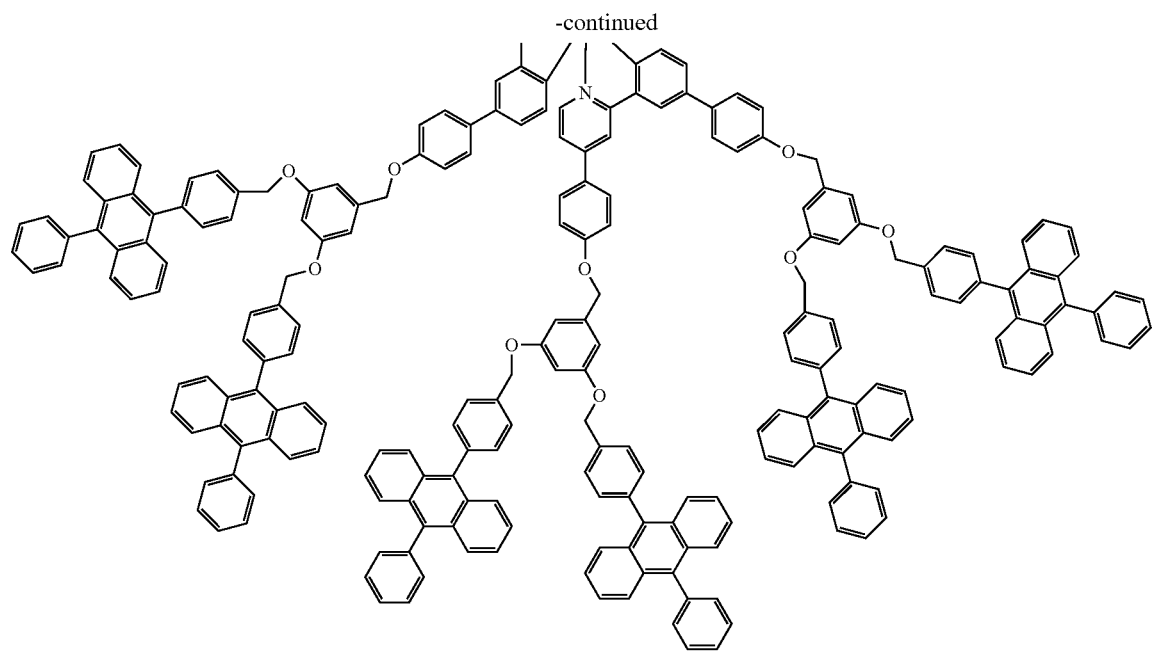

-continued
Compound 11
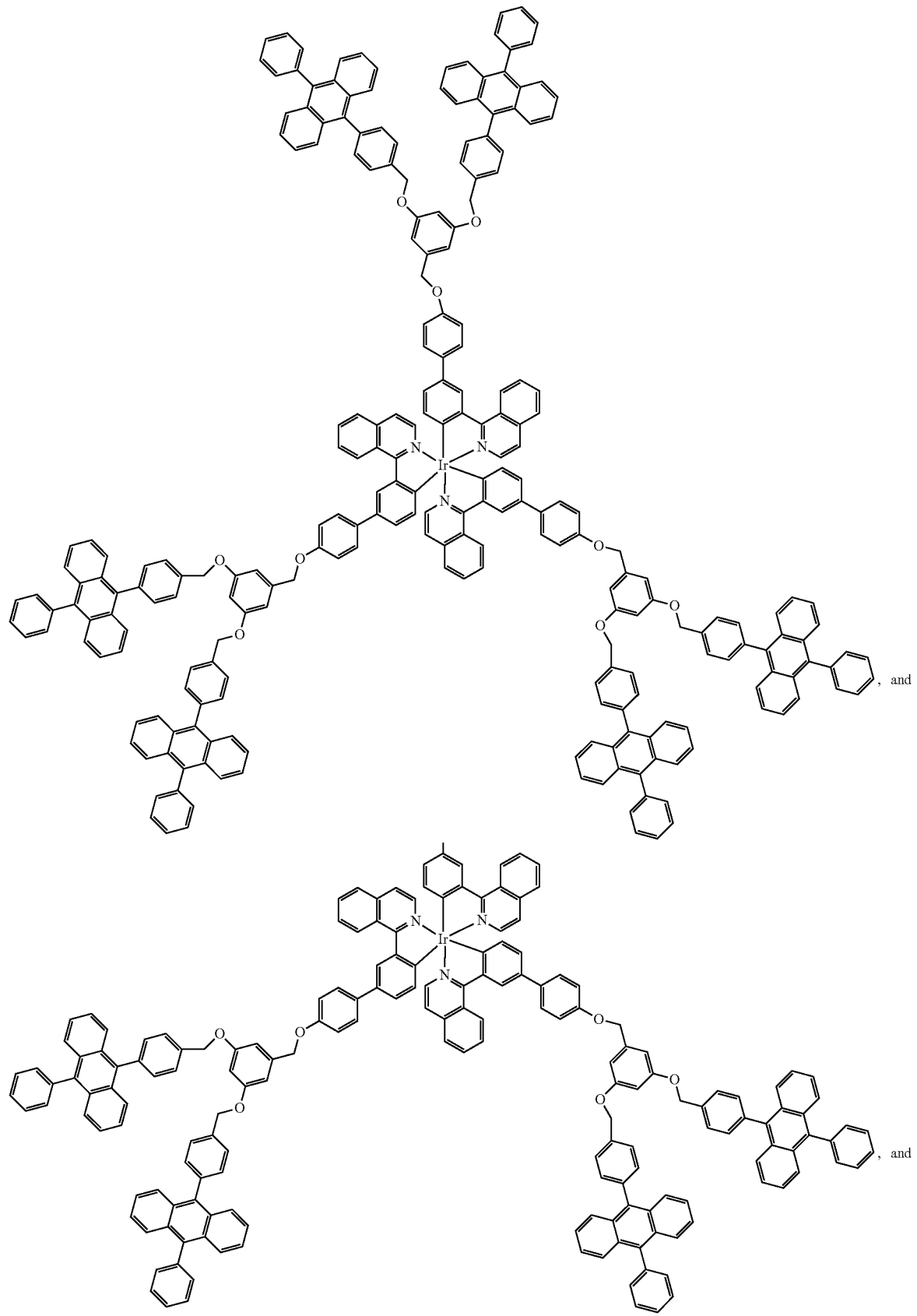
, and

-continued
Compound 12
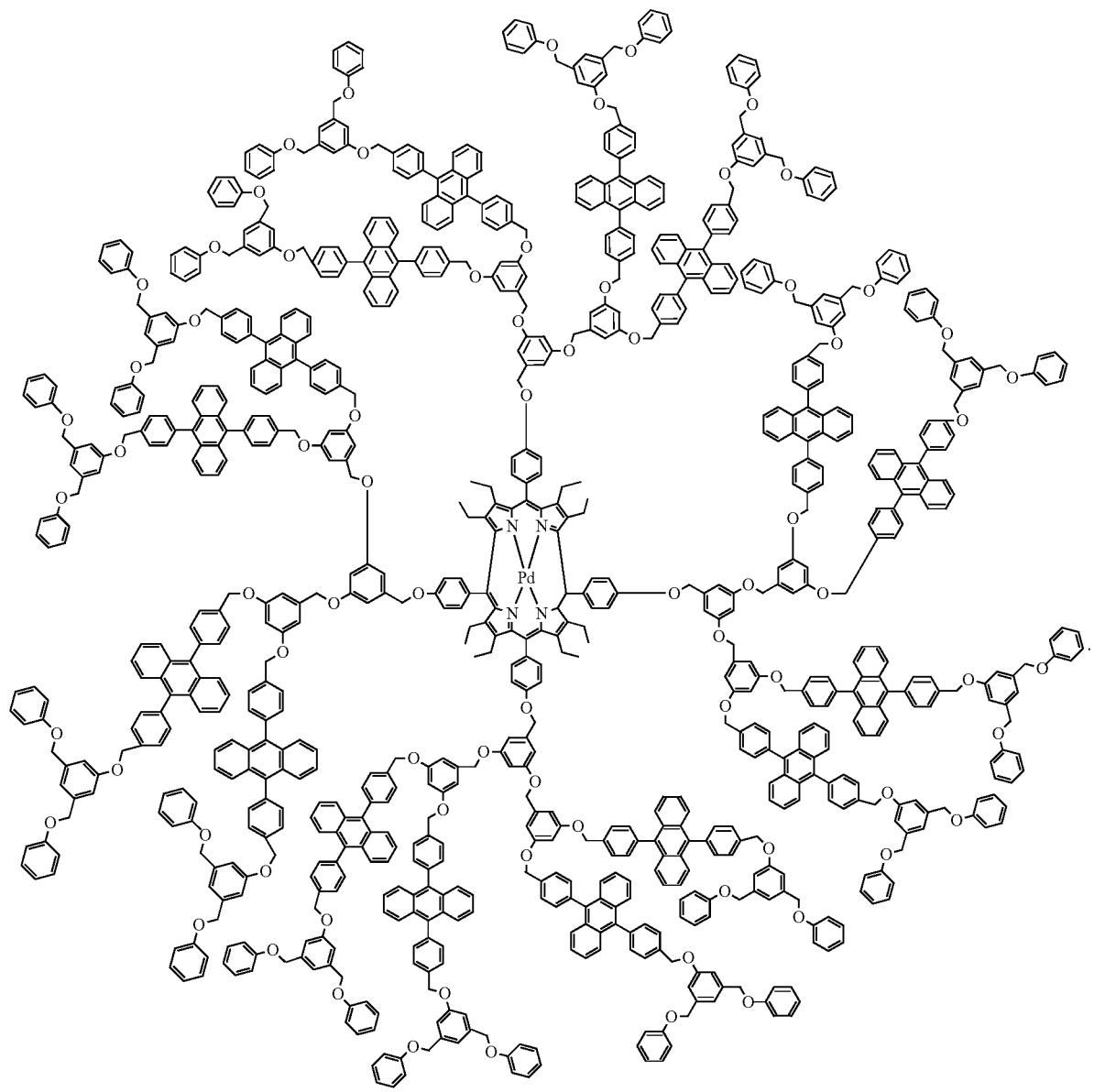
* * * * *